United States Patent
Hart et al.

(10) Patent No.: US 10,301,306 B2
(45) Date of Patent: May 28, 2019

(54) SUBSTITUTED DIHYDRO-1H-PYRROLO[3,2-C]PYRIDIN-4(5H)-ONES AS RIPK3 INHIBITORS

(71) Applicant: BRISTOL-MYERS SQUIBB COMPANY, Princeton, NJ (US)

(72) Inventors: Amy C. Hart, Ewing, NJ (US); William J. Pitts, Newtown, PA (US); Harold Mastalerz, Guilford, CT (US); Junqing Guo, Princeton, NJ (US); Gregory D. Brown, Lansdale, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 1 day.

(21) Appl. No.: 15/527,343

(22) PCT Filed: Dec. 14, 2015

(86) PCT No.: PCT/US2015/065466
§ 371 (c)(1),
(2) Date: May 17, 2017

(87) PCT Pub. No.: WO2016/100166
PCT Pub. Date: Jun. 23, 2016

(65) Prior Publication Data
US 2017/0362219 A1   Dec. 21, 2017

Related U.S. Application Data

(60) Provisional application No. 62/091,827, filed on Dec. 15, 2014.

(51) Int. Cl.
  *C07D 471/04* (2006.01)
(52) U.S. Cl.
  CPC ................... *C07D 471/04* (2013.01)
(58) Field of Classification Search
  CPC .................................................. C07D 471/04
  See application file for complete search history.

(56) References Cited

FOREIGN PATENT DOCUMENTS

| | | |
|---|---|---|
| JP | 05345784 A | 12/1993 |
| WO | WO2004/043491 A1 | 5/2004 |
| WO | WO2004/058762 A1 | 7/2004 |
| WO | WO2004058762 * | 7/2004 |
| WO | WO2005/105805 A1 | 11/2005 |
| WO | WO2007/042784 A2 | 4/2007 |
| WO | WO2009/044007 A2 | 4/2009 |
| WO | WO2010/145998 A1 | 12/2010 |
| WO | WO2010145998 * | 12/2010 |
| WO | WO2013/050446 A1 | 4/2013 |
| WO | WO2013/050448 A1 | 4/2013 |
| WO | WO2014/152182 A1 | 9/2014 |

OTHER PUBLICATIONS

CAS Registry No. 1027311-93-8 (Jun. 11, 2008).
CAS Registry No. 1026743-11-2 (Jun. 9, 2008).
CAS Registry No. 1026698-30-5 (Jun. 9, 2008).
CAS Registry No. 1026299-12-6 (Jun. 8, 2008).
CAS Registry No. 1026090-54-9 (Jun. 6, 2008).
CAS Registry No. 1025874-80-9 (Jun. 5, 2008).
CAS Report.

\* cited by examiner

*Primary Examiner* — Paul V Ward
(74) *Attorney, Agent, or Firm* — Hong Liu

(57) ABSTRACT

Compounds having Formula (I), and enantiomers, and diastereomers, stereoisomers, pharmaceutically-acceptable salts thereof, are useful as kinase modulators, including RIPK3 modulation. All the variables defined herein.

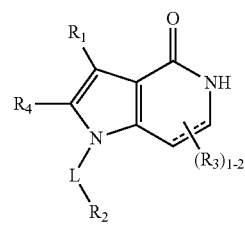

(I)

14 Claims, No Drawings

SUBSTITUTED DIHYDRO-1H-PYRROLO[3,2-C]PYRIDIN-4(5H)-ONES AS RIPK3 INHIBITORS

CROSS-REFERENCE TO RELATED APPLICATIONS

This application claims priority to U.S. Provisional Application Ser. No. 62/091,827, filed Dec. 15, 2014, the entire content of which is incorporated herein by reference.

FIELD OF THE INVENTION

The present invention relates to novel compounds that inhibit receptor interacting protein kinases and methods of making and using the same. Specifically, the present invention relates to substituted dihydro-1H-pyrrolo[3,2-c]pyridines as receptor interacting protein kinase 3 (RIPK3) inhibitors.

BACKGROUND OF THE INVENTION

Apoptosis and necrosis represent two different mechanisms of cell death. Apoptosis is a highly regulated process involving the caspase family of cysteine proteases, and characterized by cellular shrinkage, chromatin condensation, and DNA degradation. In contrast, necrosis is associated with cellular and organelle swelling and plasma membrane rupture with ensuing release of intracellular contents and secondary inflammation (Kroemer et al., *Cell Death Differ.*, 16:3-11 (2009)). Necrosis has been considered a passive, unregulated form of cell death; however, recent evidence indicates that some necrosis can be induced by regulated signal transduction pathways such as those mediated by receptor interacting protein kinases (RIPKs) especially in conditions where caspases are inhibited or cannot be activated efficiently (Golstein, P. et al., *Trends Biochem. Sci.*, 32:37-43 (2007); Festjens et al., Biochim. Biophys. Acta, 1757:1371-1387 (2006)). Stimulation of the Fas and TNFR family of death domain receptors (DRs) is known to mediate apoptosis in most cell types through the activation of the extrinsic caspase pathway. In addition, in certain cells deficient for caspase-8 or treated with pan-caspase inhibitor Z-VAD, stimulation of death domain receptors (DR) causes a receptor interacting protein kinase 1 (RIPK1) dependent programmed necrotic cell death instead of apoptosis (Holler et al., *Nat. Immunol.*, 1:489-495 (2000); Degterev et al., *Nat. Chem. Biol.*, 4:313-321 (2008)). This novel mechanism of cell death is termed "programmed necrosis" or "necroptosis" (Degterev et al., *Nat. Chem. Biol.*, 1:112-119 (2005)).

Necroptosis can be triggered upon activation of TNF receptors or Toll-like receptors in response to genotoxic stress and during virus infection and has been shown to be RIPK1 and RIPK3 dependent. Studies reveal that the expression of RIPK3 and the RIPK1-RIPK3 binding through the RIP homotypic interaction motif (RHIM) is a prerequisite for RIPK1 activation, leading to reactive oxygen species (ROS) production and necrotic cell death (He et al., *Cell*, 137:1100-1111 (2009); Cho et al., *Cell*, 137:1112-1123 (2009); Zhang et al., *Science*, 325:332-336 (2009)).

Dysregulation of RIPK3-dependent signaling has been linked to inflammatory diseases such as macrophage necrosis in atherosclerosis development, virus-induced inflammation, systemic inflammatory response syndrome and ethanol-induced liver injury, neurodegeneration such as detachment of the retina, ischemia, and Gaucher's disease (Trichonas et al., *Proc. Natl. Acad. Sci.*, 107:21695-21700 (2010); Lin et al., *Cell Rep.*, 3:200-210 (2013); Cho et al., *Cell*, 137:1112-1123 (2009); Duprez et al., *Immunity*, 35:908-918 (2011); Roychowdhury et al., *Hepatology*, 57:1773-1783 (2013); Vandenabeele et al., *Nature*, 10:700-714 (2010); Vandenabeele et al., *Sci. Signalling*, 3:1-8 (2010); Zhang et al., *Cell. Mol. Immunol.*, 7:243-249 (2010); Moriwaki et al., *Genes Dev.*, 27:1640-1649 (2013); Vitner et al., *Nat. Med.*, 20:204-208 (2014)).

A potent, selective, small molecule inhibitor of RIPK3 activity would block RIPK3-dependent pro-inflammatory signaling and thereby provide a therapeutic benefit in inflammatory diseases characterized by increased and/or dysregulated RIPK3 kinase activity.

SUMMARY OF THE INVENTION

The present invention provides novel dihydro-1H-pyrrolo[3,2-c]pyridinones including stereoisomers, tautomers, pharmaceutically acceptable salts, or solvates thereof, which are useful as inhibitors of RIPK3.

The present invention also provides processes and intermediates for making the compounds of the present invention.

The present invention also provides pharmaceutical compositions comprising a pharmaceutically acceptable carrier and at least one of the compounds of the present invention or stereoisomers, tautomers, pharmaceutically acceptable salts, or solvates thereof.

The compounds of the invention may be used in the treatment and/or prophylaxis of conditions associated with aberrant RIPK3 activity.

The compounds of the present invention may be used in therapy.

The compounds of the present invention may be used for the manufacture of a medicament for the treatment and/or prophylaxis of a condition associated with aberrant RIPK3 activity.

In another aspect, the present invention is directed to a method of treating diseases mediated at least partially by RIPK3 including inflammatory diseases, ischemia, neurodegeneration, and Gaucher's disease, which method comprises administering to a patient in need of such treatment a compound of the present invention as described above.

The compounds of the invention can be used alone, in combination with other compounds of the present invention, or in combination with one or more, preferably one to two other agent(s).

These and other features of the invention will be set forth in expanded form as the disclosure continues.

DETAILED DESCRIPTION OF EMBODIMENTS OF THE INVENTION

In one aspect, the present invention provides, inter alia, compounds of Formula (I):

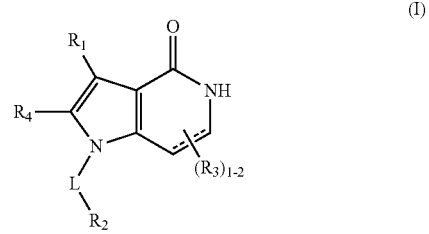

or stereoisomers, tautomers, pharmaceutically acceptable salts, solvates, or prodrugs thereof, wherein:

--- is an optional bond;

$R_1$ is selected from —$(CR_dR_d)_r$—$C_{3-10}$ carbocyclyl substituted with 1-5 $R_5$, —$CR_d$=$CR_d$—$C_{3-10}$ carbocyclyl substituted with 1-5 $R_5$, and heterocyclyl comprising carbon atoms and 1 to 3 heteroatoms selected from N, O, S, and substituted with 1-5 $R_5$;

L is selected from —$(CR_dR_d)_r$— and —$S(O)_p$—;

$R_2$ is selected H, $C_{1-2}$ alkyl substituted with 0-3 $R_e$, carbocyclyl substituted with 1-8 $R_7$, heterocyclyl, comprising carbon atoms and 1 to 4 heteroatoms selected from N, O, S, wherein said heterocyclyl is substituted with 1-8 $R_7$;

$R_3$ is selected from H, CN, $C_{1-4}$ alkyl substituted with 0-3 $R_e$, —C(=O)$OR_b$, —C(=O)$NR_aR_a$, —C(=O)$R_b$, —$NR_aC$(=O)$R_b$, —$NR_aC$(=O)$OR_b$, $C_{3-6}$carbocycle substituted with 0-3 $R_e$, and heterocycle substituted with 0-3 $R_e$;

$R_4$ is selected from

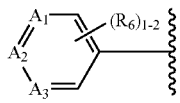

and 5-membered heteroaryl substituted with 1-5 $R_6$;

$A_1$, $A_2$, and $A_3$ are independently selected from N and $CR_6$; provided $A_1$, $A_2$, and $A_3$ are not all nitrogen;

$R_5$ is selected from H, $C_{1-4}$ alkyl substituted with 0-3 $R_e$, F, Cl, Br, =O, CN, $NO_2$, —$(CH_2)_rCN$, —$(CH_2)_rOR_b$, $(CH_2)_rS(O)_pR_c$, —$(CH_2)_rC$(=O)$R_b$, —$(CH_2)_rNR_aR_a$, —$(CH_2)_rC$(=O)$NR_aR_a$, —$(CH_2)_rNR_aC$(=O)$R_b$, —$(CH_2)_rNR_aC$(=O)$OR_b$, —$(CH_2)_rOC$(=O)$NR_aR_a$, —$(CH_2)_rNR_aC$(=O)$NR_aR_a$, —$(CH_2)_rC$(=O)$OR_b$, —$(CH_2)_rS(O)_2NR_aR_a$, —$(CH_2)_rNR_aS(O)_2NR_aR_a$, —$(CH_2)_rNR_aS(O)_2R_c$, $(CH_2)_r$-carbocyclyl substituted with 0-3 $R_e$, and —$(CH_2)_r$-heterocyclyl substituted with 0-3 $R_e$;

$R_6$ is selected from H, F, Cl, Br, $C_{1-4}$ alkyl substituted with 0-3 $R_e$, —$(CH_2)_rCN$, —$(CH_2)_rOR_b$, $(CH_2)_rS(O)_pR_c$, —$(CH_2)_rC$(=O)$R_b$, —$(CH_2)_rNR_aR_a$, —$(CH_2)_rC$(=O)$NR_aR_a$, —$(CH_2)_rC$(=O)—$C_{1-4}$ alkyl substituted with 0-3 $R_e$, —$(CH_2)_rNR_aC$(=O)$R_b$, —$(CH_2)_rNR_aC$(=O)$OR_b$, —$(CH_2)_rOC$(=O)$NR_aR_a$, —$(CH_2)_rNR_aC$(=O)$NR_aR_a$, —$(CH_2)_rC$(=O)$OR_b$, —$(CH_2)_rS(O)_2NR_aR_a$, —$(CH_2)_rNR_aS(O)_2NR_aR_a$, —$(CH_2)_rNR_aS(O)_2R_c$, $(CH_2)_r$-carbocyclyl substituted with 0-3 $R_e$, and —$(CH_2)_r$-heterocyclyl substituted with 0-3 $R_e$; alternatively, two adjacent $R_6$ groups are taken together to form a heterocycle;

$R_7$, at each occurrence, is independently selected from H, F, Cl, Br, =O, CN, $NO_2$, —$OR_b$, —$S(O)_pR_c$, —C(=O)$R_b$, —$(CR_dR_d)_rNR_aR_a$, —$(CR_dR_d)_rC$(=O)$NR_aR_a$, —$NR_aC$(=O)$R_b$, —$NR_aC$(=O)$OR_b$, —OC(=O)$NR_aR_a$, —$NR_aC$(=O)$NR_aR_a$, —$(CR_dR_d)_rC$(=O)$OR_b$, —$S(O)_2NR_aR_a$, —$NR_aS(O)_2NR_aR_a$, —$NR_aS(O)_2R_c$, $C_{1-6}$ alkyl substituted with 0-5 $R_e$, —$(CR_dR_d)_r$—$C_{3-6}$carbocyclyl substituted with 0-5 $R_e$, and —$(CR_dR_d)_r$-heterocyclyl substituted with 0-5 $R_e$;

$R_a$, at each occurrence, is independently selected from H, CN, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_d$, at each occurrence, is independently selected from H and $C_{1-4}$alkyl substituted with 0-5 $R_e$; or $R_d$ and $R_d$ together are =O;

$R_e$, at each occurrence, is independently selected from $C_{1-6}$ alkyl substituted with 0-5 $R_f$, $C_{2-6}$ alkenyl, $C_{2-6}$ alkynyl, aryl, —$(CH_2)_r$—$C_{3-6}$ cycloalkyl, F, Cl, Br, CN, $NO_2$, =O, $CO_2H$, —C(=O)$NR_fR_f$, —$(CH_2)_rOR_f$, $SR_f$, and —$(CH_2)_rNR_fR_f$;

$R_f$, at each occurrence, is independently selected from H, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

p, at each occurrence, is independently selected from zero, 1, and 2; and r, at each occurrence, is independently selected from zero, 1, 2, 3, and 4.

In another aspect, the present invention provides compounds of Formula (II):

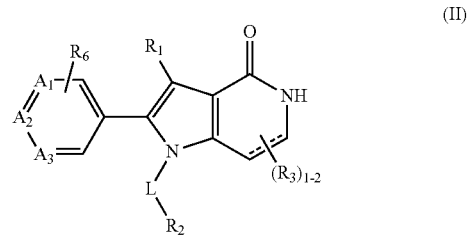

(II)

or stereoisomers, tautomers, pharmaceutically acceptable salts, solvates, or prodrugs thereof, wherein:

--- is an optional bond;

$A_1$, $A_2$, and $A_3$ are independently selected from N and $CR_6$;

$R_1$ is selected from aryl substituted with 1-4 $R_5$, and 5- to 12-membered heteroaryl comprising carbon atoms and 1 to 3 heteroatoms selected from N, O, S, and substituted with 1-4 $R_5$;

L is selected from —$(CR_dR_d)_r$— and —$S(O)_p$—;

$R_2$ is selected from H, $C_{1-2}$ alkyl substituted with 0-3 $R_e$, $C_{3-12}$ carbocyclyl substituted with 1-5 $R_7$, and 5- to 12-membered heterocyclyl comprising carbon atoms and 1 to 4 heteroatoms selected from N, O, S, and substituted with 1-5 $R_7$;

$R_3$ is selected from H and $C_{1-4}$ alkyl substituted with 0-3 $R_e$;

$R_5$ is selected from H, $C_{1-4}$ alkyl substituted with 0-3 $R_e$, F, Cl, Br, =O, CN, $NO_2$, —$(CH_2)_rOR_b$, —$(CH_2)_rCN$, $(CH_2)_rS(O)_pR_c$, —$(CH_2)_rC$(=O)$R_b$, —$(CH_2)_rNR_aR_a$, —$(CH_2)_rC$(=O)$NR_aR_a$, —$(CH_2)_rNR_aC$(=O)$R_b$, —$(CH_2)_rNR_aC$(=O)$OR_b$, —$(CH_2)_rOC$(=O)$NR_aR_a$, —$(CH_2)_rNR_aC$(=O)$NR_aR_a$, —$(CH_2)_rC$(=O)$OR_b$, —$(CH_2)_rS(O)_2NR_aR_a$, —$(CH_2)_rNR_aS(O)_2NR_aR_a$, —(CH$_2$)$_r$NR$_a$S(O)$_2$R$_c$, (CH$_2$)$_r$-carbocyclyl substituted with 0-3 R$_e$, and —(CH$_2$)$_r$-heterocyclyl substituted with 0-3 R$_e$;

R$_6$ is selected from H, F, Cl, Br, C$_{1-4}$ alkyl substituted with 0-3 R$_e$, —(CH$_2$)$_r$CN, —(CH$_2$)$_r$OR$_b$, (CH$_2$)$_r$S(O)$_p$R$_c$, —(CH$_2$)$_r$C(=O)R$_b$, —(CH$_2$)$_r$NR$_a$R$_a$, —(CH$_2$)$_r$C(=O)NR$_a$R$_a$, —(CH$_2$)$_r$C(=O)—C$_{1-4}$ alkyl substituted with 0-3 R$_e$, —(CH$_2$)$_r$NR$_a$C(=O)R$_b$, —(CH$_2$)$_r$NR$_a$C(=O)OR$_b$, —(CH$_2$)$_r$OC(=O)NR$_a$R$_a$, —(CH$_2$)$_r$NR$_a$C(=O)NR$_a$R$_a$, —(CH$_2$)$_r$C(=O)OR$_b$, —(CH$_2$)$_r$S(O)$_2$NR$_a$R$_a$, —(CH$_2$)$_r$NR$_a$S(O)$_2$NR$_a$R$_a$, —(CH$_2$)$_r$NR$_a$S(O)$_2$R$_c$, (CH$_2$)$_r$-carbocyclyl substituted with 0-3 R$_e$, and —(CH$_2$)$_r$-heterocyclyl substituted with 0-3 R$_e$;

R$_7$, at each occurrence, is independently selected from H, F, Cl, Br, =O, CN, NO$_2$, —OR$_b$, —S(O)$_p$R$_c$, —C(=O)R$_b$, —(CR$_d$R$_d$)$_r$NR$_a$R$_a$, —(CR$_d$R$_d$)$_r$C(=O)NR$_a$R$_a$, —NR$_a$C(=O)R$_b$, —NR$_a$C(=O)OR$_b$, —OC(=O)NR$_a$R$_a$, —NR$_a$C(=O)NR$_a$R$_a$, —(CR$_d$R$_d$)$_r$C(=O)OR$_b$, —S(O)$_2$NR$_a$R$_a$, —NR$_a$S(O)$_2$NR$_a$R$_a$, —NR$_a$S(O)$_2$R$_c$, C$_{1-6}$ alkyl substituted with 0-5 R$_e$, —(CR$_d$R$_d$)$_r$—C$_{3-6}$carbocyclyl substituted with 0-5 R$_e$, and —(CR$_d$R$_d$)$_r$-heterocyclyl substituted with 0-5 R$_e$;

R$_a$, at each occurrence, is independently selected from H, CN, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$; or R$_a$ and R$_a$ together with the nitrogen atom to which they are both attached form a heterocyclic ring substituted with 0-5 R$_e$;

R$_b$, at each occurrence, is independently selected from H, C$_{1-6}$ alkyl substituted with 0-5 R$_c$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$;

R$_c$, at each occurrence, is independently selected from C$_{1-6}$ alkyl substituted with 0-5 R$_e$, C$_{2-6}$alkenyl substituted with 0-5 R$_e$, C$_{2-6}$alkynyl substituted with 0-5 R$_e$, C$_{3-6}$carbocyclyl, and heterocyclyl;

R$_d$, at each occurrence, is independently selected from H and C$_{1-4}$alkyl substituted with 0-5 R$_e$; or R$_d$ and R$_d$ together are =O;

R$_e$, at each occurrence, is independently selected from C$_{1-6}$ alkyl substituted with 0-5 R$_f$, C$_{2-6}$ alkenyl, C$_{2-6}$ alkynyl, aryl, —(CH$_2$)$_r$—C$_{3-6}$ cycloalkyl, F, Cl, Br, CN, NO$_2$, =O, CO$_2$H, —(CH$_2$)$_r$OR$_f$, SR$_f$, and —(CH$_2$)$_r$NR$_f$R$_f$;

R$_f$, at each occurrence, is independently selected from H, C$_{1-5}$ alkyl, C$_{3-6}$ cycloalkyl, and phenyl, or R$_f$ and R$_f$ together with the nitrogen atom to which they are both attached form a heterocyclic ring optionally substituted with C$_{1-4}$alkyl;

p, at each occurrence, is independently selected from zero, 1, and 2; and r, at each occurrence, is independently selected from zero, 1, 2, 3, and 4.

In another aspect, the present invention provides compounds of Formula (II) or stereoisomers, tautomers, pharmaceutically acceptable salts, solvates, or prodrugs thereof, wherein:

R$_1$ is selected from phenyl, pyridyl, pyrimidinyl, pyrazinyl, pyridazinyl, triazinyl, furyl, thienyl, imidazolyl, thiazolyl, indolyl, oxazolyl, isoxazolyl, pyrazolyl, triazolyl, tetrazolyl, indazolyl, 1,2,4-thiadiazolyl, isothiazolyl, quinolinyl, and isoquinolinyl, each substituted with substituted with 0-4 R$_5$;

R$_5$ is selected from H, C$_{1-4}$ alkyl substituted with 0-3 R$_e$, F, Cl, Br, =O, CN, NO$_2$, —(CH$_2$)$_r$OR$_b$, —S(O)$_p$R$_c$, —CN, —(CH$_2$)$_r$C(=O)R$_b$, —(CH$_2$)$_r$NR$_a$R$_a$, —(CH$_2$)$_r$C(=O)NR$_a$R$_a$, —(CH$_2$)$_r$NHC(=O)R$_b$, —(CH$_2$)$_r$NHC(=O)OR$_b$, —(CH$_2$)$_r$OC(=O)NR$_a$R$_a$, —(CH$_2$)$_r$NHC(=O)NR$_a$R$_a$, —(CH$_2$)$_r$C(=O)OR$_b$, —(CH$_2$)$_r$S(O)$_2$NR$_a$R$_a$, —(CH$_2$)$_r$NHS(O)$_2$NR$_a$R$_a$, —(CH$_2$)$_r$NHS(O)$_2$R$_c$, (CH$_2$)$_r$-carbocyclyl substituted with 0-3 R$_e$, and —(CH$_2$)$_r$-heterocyclyl substituted with 0-3 R$_e$;

R$_a$, at each occurrence, is independently selected from H, CN, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$; or R$_a$ and R$_a$ together with the nitrogen atom to which they are both attached form a heterocyclic ring substituted with 0-5 R$_e$;

R$_b$, at each occurrence, is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$;

R$_c$, at each occurrence, is independently selected from C$_{1-6}$ alkyl substituted with 0-5 R$_e$, C$_{2-6}$alkenyl substituted with 0-5 R$_e$, C$_{2-6}$alkynyl substituted with 0-5 R$_e$, C$_{3-6}$carbocyclyl, and heterocyclyl;

R$_e$, at each occurrence, is independently selected from C$_{1-6}$ alkyl substituted with 0-5 R$_f$, C$_{2-6}$ alkenyl, C$_{2-6}$ alkynyl, aryl, —(CH$_2$)$_r$—C$_{3-6}$ cycloalkyl, F, Cl, Br, CN, NO$_2$, =O, CO$_2$H, —(CH$_2$)$_r$OR$_f$, SR$_f$, and —(CH$_2$)$_r$NR$_f$R$_f$;

R$_f$, at each occurrence, is independently selected from H, C$_{1-5}$ alkyl, C$_{3-6}$ cycloalkyl, and phenyl, or R$_f$ and R$_f$ together with the nitrogen atom to which they are both attached form a heterocyclic ring optionally substituted with C$_{1-4}$alkyl;

p, at each occurrence, is independently selected from zero, 1, and 2; and r, at each occurrence, is independently selected from zero, 1, 2, 3, and 4.

In another aspect, the present invention provides compounds of Formula (II) or stereoisomers, tautomers, pharmaceutically acceptable salts, solvates, or prodrugs thereof, wherein:

R$_1$ is selected from:

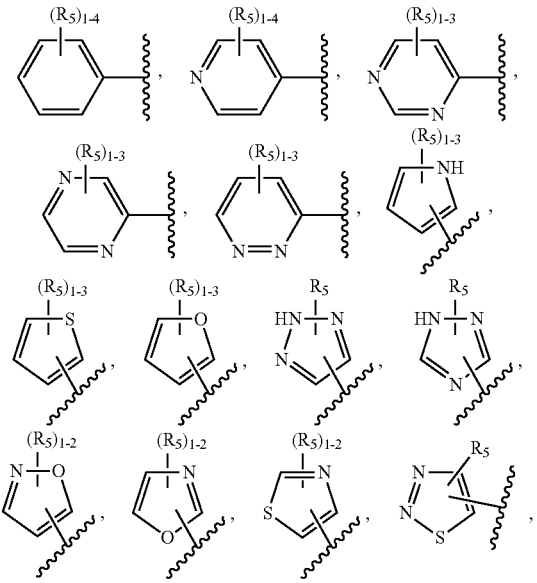

-continued

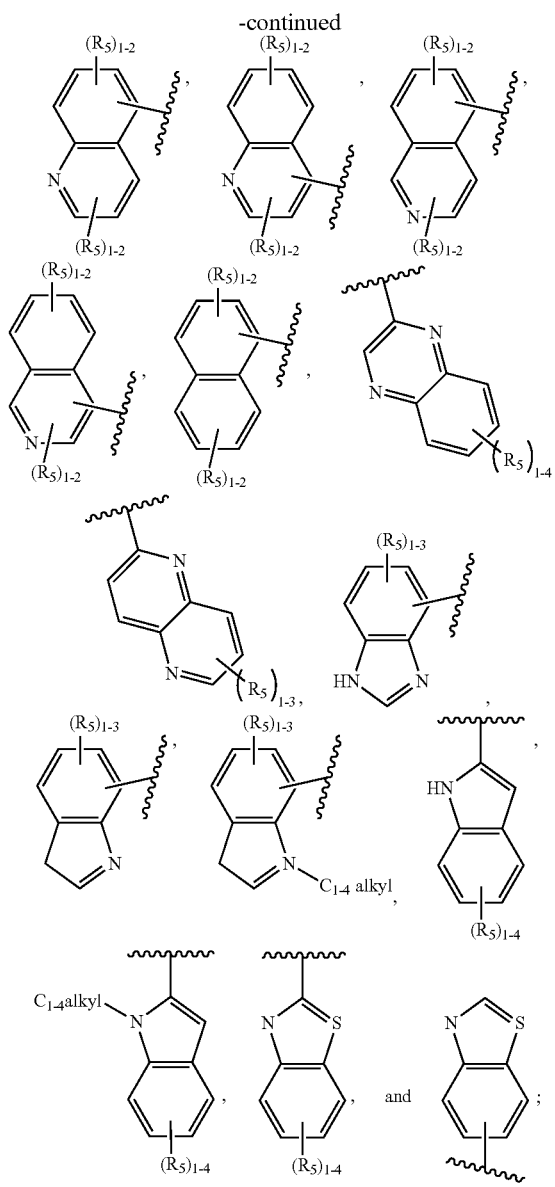

$R_5$ is selected from H, $C_{1-4}$ alkyl substituted with 0-3 $R_e$, F, Cl, Br, =O, CN, $NO_2$, —$(CH_2)_rOR_b$, —$S(O)_pR_c$, —CN, —$(CH_2)_rC(=O)R_b$, —$(CH_2)_rNR_aR_a$, —$(CH_2)_rC(=O)NR_aR_a$, —$(CH_2)_rNHC(=O)R_b$, —$(CH_2)_rNHC(=O)OR_b$, —$(CH_2)_rOC(=O)NR_aR_a$, —$(CH_2)_rNHC(=O)NR_aR_a$, —$(CH_2)_rC(=O)OR_b$, —$(CH_2)_rS(O)_2NR_aR_a$, —$(CH_2)_rNHS(O)_2NR_aR_a$, —$(CH_2)_rNHS(O)_2R_c$, $(CH_2)_r$-aryl substituted with 0-3 $R_e$, and —$(CH_2)_r$-heterocyclyl substituted with 0-3 $R_e$;

$R_a$, at each occurrence, is independently selected from H, CN, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_e$, at each occurrence, is independently selected from $C_{1-6}$ alkyl, $C_{2-6}$ alkenyl, $C_{2-6}$ alkynyl, aryl, —$(CH_2)_r$—$C_{3-6}$ cycloalkyl, F, Cl, Br, CN, $NO_2$, =O, and $CO_2H$;

p, at each occurrence, is independently selected from zero, 1, and 2; and r, at each occurrence, is independently selected from zero, 1, 2, 3, and 4.

In another embodiment there are provided compounds of Formula (II) or stereoisomers, tautomers, pharmaceutically acceptable salts, solvates, or prodrugs thereof, wherein:

L is selected from —$(CR_dR_d)_r$— and —$S(O)_p$—;

$R_2$ is selected from H, $C_{1-2}$ alkyl substituted with 0-3 $R_e$, aryl substituted with 1-5 $R_7$, $C_{3-6}$cycloalkyl substituted with 1-5 $R_7$, and 5- to 12-membered heterocyclyl comprising carbon atoms and 1 to 4 heteroatoms selected from N, O, S, and substituted with 1-5 $R_7$;

$R_7$, at each occurrence, is independently selected from H, F, Cl, Br, =O, CN, $NO_2$, —$OR_b$, —$S(O)_pR_c$, —$C(=O)R_b$, —$(CR_dR_d)_rNR_aR_a$, —$(CR_dR_d)_rC(=O)NR_aR_a$, —$NR_aC(=O)R_b$, —$NR_aC(=O)OR_b$, —$OC(=O)NR_aR_a$, —$NR_aC(=O)NR_aR_a$, —$(CR_dR_d)_rC(=O)OR_b$, —$S(O)_2NR_aR_a$, —$NR_aS(O)_2NR_aR_a$, —$NR_aS(O)_2R_c$, $C_{1-6}$ alkyl substituted with 0-5 $R_e$, —$(C_dR_d)_r$—$C_{3-6}$carbocyclyl substituted with 0-5 $R_e$, and —$(CR_dR_d)_r$-heterocyclyl substituted with 0-5 $R_e$;

$R_a$, at each occurrence, is independently selected from H, CN, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_d$, at each occurrence, is independently selected from H and $C_{1-4}$alkyl substituted with 0-5 $R_e$;

$R_e$, at each occurrence, is independently selected from $C_{1-6}$ alkyl substituted with 0-5 $R_f$, $C_{2-6}$ alkenyl, $C_{2-6}$ alkynyl, aryl, —$(CH_2)_r$—$C_{3-6}$ cycloalkyl, F, Cl, Br, CN, $NO_2$, =O, $CO_2H$, —$(CH_2)_rOR_f$, $SR_f$, and —$(CH_2)_rNR_fR_f$;

$R_f$, at each occurrence, is independently selected from H, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

p, at each occurrence, is independently selected from zero, 1, and 2; and r, at each occurrence, is independently selected from zero, 1, 2, 3, and 4.

In another embodiment there are provided compounds of Formula (II) or stereoisomers, tautomers, pharmaceutically acceptable salts, solvates, or prodrugs thereof, wherein:

$R_2$ is selected from H, $C_{1-6}$ alkyl substituted with 0-3 $R_e$, aryl, $C_{3-6}$cycloalkyl, and 5- to 12-membered heterocyclyl wherein said aryl, cycloalkyl, and heterocycle are selected from:

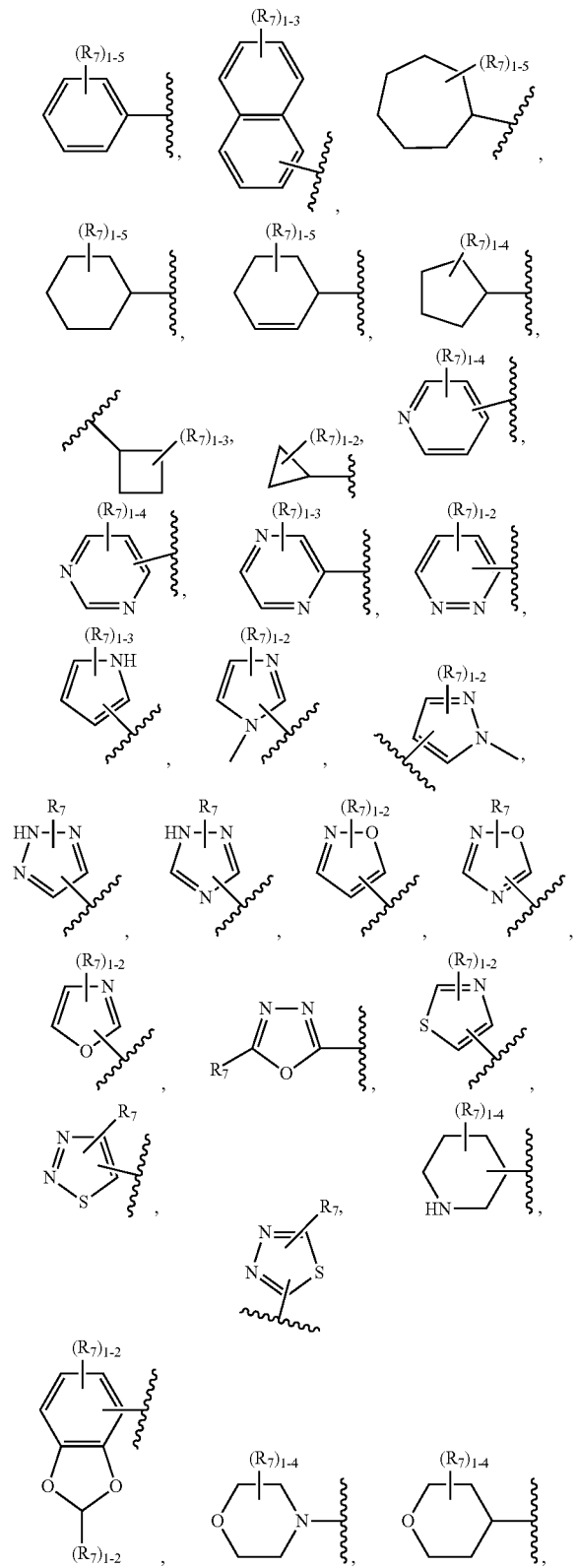

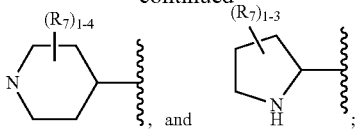

-continued $R_7$, at each occurrence, is independently selected from H, F, Cl, Br, =O, CN, $NO_2$, $-OR_b$, $-S(O)_pR_c$, $-C(=O)R_b$, $-NR_aR_a$, $-C(=O)NR_aR_a$, $-NHC(=O)R_b$, $-NHC(=O)OR_b$, $-OC(=O)NR_aR_a$, $-NHC(=O)NR_aR_a$, $-C(=O)OR_b$, $-S(O)_2NR_aR_a$, $-NHS(O)_2NR_aR_a$, $-NHS(O)_2R_c$, $C_{1-6}$ alkyl substituted with 0-5 $R_e$, $C_{3-6}$ cycloalkyl substituted with 0-5 $R_e$, aryl substituted with 0-5 $R_e$, and heterocyclyl substituted with 0-5 $R_e$;

$R_a$, at each occurrence, is independently selected from H, CN, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $-(CH_2)_r-C_{3-10}$carbocyclyl substituted with 0-5 $R_e$, and $-(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, aryl substituted with 0-5 $R_e$, and heterocyclyl substituted with 0-5 $R_e$;

$R_c$, at each occurrence, is independently selected from $C_{1-6}$ alkyl substituted with 0-5 $R_e$, $C_{3-6}$carbocyclyl, and heterocyclyl;

$R_d$, at each occurrence, is independently selected from H and $C_{1-4}$alkyl; or $R_d$ and $R_d$ together are =O;

$R_e$, at each occurrence, is independently selected from $C_{1-6}$ alkyl, $C_{2-6}$ alkenyl, $C_{2-6}$ alkynyl, aryl, $-(CH_2)_r-C_{3-6}$ cycloalkyl, F, Cl, Br, CN, $NO_2$, =O, and $CO_2H$;

p, at each occurrence, is independently selected from zero, 1, and 2; and r, at each occurrence, is independently selected from zero, 1, 2, and 3.

In another embodiment there are provided compounds of Formula (II) or stereoisomers, tautomers, pharmaceutically acceptable salts, solvates, or prodrugs thereof, wherein:

$L-R_2$ is selected from:

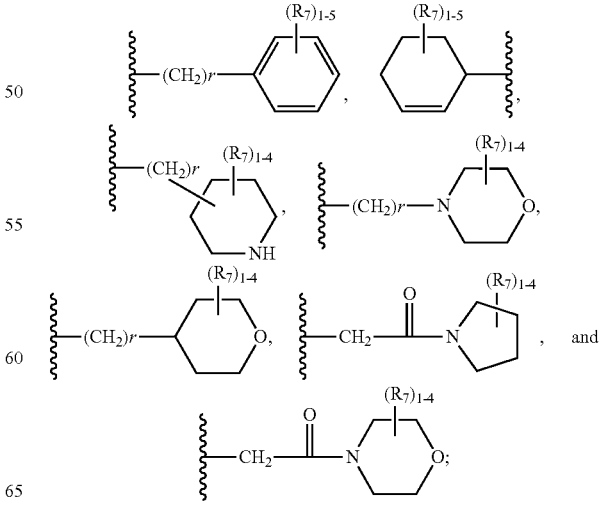

$R_7$, at each occurrence, is independently selected from H, F, Cl, Br, =O, CN, $NO_2$, —$OR_b$, —$S(O)_pR_c$, —C(=O)$R_b$, —$NR_aR_a$, —C(=O)$NR_aR_a$, —NHC(=O)$R_b$, —NHC(=O)$OR_b$, —OC(=O)$NR_aR_a$, —NHC(=O)$NR_aR_a$, —C(=O)$OR_b$, —$S(O)_2NR_aR_a$, —NHS$(O)_2NR_aR_a$, —NHS$(O)_2R_c$, $C_{1-6}$ alkyl substituted with 0-5 $R_e$, aryl substituted with 0-5 $R_e$, and heterocyclyl substituted with 0-5 $R_e$;

$R_a$, at each occurrence, is independently selected from H, CN, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_e$, at each occurrence, is independently selected from $C_{1-6}$ alkyl, $C_{2-6}$ alkenyl, $C_{2-6}$ alkynyl, —$(CH_2)_r$—$C_{3-6}$ cycloalkyl, F, Cl, Br, CN, $NO_2$, =O, and $CO_2H$; and r, at each occurrence, is independently selected from zero, 1, 2, 3, and 4.

In another embodiment there are provided compounds of Formula (II) or stereoisomers, tautomers, pharmaceutically acceptable salts, solvates, or prodrugs thereof, wherein:
$A_1$ is N, $A_2$ is $CR_6$, and $A_3$ is N;
$R_1$ is selected from aryl, pyridyl, pyrimidinyl, pyrazinyl, pyridazinyl, triazinyl, furyl, thienyl, imidazolyl, thiazolyl, indolyl, oxazolyl, isoxazolyl, pyrazolyl, triazolyl, tetrazolyl, indazolyl, 1,2,4-thiadiazolyl, isothiazolyl, quinolinyl, and isoquinolinyl, each substituted with substituted with 0-4 $R_5$;
L-$R_2$ is selected from —$(CR_dR_d)_r$-aryl substituted with 1-5 $R_7$, —$(CR_dR_d)_r$—$C_{3-6}$cycloalkyl substituted with 1-5 $R_7$, and —$(CR_dR_d)_r$-5- to 12-membered heterocyclyl comprising carbon atoms and 1 to 4 heteroatoms selected from N, O, S, and substituted with 1-5 $R_7$;
$R_5$ is selected from H, $C_{1-4}$ alkyl substituted with 0-3 $R_e$, F, Cl, Br, =O, CN, $NO_2$, —$OR_b$, —$S(O)_pR_c$, —CN, —$(CH_2)_rC(=O)R_b$, —$(CH_2)_rNR_aR_a$, —$(CH_2)_rC(=O)NR_aR_a$, —$(CH_2)_rNHC(=O)R_b$, —$(CH_2)_rNHC(=O)OR_b$, —$(CH_2)_rOC(=O)NR_aR_a$, —$(CH_2)_rNHC(=O)NR_aR_a$, —$(CH_2)_rC(=O)OR_b$, —$(CH_2)_rS(O)_2NR_aR_a$, —$(CH_2)_rNHS(O)_2NR_aR_a$, —$(CH_2)_rNHS(O)_2R_c$, $(CH_2)_r$-carbocyclyl substituted with 0-3 $R_e$, and —$(CH_2)_r$-heterocyclyl substituted with 0-3 $R_e$;
$R_6$ is selected from H, F, Cl, Br, $C_{1-4}$ alkyl substituted with 0-3 $R_e$, —CN, —$OR_b$, —$S(O)_pR_c$, —C(=O)$R_b$, —$NR_aR_a$, —C(=O)$NR_aR_a$, —$NR_aC(=O)R_b$, —$NR_aC(=O)OR_b$, —OC(=O)$NR_aR_a$, —$NR_aC(=O)NR_aR_a$, —C(=O)$OR_b$, —$(CH_2)_rS(O)_2NR_aR_a$, —$NR_aS(O)_2NR_aR_a$, —$NR_aS(O)_2R_c$, carbocyclyl substituted with 0-3 $R_e$, and heterocyclyl substituted with 0-3 $R_e$;
$R_7$, at each occurrence, is independently selected from H, F, Cl, Br, =O, CN, $NO_2$, —$OR_b$, —$S(O)_pR_c$, —C(=O)$R_b$, —$(CR_dR_d)_rNR_aR_a$, —$(CR_dR_d)_rC(=O)NR_aR_a$, —$NR_aC(=O)R_b$, —$NR_aC(=O)OR_b$, —OC(=O)$NR_aR_a$, —$NR_aC(=O)NR_aR_a$, —$(CR_dR_d)_rC(=O)OR_b$, —$S(O)_2NR_aR_a$, —$NR_aS(O)_2NR_aR_a$, —$NR_aS(O)_2R_c$, $C_{1-6}$ alkyl substituted with 0-5 $R_e$, —$(CR_dR_d)_r$—$C_{3-6}$carbocyclyl substituted with 0-5 $R_e$, and —$(CR_dR_d)_r$-heterocyclyl substituted with 0-5 $R_e$;
$R_a$, at each occurrence, is independently selected from H, CN, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_d$, at each occurrence, is independently selected from H and $C_{1-4}$alkyl substituted with 0-5 $R_e$;

$R_e$, at each occurrence, is independently selected from $C_{1-6}$ alkyl substituted with 0-5 $R_f$, $C_{2-6}$ alkenyl, $C_{2-6}$ alkynyl, aryl, —$(CH_2)_r$—$C_{3-6}$ cycloalkyl, F, Cl, Br, CN, $NO_2$, =O, $CO_2H$, —$(CH_2)_rOR_f$, $SR_f$, and —$(CH_2)_rNR_fR_f$;

$R_f$, at each occurrence, is independently selected from H, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

p, at each occurrence, is independently selected from zero, 1, and 2; and r, at each occurrence, is independently selected from zero, 1, 2, 3, and 4.

In another embodiment there are provided compounds of Formula (II) or stereoisomers, tautomers, pharmaceutically acceptable salts, solvates, or prodrugs thereof, wherein:
$A_1$ is $CR_6$, $A_2$ is N, and $A_3$ is N;
$R_1$ is selected from aryl, pyridyl, pyrimidinyl, pyrazinyl, pyridazinyl, triazinyl, furyl, thienyl, imidazolyl, thiazolyl, indolyl, oxazolyl, isoxazolyl, pyrazolyl, triazolyl, tetrazolyl, indazolyl, 1,2,4-thiadiazolyl, isothiazolyl, quinolinyl, and isoquinolinyl, each substituted with substituted with 0-4 $R_5$;
L-$R_2$ is selected from —$(CR_dR_d)_r$-aryl substituted with 1-5 $R_7$, —$(CR_dR_d)_r$—$C_{3-6}$cycloalkyl substituted with 1-5 $R_7$, and —$(CR_dR_d)_r$-5- to 12-membered heterocyclyl comprising carbon atoms and 1 to 4 heteroatoms selected from N, O, S, and substituted with 1-5 $R_7$;
$R_5$ is selected from H, $C_{1-4}$ alkyl substituted with 0-3 $R_e$, F, Cl, Br, =O, CN, $NO_2$, —$OR_b$, —$S(O)_pR_c$, —CN, —$(CH_2)_rC(=O)R_b$, —$(CH_2)_rNR_aR_a$, —$(CH_2)_rC(=O)NR_aR_a$, —$(CH_2)_rNHC(=O)R_b$, —$(CH_2)_rNHC(=O)OR_b$, —$(CH_2)_rOC(=O)NR_aR_a$, —$(CH_2)_rNHC(=O)NR_aR_a$, —$(CH_2)_rC(=O)OR_b$, —$(CH_2)_rS(O)_2NR_aR_a$, —$(CH_2)_rNHS(O)_2NR_aR_a$, —$(CH_2)_rNHS(O)_2R_c$, $(CH_2)_r$-carbocyclyl substituted with 0-3 $R_e$, and —$(CH_2)_r$-heterocyclyl substituted with 0-3 $R_e$;
$R_6$ is selected from H, F, Cl, Br, $C_{1-4}$ alkyl substituted with 0-3 $R_e$, —CN, —$OR_b$, —$S(O)_pR_c$, —C(=O)$R_b$, —$NR_aR_a$, —C(=O)$NR_aR_a$, —$NR_aC(=O)R_b$, —$NR_aC(=O)OR_b$, —OC(=O)$NR_aR_a$, —$NR_aC(=O)NR_aR_a$, —C(=O)$OR_b$, —$(CH_2)_rS(O)_2NR_aR_a$, —$NR_aS(O)_2NR_aR_a$, —$NR_aS(O)_2R_c$, carbocyclyl substituted with 0-3 $R_e$, and heterocyclyl substituted with 0-3 $R_e$;
$R_7$, at each occurrence, is independently selected from H, F, Cl, Br, =O, CN, $NO_2$, —$OR_b$, —$S(O)_pR_c$, —C(=O)$R_b$, —$(CR_dR_d)_rNR_aR_a$, —$(CR_dR_d)_rC(=O)NR_aR_a$, —$NR_aC(=O)R_b$, —$NR_aC(=O)OR_b$, —OC(=O)$NR_aR_a$, —$NR_aC(=O)NR_aR_a$, —$(CR_dR_d)_rC(=O)OR_b$, —$S(O)_2NR_aR_a$, —$NR_aS(O)_2NR_aR_a$, —$NR_aS(O)_2R_c$, $C_{1-6}$ alkyl substituted with 0-5 $R_e$, —$(CR_dR_d)_r$—$C_{3-6}$carbocyclyl substituted with 0-5 $R_e$, and —$(CR_dR_d)_r$-heterocyclyl substituted with 0-5 $R_e$;

$R_a$, at each occurrence, is independently selected from H, CN, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_d$, at each occurrence, is independently selected from H and $C_{1-4}$alkyl substituted with 0-5 $R_e$;

$R_e$, at each occurrence, is independently selected from $C_{1-6}$ alkyl substituted with 0-5 $R_f$, $C_{2-6}$ alkenyl, $C_{2-6}$ alkynyl, aryl, —$(CH_2)_r$—$C_{3-6}$ cycloalkyl, F, Cl, Br, CN, $NO_2$, =O, $CO_2H$, —$(CH_2)_rOR_f$, $SR_f$, and —$(CH_2)_rNR_fR_f$;

$R_f$, at each occurrence, is independently selected from H, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

p, at each occurrence, is independently selected from zero, 1, and 2; and r, at each occurrence, is independently selected from zero, 1, 2, 3, and 4.

In another embodiment there are provided compounds according to Formula (III):

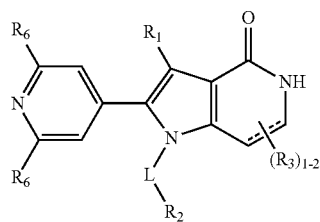

(III)

or stereoisomers, tautomers, pharmaceutically acceptable salts, solvates, or prodrugs thereof, wherein:

--- is an optional bond;

$R_1$ is selected from aryl, pyridyl, pyrimidinyl, pyrazinyl, pyridazinyl, triazinyl, furyl, thienyl, imidazolyl, thiazolyl, indolyl, oxazolyl, isoxazolyl, pyrazolyl, triazolyl, tetrazolyl, indazolyl, 1,2,4-thiadiazolyl, isothiazolyl, quinolinyl, and isoquinolinyl, each substituted with substituted with 0-4 $R_5$;

L is selected from —$(CR_dR_d)_r$— and —$S(O)_p$—;

$R_2$ is selected from H, $C_{1-2}$ alkyl substituted with 0-3 $R_e$, aryl substituted with 1-5 $R_7$, $C_{3-6}$cycloalkyl substituted with 1-5 $R_7$, and 5- to 12-membered heterocyclyl comprising carbon atoms and 1 to 4 heteroatoms selected from N, O, S, and substituted with 1-5 $R_7$;

$R_3$ is selected from H and $C_{1-4}$ alkyl;

$R_5$ is selected from H, $C_{1-4}$ alkyl substituted with 0-3 $R_e$, F, Cl, Br, =O, CN, $NO_2$, —$(CH_2)_rOR_b$, —$S(O)_pR_c$, —CN, —$(CH_2)_rC(=O)R_b$, —$(CH_2)_rNR_aR_a$, —$(CH_2)_rC(=O)NR_aR_a$, —$(CH_2)_rNHC(=O)R_b$, —$(CH_2)_rNHC(=O)$ $OR_b$, —$(CH_2)_rOC(=O)NR_aR_a$, —$(CH_2)_rNHC(=O)$ $NR_aR_a$, —$(CH_2)_rC(=O)OR_b$, —$(CH_2)_rS(O)_2NR_aR_a$, —$(CH_2)_rNHS(O)_2NR_aR_a$, —$(CH_2)_rNHS(O)_2R_c$, $(CH_2)_r$-carbocyclyl substituted with 0-3 $R_e$, and —$(CH_2)_r$-heterocyclyl substituted with 0-3 $R_e$;

$R_6$ is selected from H, F, Cl, Br, $C_{1-4}$ alkyl substituted with 0-3 $R_e$, —CN, —$OR_b$, —$S(O)_pR_c$, —$C(=O)R_b$, —$NR_aR_a$, —$C(=O)NR_aR_a$, —$NR_aC(=O)R_b$, —$NR_aC(=O)OR_b$, —$OC(=O)NR_aR_a$, —$NR_aC(=O)NR_aR_a$, —$C(=O)OR_b$, —$(CH_2)_rS(O)_2NR_aR_a$, —$NR_aS(O)_2$ $NR_aR_a$, —$NR_aS(O)_2R_c$, carbocyclyl substituted with 0-3 $R_e$, and heterocyclyl substituted with 0-3 $R_e$;

$R_7$, at each occurrence, is independently selected from H, F, Cl, Br, =O, CN, $NO_2$, —$OR_b$, —$S(O)_pR_c$, —$C(=O)R_b$, —$(CR_dR_d)_rNR_aR_a$, —$(CR_dR_d)_rC(=O)NR_aR_a$, —$NR_aC(=O)R_b$, —$NR_aC(=O)OR_b$, —$OC(=O)NR_aR_a$, —$NR_aC(=O)NR_aR_a$, —$(CR_dR_d)_rC(=O)OR_b$, —$S(O)_2NR_aR_a$, —$NR_aS(O)_2NR_aR_a$, —$NR_aS(O)_2R_c$, $C_{1-6}$ alkyl substituted with 0-5 $R_e$, —$(CR_dR_d)_r$—$C_{3-6}$carbocyclyl substituted with 0-5 $R_e$, and —$(CR_dR_d)_r$-heterocyclyl substituted with 0-5 $R_e$;

$R_a$, at each occurrence, is independently selected from H, CN, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_d$, at each occurrence, is independently selected from H and $C_{1-4}$alkyl substituted with 0-5 $R_e$;

$R_e$, at each occurrence, is independently selected from $C_{1-6}$ alkyl substituted with 0-5 $R_f$, $C_{2-6}$ alkenyl, $C_{2-6}$ alkynyl, aryl, —$(CH_2)_r$—$C_{3-6}$ cycloalkyl, F, Cl, Br, CN, $NO_2$, =O, $CO_2H$, —$(CH_2)_rOR_f$, $SR_f$, and —$(CH_2)_rNR_fR_f$;

$R_f$, at each occurrence, is independently selected from H, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

p, at each occurrence, is independently selected from zero, 1, and 2; and r, at each occurrence, is independently selected from zero, 1, 2, 3, and 4.

In another embodiment there are provided compounds of Formula (III) or stereoisomers, tautomers, pharmaceutically acceptable salts, solvates, or prodrugs thereof, wherein:

--- is an optional bond;

$R_1$ is selected from:

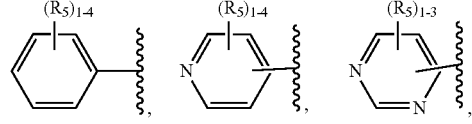

-continued
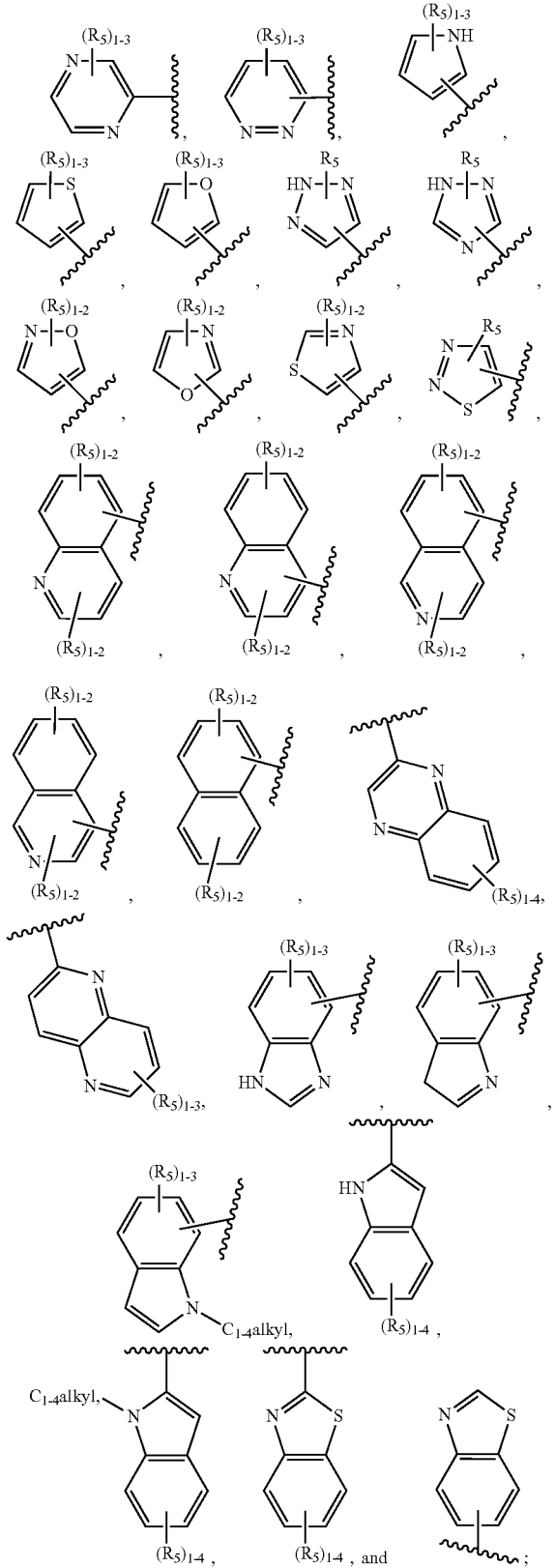
5- to 12-membered heterocyclyl wherein said aryl, cycloalkyl, and heterocycle are selected from:
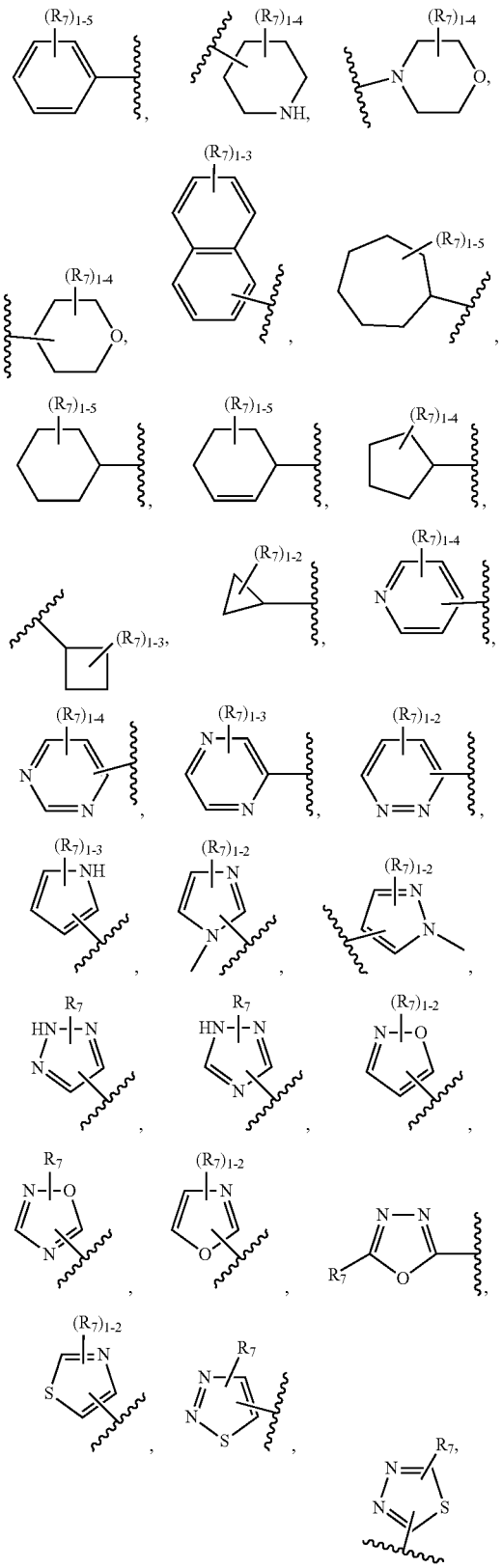
L-R$_2$ is selected from C$_{1-6}$ alkyl substituted with 0-3 R$_e$, —(CR$_d$R$_d$)$_r$-aryl substituted with 1-5 R$_7$, —(CR$_d$R$_d$)$_r$—C$_{3-6}$cycloalkyl substituted with 1-5 R$_7$, and —(CR$_d$R$_d$)$_r$-

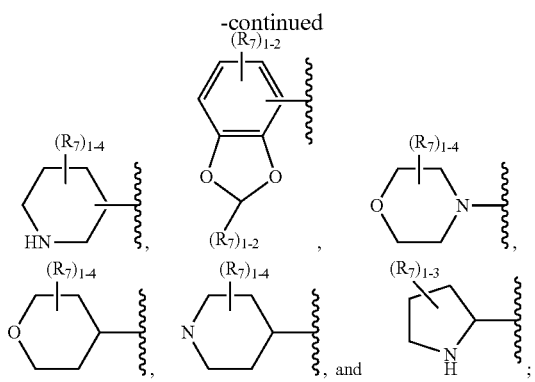

R$_3$ is selected from H and C$_{1-4}$ alkyl;
R$_5$ is selected from H, C$_{1-4}$ alkyl substituted with 0-3 R$_e$, F, Cl, Br, =O, CN, NO$_2$, —(CH$_2$)$_r$OR$_b$, —S(O)$_p$R$_c$, —CN, —OR$_b$, —(CH$_2$)$_r$C(=O)R$_b$, —(CH$_2$)$_r$NR$_a$R$_a$, —(CH$_2$)$_r$C(=O)NR$_a$R$_a$, —(CH$_2$)$_r$NHC(=O)R$_b$, —(CH$_2$)$_r$NHC(=O)OR$_b$, —(CH$_2$)$_r$OC(=O)NR$_a$R$_a$, —(CH$_2$)$_r$NHC(=O)NR$_a$R$_a$, —(CH$_2$)$_r$C(=O)OR$_b$, —(CH$_2$)$_r$S(O)$_2$NR$_a$R$_a$, —(CH$_2$)$_r$NHS(O)$_2$NR$_a$R$_a$, —(CH$_2$)$_r$NHS(O)$_2$R$_c$, (CH$_2$)$_r$-aryl substituted with 0-3 R$_e$, and —(CH$_2$)$_r$-heterocyclyl substituted with 0-3 R$_e$;
R$_6$ is selected from H, F, Cl, Br, C$_{1-4}$ alkyl substituted with 0-3 R$_e$, —CN, —OR$_b$, —NR$_a$R$_a$, —NR$_a$C(=O)R$_b$, —NR$_a$C(=O)OR$_b$, —NR$_a$C(=O)NR$_a$R$_a$, —NR$_a$S(O)$_2$R$_c$, phenyl substituted with 0-3 R$_e$, C$_{3-6}$ cycloalkyl substituted with 0-3 R$_e$, and heterocyclyl substituted with 0-3 R$_e$;
R$_7$, at each occurrence, is independently selected from H, F, Cl, Br, =O, CN, NO$_2$, —OR$_b$, —S(O)$_p$R$_c$, —C(=O)R$_b$, —NR$_a$R$_a$, —C(=O)NR$_a$R$_a$, —NHC(=O)R$_b$, —NHC(=O)OR$_b$, —OC(=O)NR$_a$R$_a$, —NHC(=O)NR$_a$R$_a$, —C(=O)OR$_b$, —S(O)$_2$NR$_a$R$_a$, —NHS(O)$_2$NR$_a$R$_a$, —NHS(O)$_2$R$_c$, C$_{1-6}$ alkyl substituted with 0-5 R$_e$, aryl substituted with 0-5 R$_e$, and heterocyclyl substituted with 0-5 R$_e$;
R$_a$, at each occurrence, is independently selected from H, CN, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$; or R$_a$ and R$_a$ together with the nitrogen atom to which they are both attached form a heterocyclic ring substituted with 0-5 R$_e$;
R$_b$, at each occurrence, is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-6}$ cycloalkyl substituted with 0-5 R$_e$, —(CH$_2$)$_r$-aryl substituted with 0-5 R$_e$, and —(CH$_2$)$_r$-heterocyclyl substituted with 0-5 R$_e$;
R$_c$, at each occurrence, is independently selected from C$_{1-6}$ alkyl substituted with 0-5 R$_e$, C$_{2-6}$alkenyl substituted with 0-5 R$_e$, C$_{2-6}$alkynyl substituted with 0-5 R$_e$, C$_{3-6}$carbocyclyl, and heterocyclyl;
R$_d$, at each occurrence, is independently selected from H and C$_{1-4}$alkyl;
R$_e$, at each occurrence, is independently selected from C$_{1-6}$ alkyl, C$_{2-6}$ alkenyl, C$_{2-6}$ alkynyl, aryl, —(CH$_2$)$_r$—C$_{3-6}$ cycloalkyl, F, Cl, Br, CN, NO$_2$, =O, OH, OC$_{1-4}$ alkyl, and CO$_2$H;
p, at each occurrence, is independently selected from zero, 1, and 2; and
r, at each occurrence, is independently selected from zero, 1, 2, 3, and 4.

In another embodiment there is provided a compound of Formula (III) or stereoisomers, tautomers, pharmaceutically acceptable salts, solvates, or prodrugs thereof, wherein:
--- is an optional bond;
R$_1$ is selected from:

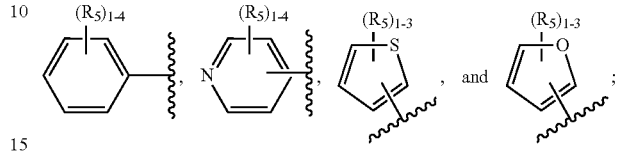

L is selected from —(CR$_d$R$_d$)$_r$— and —S(O)$_p$—;
R$_2$ is selected from H, C$_{1-6}$ alkyl substituted with 0-3 R$_e$, —(CH$_2$)$_r$-aryl substituted with 1-5 R$_7$, —(CH$_2$)$_r$—C$_{3-6}$cycloalkyl substituted with 1-5 R$_7$, and —(CH$_2$)$_r$-5- to 12-membered heterocyclyl wherein said aryl, cycloalkyl, and heterocycle are selected from:

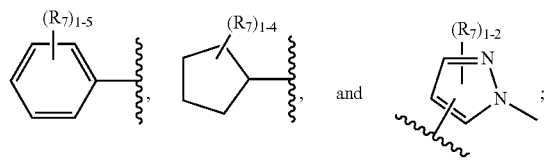

R$_3$ is selected from H and C$_{1-4}$ alkyl;
R$_5$ is selected from H, C$_{1-4}$ alkyl substituted with 0-3 R$_e$, F, Cl, and —(CH$_2$)$_r$OR$_b$;
R$_6$ is selected from H, —NR$_a$R$_a$, and —NR$_a$C(=O)R$_b$;
R$_7$, at each occurrence, is independently selected from H, F, CN, —OR$_b$, C$_{1-6}$ alkyl substituted with 0-5 R$_e$, and heterocyclyl substituted with 0-5 R$_e$;
R$_a$, at each occurrence, is independently selected from H, and C$_{3-10}$carbocyclyl substituted with 0-5 R$_e$;
R$_b$, at each occurrence, is independently selected from H, C$_{1-6}$ alkyl substituted with 0-5 R$_e$, C$_{3-6}$ cycloalkyl substituted with 0-5 R$_e$;
R$_e$, at each occurrence, is independently selected from C$_{1-6}$ alkyl and F; and
r, at each occurrence, is independently selected from zero, 1 and 2.

The present invention is also directed to pharmaceutical compositions useful in treating diseases associated with kinase modulation, including the modulation of receptor interacting protein kinases such as RIPK3, comprising compounds of Formula (I), (II), or (III), or pharmaceutically-acceptable salts thereof, and pharmaceutically-acceptable carriers or diluents.

The invention further relates to methods of treating diseases associated with kinase modulation, including the modulation of receptor interacting protein kinases such as RIPK3, comprising administering to a patient in need of such treatment a therapeutically-effective amount of a compound according to Formula (I), (II) or (III).

The present invention also provides processes and intermediates for making the compounds of the present invention or stereoisomers, tautomers, pharmaceutically acceptable salts, solvates, or prodrugs thereof.

The present invention also provides a method for treating proliferative diseases, allergic diseases, autoimmune diseases and inflammatory diseases, comprising administering to a host in need of such treatment a therapeutically effective amount of at least one of the compounds of the present invention or stereoisomers, tautomers, pharmaceutically acceptable salts, solvates, or prodrugs thereof.

The present invention also provides a method for treating a disease, comprising administering to a patient in need of such treatment a therapeutically-effective amount of a compound of Formula (I), (II), or (III), wherein the disease is IBD or Crohn's disease or ulcerative colitis, systemic lupus erythematosus (SLE), rheumatoid arthritis, multiple sclerosis (MS), or transplant rejection.

The present invention also provides a method of treating a condition comprising administering to a patient in need of such treatment a therapeutically-effective amount of a compound of Formula (I), (II), or (III), wherein the condition is selected from acute myelogenous leukemia, chronic myelogenous leukemia, metastatic melanoma, Kaposi's sarcoma, multiple myeloma, solid tumors, ocular neovasculization, and infantile haemangiomas, B cell lymphoma, systemic lupus erythematosus (SLE), rheumatoid arthritis, psoriatic arthritis, multiple vasculitides, idiopathic thrombocytopenic purpura (ITP), myasthenia gravis, allergic rhinitis, multiple sclerosis (MS), transplant rejection, Type I diabetes, membranous nephritis, inflammatory bowel disease, autoimmune hemolytic anemia, autoimmune thyroiditis, cold and warm agglutinin diseases, Evans syndrome, hemolytic uremic syndrome/thrombotic thrombocytopenic purpura (HUS/TTP), sarcoidosis, Sjögren's syndrome, peripheral neuropathies, pemphigus vulgaris and asthma.

The present invention also provides a method for treating rheumatoid arthritis, comprising administering to a patient in need of such treatment a therapeutically-effective amount of a compound of Formula (I), (II), or (III).

The present invention also provides a method of treating diseases, comprising administering to a patient in need of such treatment a therapeutically-effective amount of a compound of Formula (I), (II), or (III), or pharmaceutically acceptable salt thereof, in combination with other therapeutic agents.

The present invention also provides the compounds of the present invention or stereoisomers, tautomers, pharmaceutically acceptable salts, solvates, or prodrugs thereof, for use in therapy.

In another embodiment, compounds of Formula (I), (II), or (III), are selected from exemplified examples or combinations of exemplified examples or other embodiments herein.

In another embodiment, the $IC_{50}$ value of compounds of Formula (I), (II), or (III) in the RIPK3 assay described below is <10 µM.

In another embodiment, the $IC_{50}$ value of compounds of Formula (I), (II), or (III) in the RIPK3 assay described below is <1 µM.

In another embodiment, the $IC_{50}$ value of compounds of Formula (I), (II), or (III) in the RIPK3 assay described below is <0.01 µM.

The present invention also provides the use of the compounds of the present invention or stereoisomers, tautomers, pharmaceutically acceptable salts, solvates, or prodrugs thereof, for the manufacture of a medicament for the treatment of cancers, an allergic disease, an autoimmune disease or an inflammatory disease.

The present invention may be embodied in other specific forms without departing from the spirit or essential attributes thereof. This invention encompasses all combinations of preferred aspects and/or embodiments of the invention noted herein. It is understood that any and all embodiments of the present invention may be taken in conjunction with any other embodiment or embodiments to describe additional embodiments. It is also to be understood that each individual element of the embodiments is its own independent embodiment. Furthermore, any element of an embodiment is meant to be combined with any and all other elements from any embodiment to describe an additional embodiment.

The following are definitions of terms used in this specification and appended claims. The initial definition provided for a group or term herein applies to that group or term throughout the specification and claims, individually or as part of another group, unless otherwise indicated.

When any variable (e.g., $R^3$) occurs more than one time in any constituent or formula for a compound, its definition at each occurrence is independent of its definition at every other occurrence. Thus, for example, if a group is shown to be substituted with 0-2 $R^3$, then said group may optionally be substituted with up to two $R^3$ groups and $R^3$ at each occurrence is selected independently from the definition of $R^3$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

In cases wherein there are nitrogen atoms (e.g., amines) on compounds of the present invention, these can be converted to N-oxides by treatment with an oxidizing agent (e.g., MCPBA and/or hydrogen peroxides) to afford other compounds of this invention. Thus, all shown and claimed nitrogen atoms are considered to cover both the shown nitrogen and its N-oxide (N→O) derivative.

In accordance with a convention used in the art,

is used in structural formulas herein to depict the bond that is the point of attachment of the moiety or substituent to the core or backbone structure.

A dash "—" that is not between two letters or symbols is used to indicate a point of attachment for a substituent. For example, —$CONH_2$ is attached through the carbon atom.

The term "optionally substituted" in reference to a particular moiety of the compound of Formula (I) (e.g., an optionally substituted heteroaryl group) refers to a moiety having 0, 1, 2, or more substituents. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

As used herein, the term "alkyl" or "alkylene" is intended to include both branched and straight-chain saturated aliphatic hydrocarbon groups having the specified number of carbon atoms. For example, "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$-$C_6$ alkyl" denotes alkyl having 1 to 6 carbon atoms. Alkyl groups can be unsubstituted or substituted so that one or more of its hydrogens are replaced by another chemical group. Example alkyl groups include, but are not limited to, methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like.

When the term "alkyl" is used together with another group, such as in "arylalkyl", this conjunction defines with more specificity at least one of the substituents that the substituted alkyl will contain. For example, "arylalkyl" refers to a substituted alkyl group as defined above where at least one of the substituents is an aryl, such as benzyl. Thus, the term aryl($C_{0-4}$)alkyl includes a substituted lower alkyl having at least one aryl substituent and also includes an aryl directly bonded to another group, i.e., aryl($C_0$)alkyl. The term "heteroarylalkyl" refers to a substituted alkyl group as defined above where at least one of the substituents is a heteroaryl.

"Alkenyl" or "alkenylene" is intended to include hydrocarbon chains of either straight or branched configuration and having one or more double carbon-carbon bonds that may occur in any stable point along the chain. For example, "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, 4-methyl-3-pentenyl, and the like.

"Alkynyl" or "alkynylene" is intended to include hydrocarbon chains of either straight or branched configuration and having one or more triple carbon-carbon bonds that may occur in any stable point along the chain. For example, "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, hexynyl and the like.

When reference is made to a substituted alkenyl, alkynyl, alkylene, alkenylene, or alkynylene group, these groups are substituted with one to three substituents as defined above for substituted alkyl groups.

The term "alkoxy" refers to an oxygen atom substituted by alkyl or substituted alkyl, as defined herein. For example, the term "alkoxy" includes the group —O—$C_{1-6}$alkyl such as methoxy, ethoxy, propoxy, isopropoxy, n-butoxy, sec-butoxy, tert-butoxy, pentoxy, 2-pentyloxy, isopentoxy, neopentoxy, hexoxy, 2-hexoxy, 3-hexoxy, 3-methylpentoxy, and the like. "Lower alkoxy" refers to alkoxy groups having one to four carbons.

It should be understood that the selections for all groups, including, for example, alkoxy, thioalkyl, and aminoalkyl, will be made by one skilled in the field to provide stable compounds.

The term "substituted", as used herein, means that any one or more hydrogens on the designated atom or group is replaced with a selection from the indicated group, provided that the designated atom's normal valence is not exceeded. When a substituent is oxo, or keto (i.e., =O) then 2 hydrogens on the atom are replaced. Keto substituents are not present on aromatic moieties. Unless otherwise specified, substituents are named into the core structure. For example, it is to be understood that when (cycloalkyl)alkyl is listed as a possible substituent, the point of attachment of this substituent to the core structure is in the alkyl portion.

Ring double bonds, as used herein, are double bonds that are formed between two adjacent ring atoms (e.g., C=C, C=N, or N=N).

Combinations of substituents and/or variables are permissible only if such combinations result in stable compounds or useful synthetic intermediates. A stable compound or stable structure is meant to imply a compound that is sufficiently robust to survive isolation from a reaction mixture to a useful degree of purity, and subsequent formulation into an efficacious therapeutic agent. It is preferred that the presently recited compounds do not contain a N-halo, $S(O)_2H$, or $S(O)H$ group.

The term "carbocyclyl" or "carbocyclic" refers to a saturated or unsaturated monocyclic or bicyclic ring in which all atoms of all rings are carbon. Thus, the term includes cycloalkyl and aryl rings. Monocyclic carbocycles have 3 to 6 ring atoms, still more typically 5 or 6 ring atoms. Bicyclic carbocycles have 7 to 12 ring atoms, e.g., arranged as a bicyclo [4,5], [5,5], [5,6] or [6,6] system, or 9 or 10 ring atoms arranged as a bicyclo [5,6] or [6,6] system. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, and phenyl. When the term "carbocycle" is used, it is intended to include "aryl". A bridged ring occurs when one or more carbon atoms link two non-adjacent carbon atoms. Preferred bridges are one or two carbon atoms. It is noted that a bridge always converts a monocyclic ring into a bicyclic ring. When a ring is bridged, the substituents recited for the ring may also be present on the bridge.

The term "aryl" refers to monocyclic or bicyclic aromatic hydrocarbon groups having 6 to 12 carbon atoms in the ring portion, such as phenyl, and naphthyl groups, each of which may be substituted. A preferred aryl group is optionally-substituted phenyl.

The term "cycloalkyl" refers to cyclized alkyl groups, including mono-, bi- or poly-cyclic ring systems. $C_{3-7}$ cycloalkyl is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, norbornyl, and the like, which optionally may be substituted at any available atoms of the ring(s).

The terms "heterocycloalkyl", "heterocyclo", "heterocyclic", or "heterocyclyl" may be used interchangeably and refer to substituted and unsubstituted non-aromatic 3- to 7-membered monocyclic groups, 7- to 11-membered bicyclic groups, and 10- to 15-membered tricyclic groups, in which at least one of the rings has at least one heteroatom (O, S or N), said heteroatom containing ring preferably having 1, 2, or 3 heteroatoms selected from O, S, and N. Each ring of such a group containing a heteroatom can contain one or two oxygen or sulfur atoms and/or from one to four nitrogen atoms provided that the total number of heteroatoms in each ring is four or less, and further provided that the ring contains at least one carbon atom. The nitrogen and sulfur atoms may optionally be oxidized and the nitrogen atoms may optionally be quaternized. The fused rings completing the bicyclic and tricyclic groups may contain only carbon atoms and may be saturated, partially saturated, or unsaturated. The heterocyclo group may be attached at any available nitrogen or carbon atom. The term "heterocycle" includes "heteroaryl" groups. As valence allows, if said further ring is cycloalkyl or heterocyclo it is additionally optionally substituted with =O (oxo).

Exemplary monocyclic heterocyclyl groups include azetidinyl, pyrrolidinyl, oxetanyl, imidazolinyl, oxazolidinyl, isoxazolinyl, thiazolidinyl, isothiazolidinyl, tetrahydrofuranyl, piperidyl, piperazinyl, 2-oxopiperazinyl, 2-oxopiperidyl, 2-oxopyrrolodinyl, 2-oxoazepinyl, azepinyl, 1-pyridonyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl and the like. Exemplary bicyclic heterocyclo groups include quinuclidinyl.

The term "heteroaryl" refers to substituted and unsubstituted aromatic 5- or 6-membered monocyclic groups, 9- or 10-membered bicyclic groups, and 11- to 14-membered tricyclic groups which have at least one heteroatom (O, S or N) in at least one of the rings, said heteroatom-containing ring preferably having 1, 2, or 3 heteroatoms selected from O, S, and N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. As valence allows, if said further ring is cycloalkyl or heterocyclo it is additionally optionally substituted with =O (oxo).

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, tetrahydroquinolinyl, and the like.

Exemplary tricyclic heteroaryl groups include carbazolyl, benzindolyl, phenanthrollinyl, acridinyl, phenanthridinyl, xanthenyl and the like.

Unless otherwise indicated, when reference is made to a specifically-named aryl (e.g., phenyl), cycloalkyl (e.g., cyclohexyl), heterocyclo (e.g., pyrrolidinyl, piperidinyl, and morpholinyl) or heteroaryl (e.g., tetrazolyl, imidazolyl, pyrazolyl, triazolyl, thiazolyl, and furyl) the reference is intended to include rings having 0 to 3, preferably 0-2, substituents selected from those recited above for the aryl, cycloalkyl, heterocyclo and/or heteroaryl groups, as appropriate.

The term "halo" or "halogen" refers to chloro, bromo, fluoro and iodo.

The term "haloalkyl" means a substituted alkyl having one or more halo substituents. For example, "haloalkyl" includes mono, bi, and trifluoromethyl.

The term "haloalkoxy" means an alkoxy group having one or more halo substituents. For example, "haloalkoxy" includes OCF$_3$.

The term "heteroatoms" shall include oxygen, sulfur and nitrogen.

When the term "unsaturated" is used herein to refer to a ring or group, the ring or group may be fully unsaturated or partially unsaturated.

One skilled in the field will understand that, when the designation "CO$_2$" is used herein, this is intended to refer to the group

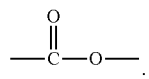

Throughout the specification, groups and substituents thereof may be chosen by one skilled in the field to provide stable moieties and compounds and compounds useful as pharmaceutically-acceptable compounds and/or intermediate compounds useful in making pharmaceutically-acceptable compounds.

The compounds of Formula (I) may exist in a free form (with no ionization) or can form salts which are also within the scope of this invention. Unless otherwise indicated, reference to an inventive compound is understood to include reference to the free form and to salts thereof. The term "salt(s)" denotes acidic and/or basic salts formed with inorganic and/or organic acids and bases. In addition, the term "salt(s)" may include zwitterions (inner salts), e.g., when a compound of Formula (I), contains both a basic moiety, such as an amine or a pyridine or imidazole ring, and an acidic moiety, such as a carboxylic acid. Pharmaceutically acceptable (i.e., non-toxic, physiologically acceptable) salts are preferred, such as, for example, acceptable metal and amine salts in which the cation does not contribute significantly to the toxicity or biological activity of the salt. However, other salts may be useful, e.g., in isolation or purification steps which may be employed during preparation, and thus, are contemplated within the scope of the invention. Salts of the compounds of the Formula (I) may be formed, for example, by reacting a compound of the Formula (I) with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-β-phenethylamine, 1-ephenamine, N,N'-dibenzylethylenediamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Preferred salts include monohydrochloride, hydrogensulfate, methanesulfonate, phosphate or nitrate salts.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 18th Edition, Mack Publishing Company, Easton, Pa. (1990), the disclosure of which is hereby incorporated by reference.

All stereoisomers of the compounds of the instant invention are contemplated, either in admixture or in pure or substantially pure form. Stereoisomers may include compounds which are optical isomers through possession of one or more chiral atoms, as well as compounds which are optical isomers by virtue of limited rotation about one or more bonds (atropisomers). The definition of compounds according to the invention embraces all the possible stereoisomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Prodrugs and solvates of the inventive compounds are also contemplated. The term "prodrug" denotes a compound which, upon administration to a subject, undergoes chemical conversion by metabolic or chemical processes to yield a compound of the Formula (I), and/or a salt and/or solvate thereof. Any compound that will be converted in vivo to provide the bioactive agent (i.e., the compound for Formula (I)) is a prodrug within the scope and spirit of the invention. For example, compounds containing a carboxy group can form physiologically hydrolyzable esters which serve as prodrugs by being hydrolyzed in the body to yield Formula (I) compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of Formula (I) include $C_{1-6}$alkylbenzyl, 4-methoxybenzyl, indanyl, phthalyl, methoxymethyl, $C_{1-6}$alkanoyloxy-$C_{1-6}$alkyl, e.g., acetoxymethyl, pivaloyloxymethyl or propionyloxymethyl, $C_{1-6}$alkoxycarbonyloxy-$C_{1-6}$alkyl, e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl and other well-known physiologically hydrolyzable esters used, for example, in the penicillin and cephalosporin arts. Such esters may be prepared by conventional techniques known in the art.

Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology*, 112:309-396, Academic Press (1985);

b) Bundgaard, H., Chapter 5: "Design and Application of Prodrugs", *A Textbook of Drug Design and Development*, pp. 113-191, Krogsgaard-Larsen, P. et al., eds., Harwood Academic Publishers (1991); and c) Bundgaard, H., *Adv. Drug Deliv. Rev.,* 8:1-38 (1992), each of which is incorporated herein by reference.

Compounds of the Formula (I) and salts thereof may exist in their tautomeric form, in which hydrogen atoms are transposed to other parts of the molecules and the chemical bonds between the atoms of the molecules are consequently rearranged. It should be understood that the all tautomeric forms, insofar as they may exist, are included within the invention.

Compounds of this invention may have one or more asymmetric centers. Unless otherwise indicated, all chiral (enantiomeric and diastereomeric) and racemic forms of compounds of the present invention are included in the present invention. Many geometric isomers of olefins, C=N double bonds, and the like can also be present in the compounds, and all such stable isomers are contemplated in the present invention. Cis and trans geometric isomers of the compounds of the present invention are described and may be isolated as a mixture of isomers or as separated isomeric forms. The present compounds can be isolated in optically active or racemic forms. It is well known in the art how to prepare optically active forms, such as by resolution of racemic forms or by synthesis from optically active starting materials. All chiral, (enantiomeric and diastereomeric) and racemic forms and all geometric isomeric forms of a structure are intended, unless the specific stereochemistry or isomer form is specifically indicated. All geometric isomers, tautomers, atropisomers, hydrates, solvates, polymorphs, and isotopically labeled forms of the compounds referred to herein, and mixtures thereof, are considered within the scope of the present invention. Methods of solvation are generally known in the art.

Utility

The compounds of the invention modulate kinase activity, including the modulation of RIPK3. Accordingly, compounds of Formula (I), (II), or (III) have utility in treating conditions associated with the modulation of kinase activity, and particularly the selective inhibition of RIPK3 activity. In another embodiment, compounds of Formula (I), (II), or (III) have advantageous selectivity for RIPK3 activity preferably from at least 20 fold to over 1,000 fold more selective.

As used herein, the terms "treating" or "treatment" encompass the treatment of a disease state in a mammal, particularly in a human, and include: (a) preventing or delaying the occurrence of the disease state in a mammal, in particular, when such mammal is predisposed to the disease state but has not yet been diagnosed as having it; (b) inhibiting the disease state, i.e., arresting its development; and/or (c) achieving a full or partial reduction of the symptoms or disease state, and/or alleviating, ameliorating, lessening, or curing the disease or disorder and/or its symptoms.

In view of their activity as selective inhibitors of RIPK3, compounds of Formula (I), (II), or (III) are useful in treating RIPK3-associated conditions including, but not limited to, inflammatory diseases such as Crohn's and ulcerative colitis, asthma, graft versus host disease, chronic obstructive pulmonary disease; autoimmune diseases such as Graves' disease, rheumatoid arthritis, systemic lupus erythematosis, psoriasis; destructive bone disorders such as bone resorption disease, osteoarthritis, osteoporosis, multiple myeloma-related bone disorder; proliferative disorders such as acute myelogenous leukemia, chronic myelogenous leukemia; angiogenic disorders such as angiogenic disorders including solid tumors, ocular neovasculization, and infantile haemangiomas; infectious diseases such as sepsis, septic shock, and Shigellosis; neurodegenerative diseases such as Alzheimer's disease, Parkinson's disease, cerebral ischemias or neurodegenerative disease caused by traumatic injury, oncologic and viral diseases such as metastatic melanoma, Kaposi's sarcoma, multiple myeloma, and HIV infection and CMV retinitis, AIDS, respectively.

More particularly, the specific conditions or diseases that may be treated with the inventive compounds include, without limitation, pancreatitis (acute or chronic), asthma, allergies, adult respiratory distress syndrome, chronic obstructive pulmonary disease, glomerulonephritis, rheumatoid arthritis, systemic lupus erythematosis, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs. host disease, inflammatory reaction induced by endotoxin, tuberculosis, atherosclerosis, muscle degeneration, cachexia, psoriatic arthritis, Reiter's syndrome, gout, traumatic arthritis, rubella arthritis, acute synovitis, pancreatic β-cell disease; diseases characterized by massive neutrophil infiltration; rheumatoid spondylitis, gouty arthritis and other arthritic conditions, cerebral malaria, chronic pulmonary inflammatory disease, silicosis, pulmonary sarcoidosis, bone resorption disease, allograft rejections, fever and myalgias due to infection, cachexia secondary to infection, meloid formation, scar tissue formation, ulcerative colitis, pyresis, influenza, osteoporosis, osteoarthritis, acute myelogenous leukemia, chronic myelogenous leukemia, metastatic melanoma, Kaposi's sarcoma, multiple myeloma, sepsis, septic shock, and Shigellosis; Alzheimer's disease, Parkinson's disease, cerebral ischemias or neurodegenerative disease caused by traumatic injury; angiogenic disorders including solid tumors, ocular neovasculization, and infantile haemangiomas; viral diseases including acute hepatitis infection (including hepatitis A, hepatitis B and hepatitis C), HIV infection and CMV retinitis, AIDS, ARC or malignancy, and herpes; stroke, myocardial ischemia, ischemia in stroke heart attacks, organ hyposia, vascular hyperplasia, cardiac and renal reperfusion injury, thrombosis, cardiac hypertrophy, thrombin-induced platelet aggregation, endotoxemia and/or toxic shock syndrome, conditions associated with prostaglandin endoperoxidase syndase-2, and pemphigus vulgaris. Preferred methods of treatment are those wherein the condition is selected from Crohn's and ulcerative colitis, allograft rejection, rheumatoid arthritis, psoriasis, ankylosing spondylitis, psoriatic arthritis, and pemphigus vulgaris. Alternatively preferred methods of treatment are those wherein the condition is selected from ischemia reperfusion injury, including cerebral ischemia reperfusions injury arising from stroke and cardiac ischemia reperfusion injury arising from myocardial infarction.

When the terms "RIPK3-associated condition" or "RIPK3-associated disease or disorder" are used herein, each is intended to encompass all of the conditions identified above as if repeated at length, as well as any other condition that is affected by RIPK3 kinase activity.

The present invention thus provides methods for treating such conditions, comprising administering to a subject in need thereof a therapeutically-effective amount of at least one compound of Formula (I) or a salt thereof "Therapeutically effective amount" is intended to include an amount of a compound of the present invention that is effective when administered alone or in combination to inhibit RIPK3.

The methods of treating RIPK3 kinase-associated conditions may comprise administering compounds of Formula (I) alone or in combination with each other and/or other suitable therapeutic agents useful in treating such conditions. Accordingly, "therapeutically effective amount" is also intended to include an amount of the combination of compounds claimed that is effective to inhibit RIPK3 and/or treat diseases associated with RIPK3.

Exemplary of such other therapeutic agents include corticosteroids, rolipram, calphostin, cytokine-suppressive antiinflammatory drugs (CSAIDs), Interleukin-10, glucocorticoids, salicylates, nitric oxide, and other immunosuppressants; nuclear translocation inhibitors, such as deoxyspergualin (DSG); non-steroidal antiinflammatory drugs (NSAIDs) such as ibuprofen, celecoxib and rofecoxib; steroids such as prednisone or dexamethasone; antiviral agents such as abacavir; antiproliferative agents such as methotrexate, leflunomide, FK506 (tacrolimus, PROGRAF®); cytotoxic drugs such as azathiprine and cyclophosphamide; TNF-α inhibitors such as tenidap, anti-TNF antibodies or soluble TNF receptor, and rapamycin (sirolimus or RAPAMUNE®) or derivatives thereof.

The above other therapeutic agents, when employed in combination with the compounds of the present invention, may be used, for example, in those amounts indicated in the *Physicians' Desk Reference* (PDR) or as otherwise determined by one of ordinary skill in the art. In the methods of the present invention, such other therapeutic agent(s) may be administered prior to, simultaneously with, or following the administration of the inventive compounds. The present invention also provides pharmaceutical compositions capable of treating RIPK3 kinase-associated conditions, including IL-1, IL-6, IL-8, IFNγ and TNF-α-mediated conditions, as described above.

The inventive compositions may contain other therapeutic agents as described above and may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

Accordingly, the present invention further includes compositions comprising one or more compounds of Formula (I) and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include without limitation the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 17th Edition (1985), which is incorporated herein by reference in its entirety.

The compounds of Formula (I), (II), or (III) may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; buccally; parenterally, such as by subcutaneous, intravenous, intramuscular or intrasternal injection or infusion techniques (e.g., as sterile injectable aq. or non-aq. solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for topical administration include a topical carrier such as PLASTIBASE® (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may also be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (e.g., CARBOPOL 934®). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The therapeutically-effective amount of a compound of the present invention may be determined by one of ordinary skill in the art, and includes exemplary dosage amounts for a mammal of from about 0.05 to 1000 mg/kg; 1-1000 mg/kg; 1-50 mg/kg; 5-250 mg/kg; 250-1000 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, horses, and the like. Thus, when the term "patient" is used herein, this term is intended to include all subjects, most preferably mammalian species, that are affected by mediation of RIPK3 enzyme levels.

RIPK3 HTRF Kinase Assay

The assays were performed in black 1536-well plates. The final assay volume of 2 μl contained a mixture of a fluorescently labeled HTRF probe, Terbium (Tb) labeled anti-GST antibody, RIPK3, and test compounds in assay buffer (20 mM HEPES pH 7.4, 10 mM $MgCl_2$, 0.015% Brij35, 4 mM DTT, and 50 μg/mL BSA). The reaction was incubated at room temperature for 60 min. and was analyzed on an Envision plate reader.

Inhibition data were calculated by comparison to background control reactions for 100% inhibition and vehicle-only reactions for 0% inhibition. The final concentration of reagents in the assay is RIPK3, 1 nM; HTRF probe, 23 nM; 0.2 nM Tb anti-GST; and DMSO, 0.5%. Dose response curves were generated to determine the concentration required inhibiting 50% of kinase activity ($IC_{50}$). Compounds were dissolved at 10 mM in dimethylsulfoxide (DMSO) and evaluated at seven concentrations, in singlet. $IC_{50}$ values were derived by non-linear regression analysis.

Using this assay, the $IC_{50}$ values of the following compounds were determined. See Table A. $IC_{50}$ ranges against RIPK3 are as follows:

TABLE A

| Example No. | $IC_{50}$ for Inhibition of RIPK3, nM |
| --- | --- |
| 1 | + |
| 2 | +++ |
| 3 | + |
| 4 | +++ |
| 5 | + |
| 6 | + |
| 7 | + |
| 8 | +++ |
| 9 | ++ |
| 10 | + |
| 11 | + |
| 12 | + |
| 13 | +++ |
| 14 | +++ |
| 15 | ++ |
| 16 | + |
| 17 | + |
| 18 | + |
| 19 | + |
| 20 | ++ |
| 21 | + |
| 22 | + |
| 23 | + |
| 24 | + |
| 25 | + |

TABLE A-continued

| Example No. | $IC_{50}$ for Inhibition of RIPK3, nM |
| --- | --- |
| 26 | + |
| 27 | +++ |
| 28 | ++ |
| 29 | ++ |
| 30 | + |
| 31 | + |
| 32 | + |
| 33 | ++ |
| 34 | +++ |
| 35 | ++ |
| 36 | + |
| 37 | + |
| 38 | +++ |
| 39 | + |
| 40 | + |
| 41 | +++ |
| 42 | + |
| 43 | +++ |
| 44 | +++ |
| 45 | ++ |
| 46 | +++ |
| 47 | + |
| 48 | +++ |
| 49 | + |
| 50 | + |
| 51 | +++ |
| 52 | ++ |
| 53 | +++ |
| 54 | ++ |
| 55 | +++ |
| 56 | + |
| 57 | ++ |
| 58 | ++ |
| 59 | + |
| 60 | ++ |
| 61 | + |
| 62 | + |
| 63 | + |
| 64 | +++ |
| 65 | +++ |
| 66 | +++ |
| 67 | ++ |
| 68 | +++ |
| 69 | ++ |
| 70 | ++ |
| 71 | +++ |
| 72 | + |
| 73 | +++ |
| 74 | +++ |
| 75 | +++ |
| 76 | + |
| 77 | +++ |
| 78 | +++ |
| 79 | ++ |
| 80 | + |
| 81 | ++ |
| 82 | + |
| 83 | + |
| 84 | +++ |
| 85 | + |
| 86 | + |
| 87 | ++ |
| 88 | + |
| 89 | + |
| 90 | + |
| 91 | + |
| 92 | + |
| 93 | + |
| 94 | + |
| 95 | ++ |
| 96 | + |
| 97 | + |
| 98 | + |
| 99 | ++ |
| 100 | +++ |
| 101 | +++ |
| 102 | + |
| 103 | + |

TABLE A-continued

| Example No. | IC$_{50}$ for Inhibition of RIPK3, nM |
| --- | --- |
| 104 | + |
| 105 | + |
| 106 | + |
| 107 | + |
| 108 | + |
| 109 | + |
| 110 | + |
| 111 | + |
| 112 | + |
| 113 | + |
| 114 | ++ |
| 115 | +++ |
| 116 | + |
| 117 | ++ |
| 118 | ++ |
| 119 | ++ |
| 120 | + |
| 121 | ++ |
| 122 | + |
| 123 | +++ |
| 124 | +++ |
| 125 | + |
| 126 | + |
| 127 | +++ |
| 128 | +++ |
| 129 | ++ |
| 130 | +++ |
| 131 | + |
| 132 | + |
| 133 | + |
| 134 | +++ |
| 135 | + |
| 136 | +++ |
| 137 | +++ |
| 138 | +++ |
| 139 | ++ |
| 140 | +++ |
| 141 | +++ |
| 142 | +++ |
| 143 | + |
| 144 | +++ |
| 145 | ++ |
| 146 | ++ |
| 147 | + |
| 148 | + |
| 149 | ++ |
| 150 | ++ |
| 151 | +++ |
| 152 | + |
| 153 | +++ |
| 154 | + |
| 155 | + |
| 156 | +++ |
| 157 | +++ |
| 158 | ++ |
| 159 | +++ |
| 160 | +++ |
| 161 | +++ |
| 162 | + |
| 163 | ++ |
| 164 | +++ |
| 165 | + |
| 166 | + |
| 167 | + |
| 168 | + |
| 169 | + |
| 170 | + |
| 171 | ++ |
| 172 | + |
| 173 | + |
| 174 | + |
| 175 | + |
| 176 | + |
| 177 | + |
| 178 | + |
| 179 | + |
| 180 | + |
| 181 | + |

TABLE A-continued

| Example No. | IC$_{50}$ for Inhibition of RIPK3, nM |
| --- | --- |
| 182 | ++ |
| 183 | +++ |
| 184 | + |
| 185 | + |

+++ = 0-30 nM;
++ = 31-100 nM;
+ = 100-15000 nM.

Methods of Preparation

Compounds of Formula (I), and intermediates used in the preparation of compounds of Formula (I), can be prepared using procedures shown in the following Examples and related procedures. The methods and conditions used in these examples, and the actual compounds prepared in these examples, are not meant to be limiting, but are meant to demonstrate how the compounds of Formula (I) can be prepared. Starting materials and reagents used in these examples, when not prepared by a procedure described herein, are generally either commercially available, or are reported in the chemical literature, or may be prepared by using procedures described in the chemical literature.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "min" for minute or minutes, "h" for hour or hours, "rt" for room temperature, "ON" for overnight, "RT" for retention time, "atm" for atmosphere, "psi" for pounds per square inch, "conc." for concentrate, "sat" or "saturated" for saturated, "CVs" for column volumes, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "the" for thin layer chromatography, "NMR" for nuclear magnetic resonance spectroscopy, "nOe" for nuclear Overhauser effect spectroscopy, "$^1$H" for proton, "δ" for delta, "s" for singlet, "d" for doublet, "t" for triplet, "q" for quartet, "m" for multiplet, "br" for broad, "MHz" for megahertz, and "α", "β", "R", "S", "E", and "Z" are stereochemical designations familiar to one skilled in the art.

Me methyl
Et ethyl
Pr propyl
i-Pr isopropyl
Bu butyl
i-Bu isobutyl
t-Bu tert-butyl
Ph phenyl
Bn benzyl
Boc tert-butyloxycarbonyl
AcOH or HOAc acetic acid
Boc (tert-butoxy)carbonyl
BOP reagent benzotriazol-1-yloxytris(dimethylamino)phosphonium hexafluorophosphate
CBz carbobenzyloxy CH₂Cl₂ dichloromethane
CH₃CN or ACN acetonitrile
CDCl₃ deutero-chloroform
CHCl₃ chloroform
Cs₂CO₃ cesium carbonate
Cu(OAc)₂ copper (II) acetate
DBU 1,8-diazabicyclo[5.4.0]undec-7-ene
DCE 1,2 dichloroethane
DCM dichloromethane
DDQ 2,3-dichloro-5,6-dicyano-1,4-benzoquinone
DEA diethylamine
DIEA, DIPEA or Hunig's base diisopropylethylamine
DMAP 4-dimethylaminopyridine
DME 1,2-dimethoxyethane
DMF dimethyl formamide
DMSO dimethyl sulfoxide
Dppp (R)-(+)-1,2-bis(diphenylphosphino)propane
DuPhos (+)-1,2-bis((2S,5S)-2,5-diethylphospholano)benzene
EDC N-(3-dimthylaminopropyl)-N'-ethylcarbodiimide
EDCI N-(3-dimthylaminopropyl)-N'-ethylcarbodiimide hydrochloride
(S,S)-EtDuPhosRh(I) (+)-1,2-bis((2S,5S)-2,5-diethylphospholano)benzene(1,5-cyclooctadiene)rhodium(I) trifluoromethanesulfonate
Et₃N or TEA triethylamine
EtOAc ethyl acetate
Et₂O diethyl ether
EtOH ethanol
HCl hydrochloric acid
HATU O-(7-azabenzotriazol-1-yl)-N,N,N',N'-tetramethyluronium hexafluorophosphate
Hex hexane
HOBt or HOBT 1-hydroxybenzotriazole
H₂SO₄ sulfuric acid
K₂CO₃ potassium carbonate
KOAc potassium acetate
K₃PO₄ potassium phosphate
LAH lithium aluminum hydride
LG leaving group
LiOH lithium hydroxide
MeOH methanol
MeI iodomethane
MgSO₄ magnesium sulfate
NaCl sodium chloride
NaH sodium hydride
NaHCO₃ sodium bicarbonate
Na₂CO₃ sodium carbonate
NaOH sodium hydroxide
Na₂SO₃ sodium sulfite
Na₂SO₄ sodium sulfate
NBS N-bromosuccinimide
NCS N-chlorosuccinimide
NH₃ ammonia
NH₄Cl ammonium chloride
NH₄OH ammonium hydroxide
OTf triflate or trifluoromethanesulfonate
Pd₂(dba)₃ tris(dibenzylideneacetone)dipalladium(O)
Pd(OAc)₂ palladium(II) acetate
Pd/C palladium on carbon
Pd(dppf)Cl₂ [1,1'-bis(diphenylphosphino)-ferroceneldichloropalladium(II)
Ph3PCl₂ triphenylphosphine dichloride
PG protecting group
POCl₃ phosphorus oxychloride
i-PrOH or IPA isopropanol
SEM-Cl 2-(trimethysilyl)ethoxymethyl chloride
SiO₂ silica oxide
SnCl₂ tin(II) chloride
TBAI tetra-n-butylammonium iodide
TFA trifluoroacetic acid
THF tetrahydrofuran
T3P® propane phosphonic acid anhydride
Xantphos 4,5-bis(diphenylphosphino)-9,9-dimethylxanthene Examples of compounds of the present invention prepared by methods described in the general schemes are given in the intermediates and examples section set out hereinafter. Example compounds are typically prepared as racemic mixtures. Preparation of homochiral examples may be carried out by techniques known to one skilled in the art. For example, homochiral compounds may be prepared by separation of racemic products by chiral phase preparative HPLC. Alternatively, the example compounds may be prepared by methods known to give enantiomerically enriched products. These include, but are not limited to, the incorporation of chiral auxiliary functionalities into racemic intermediates which serve to control the diastereoselectivity of transformations, providing enantio-enriched products upon cleavage of the chiral auxiliary.

Scheme 1 illustrates an approach to the synthesis of compounds exemplified by 4. Pyrrole 1 can be prepared by cyclization of an alpha amino ketone and piperidine-2,4-dione. Halogenation of the pyrrole, followed by alkylation of the pyrrole using conditions listed or alternative appropriate conditions known to those in the art of organic synthesis would yield pyrrole 3. Functionalization of intermediate 3 can be achieved through a Suzuki coupling reaction (Miyaura, N. et al., *Chem. Rev.,* 95:2457-2483 (1995)) to provide compounds of the type exemplified by 4. Appropriate functionalization of intermediates used in this invention to prepare compounds similar to 4 can be achieved through the Suzuki reaction, Stille reaction or simple reactions known to those in the art.

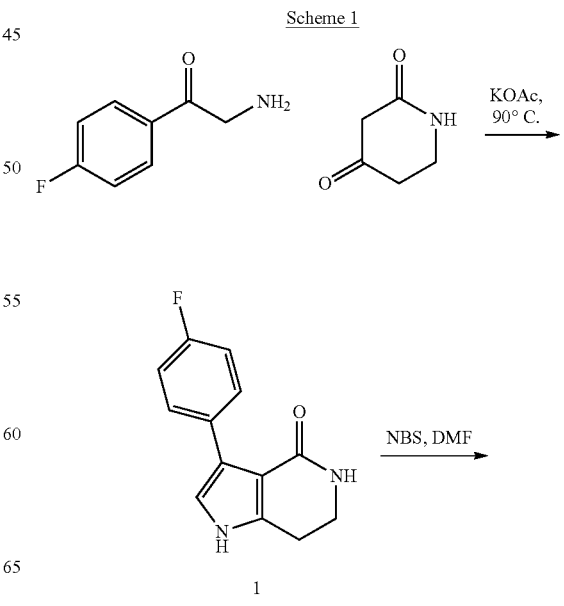

Scheme 1

-continued

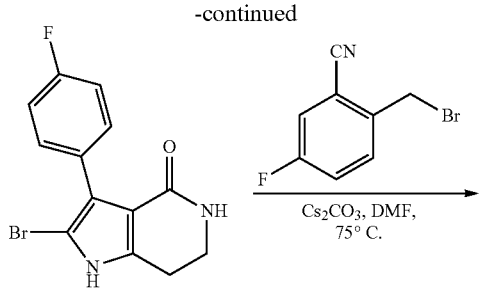

2

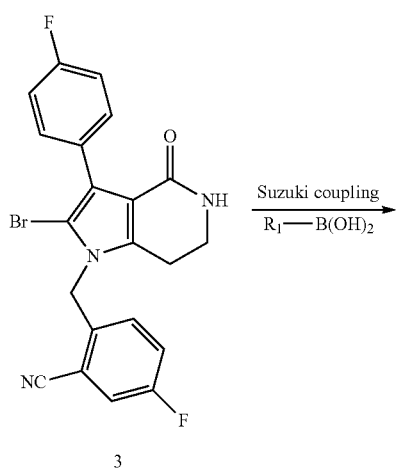

3

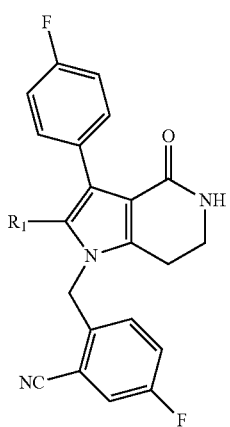

4

Scheme 2 describes an alternative method to access compounds of this invention. Brominated pyrrole 6 would be available in one step from 5 (prepared as described in *J. Med. Chem.*, 51:487 (2008)) using standard halogenation conditions. Reaction of 6 with appropriate boronates or boronic acids under Suzuki conditions can yield pyrrole 7. Alkylation and deprotection using appropriate conditions known to those in the art of organic synthesis would provide compounds similar to 8.

Scheme 2

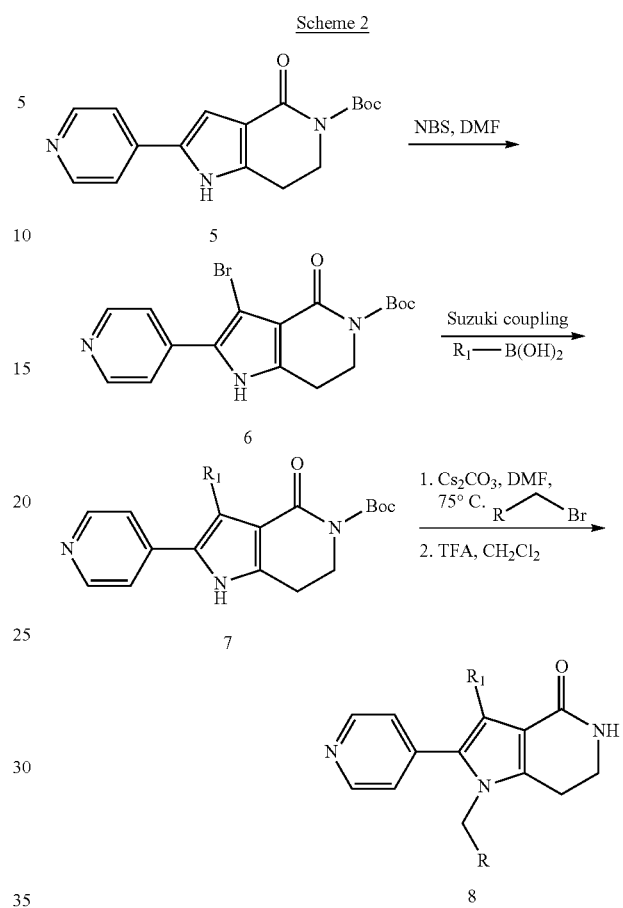

Scheme 3 describes a method for accessing compounds exemplified by 14. Bromination of 1-(2-chloropyridin-4-yl)ethanone can provide 9, which can undergo reaction with 2,4-piperidine-dione to produce pyrrole 10. Halogenation of the pyrrole, followed by protection with an appropriate protecting group according to procedures known to those in the art, can yield 11. Compounds of the type exemplified by 12, can be prepared by reaction of 11 with appropriate boronates or boronic acids under Suzuki conditions. Alkylation of pyrrole 12 with 4-(bromomethyl)tetrahydro-2H-pyran under standard conditions could be followed by a Buchwald-Hartwig reaction (Surry, D. S. et al., *Angew. Chem. Int. Ed.*, 47:6338-6361 (2008)) to form aminopyridines such as 14. Appropriate functionalization of intermediates used in this invention to prepare compounds similar to 14 can be achieved through the Buchwald-Hartwig reaction, Ullmann reaction or simple reactions known to those in the art.

Scheme 3

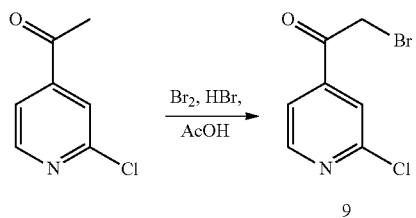

-continued

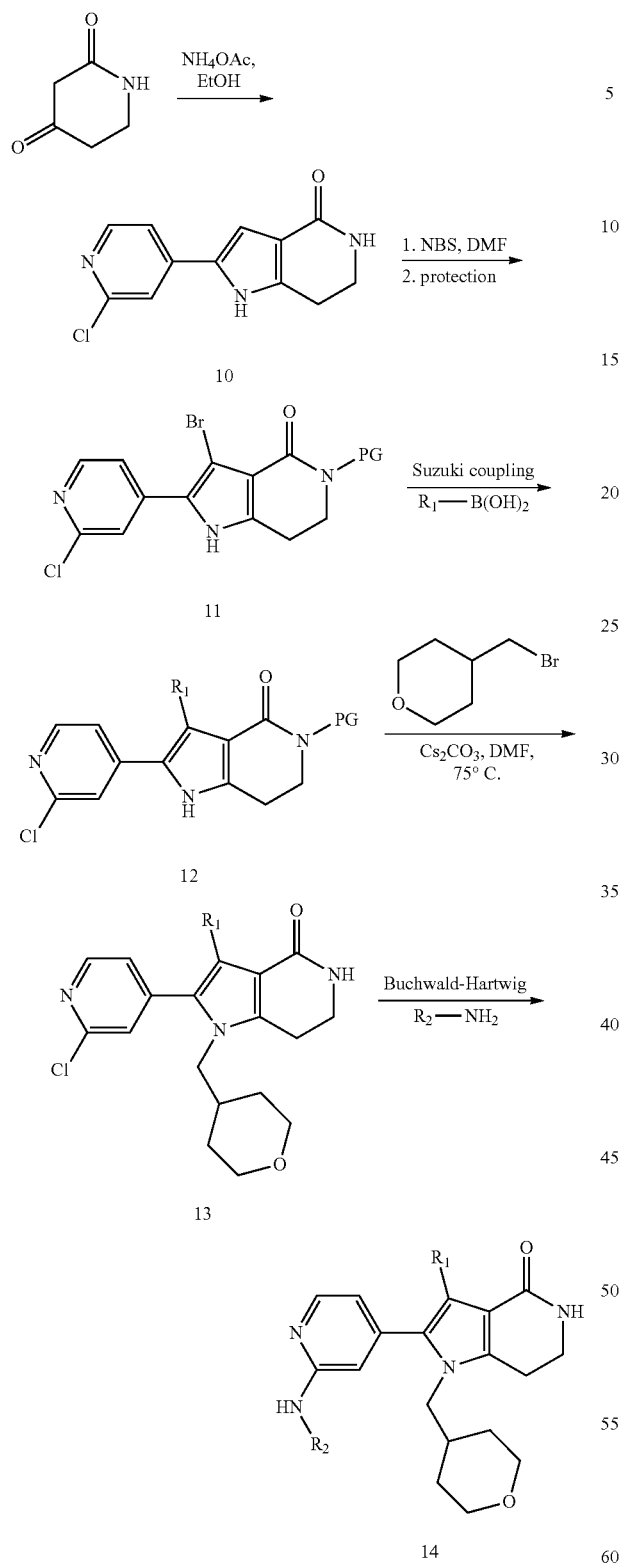

Deprotection under appropriate conditions known to those in the art would yield penultimate compound 17. Alkylation of 17 would provide the final compounds of this type in this invention.

Scheme 4

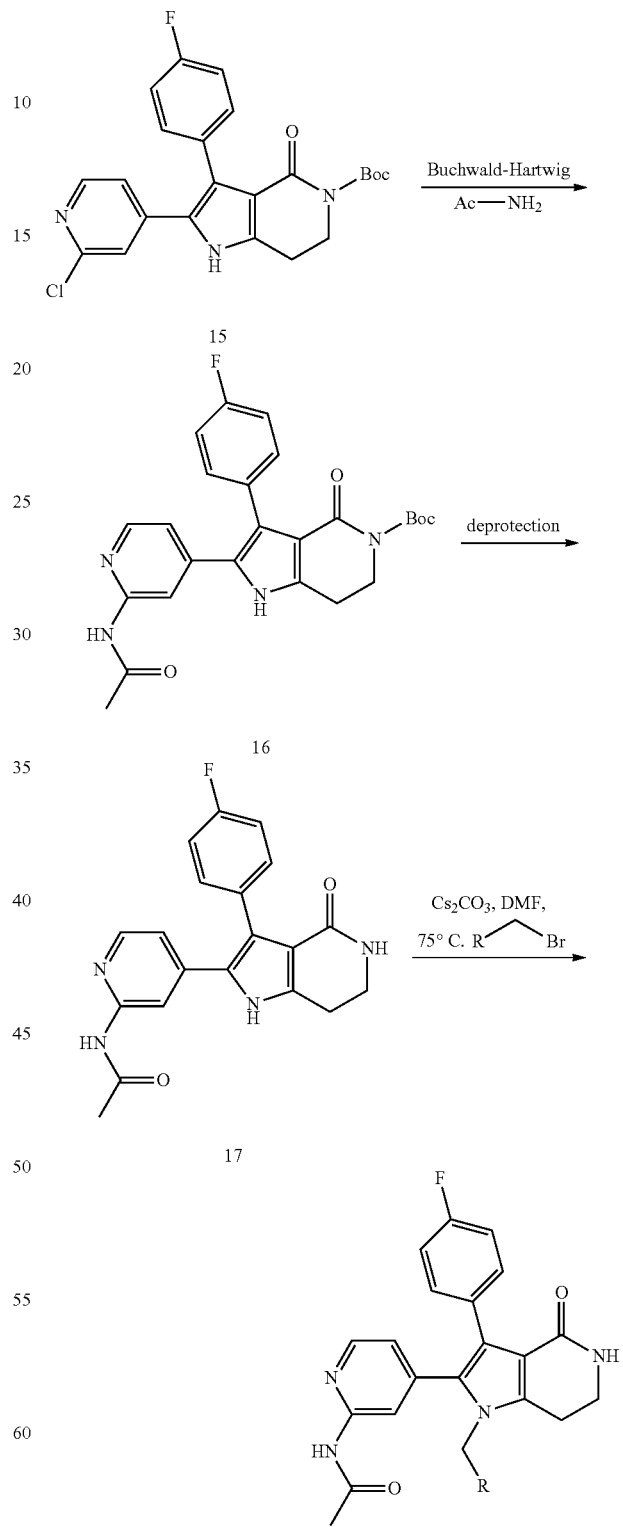

Scheme 4 describes functionalization of the N-pyrrole position on intermediate 17 utilizing an alkylation reaction to produce compounds related to 18. Intermediate 15 can undergo a Buchwald-Hartwig coupling reaction to form the substituted pyridine 16.

Scheme 5 outlines the protocols associated with obtaining compounds of the type exemplified by 21. Intermediate 6 can undergo reaction with 4-(bromomethyl) tetrahydro-2H-pyran under standard conditions to provide 19. Using an appropriate boronate or boronic acid, 19 can be coupled using the Suzuki reaction. Deprotection of compounds of the type exemplified by 20 under acidic conditions would provide the final compounds as illustrated by 21.

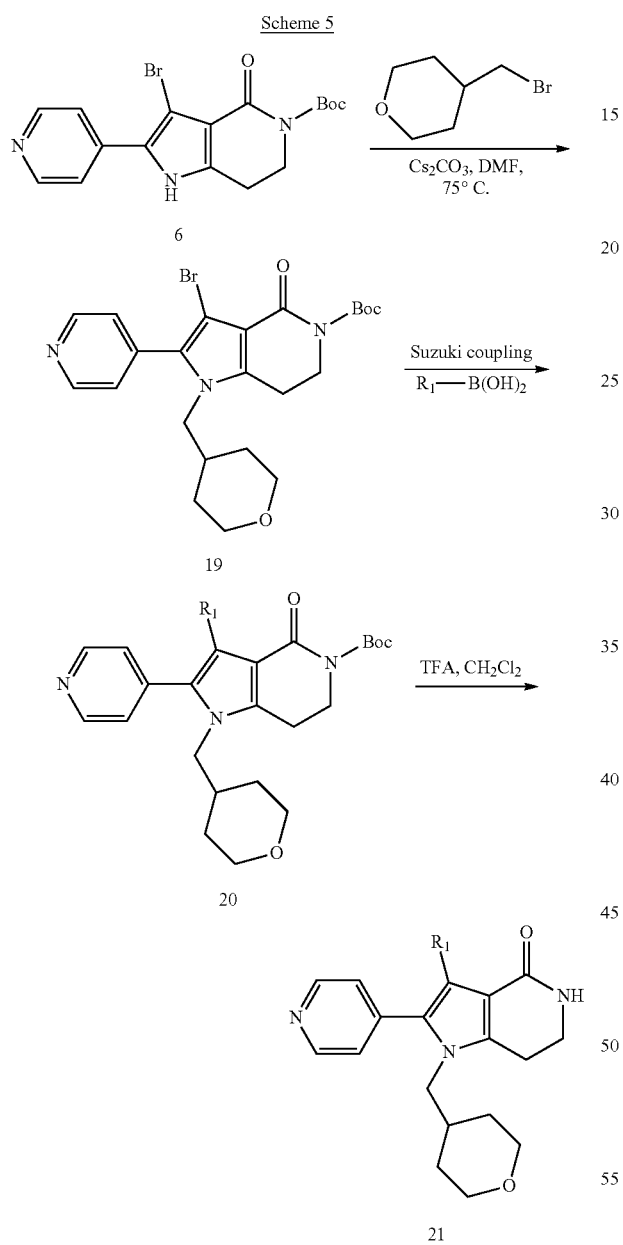

Scheme 6 offers an alternative route to structurally related compounds as presented in Scheme 5. Intermediate 6 can undergo acidic deprotection, followed by reaction with 2-(bromomethyl)-5-fluorobenzonitrile to yield 22. Using an appropriate boronate or boronic acid, 22 can be coupled using the Suzuki reaction, providing compounds of the type exemplified by 23.

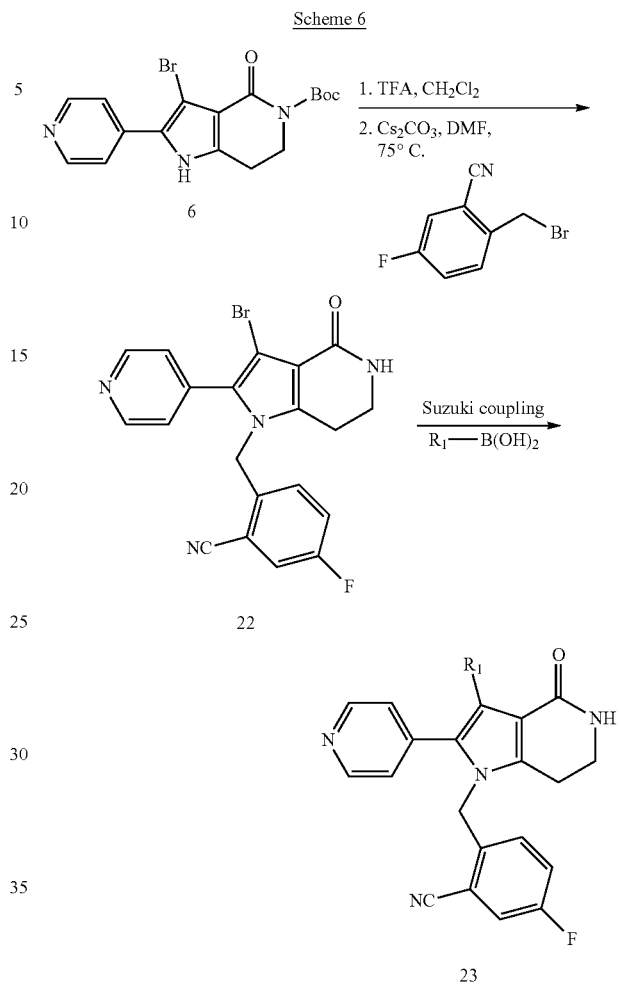

Alternative preparation of substituted aminopyridines such as 27 is presented in Scheme 7. Brominated pyrrole 24 can undergo a chemoselective Suzuki reaction under standard conditions known to those in the art with (4-fluorophenyl)boronic acid, followed by a standard alkylation reaction with 1-(bromomethyl)-2-fluoro-4-(trifluoromethyl) benzene to provide 26. Appropriate amines can undergo reaction with chloropyridine 26 to yield compounds of the type exemplified by 27. Appropriate functionalization of intermediates used in this invention to prepare compounds similar to 27 can be achieved through the Buchwald-Hartwig reaction, Ullmann reaction or simple reactions known to those in the art.

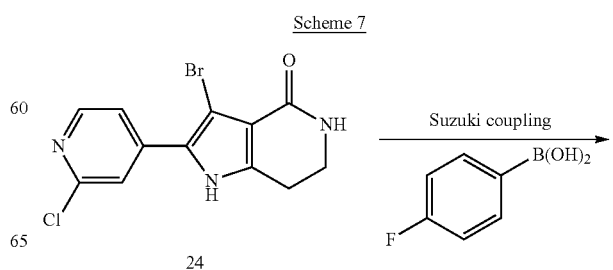

Scheme 8

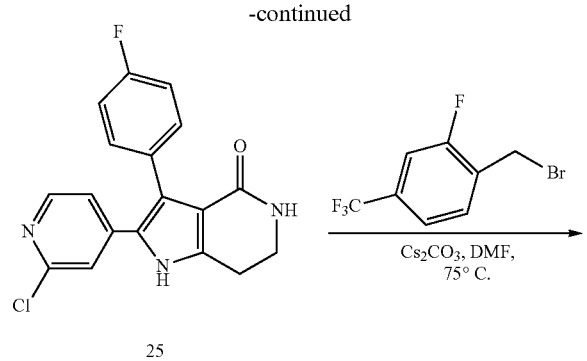

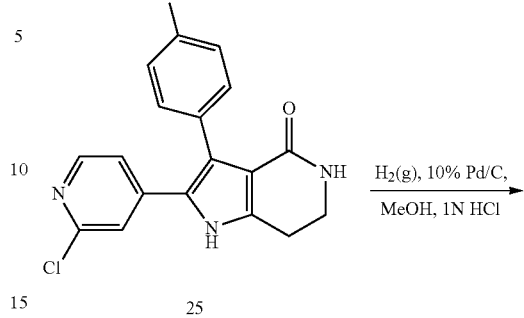

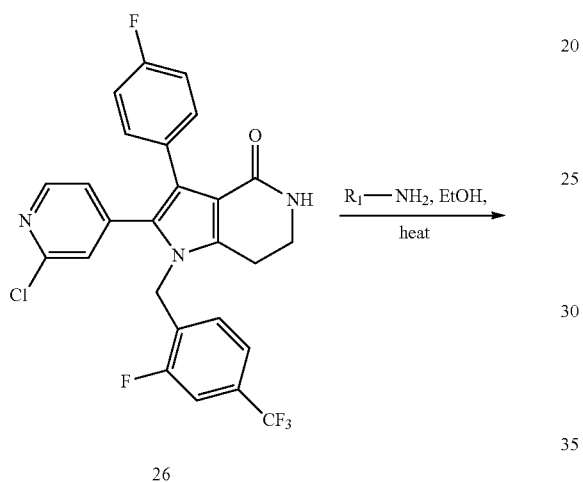

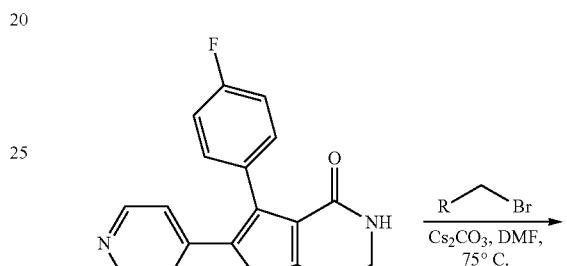

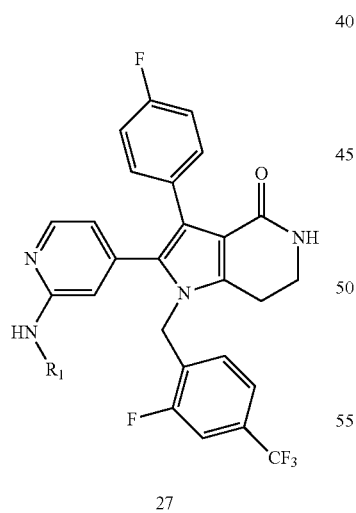

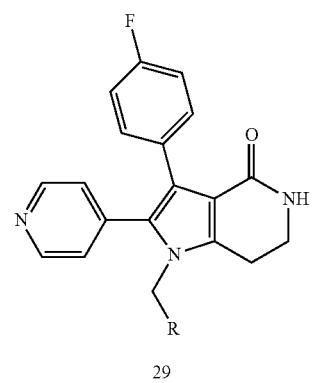

Alternative substitution can be explored starting from intermediate 25 as shown in Scheme 8. Hydrogenation of 25 results in the generation of the bis HCl salt of 28. Pyrrole 28 can undergo an alkylation reaction with a suitable alkyl halide under the conditions listed in the scheme or alternative conditions known to those in the art to access compounds of the type exemplified by 29.

Scheme 9 highlights an additional approach to access compounds of this invention, similar to that illustrated in Scheme 6. Intermediate 10 can undergo reduction under standard hydrogenation conditions to generate intermediate 30. Alkylation of the pyrrole using 2-(bromomethyl)-5-fluorobenzonitrile or another appropriate alkyl halide under standard conditions known to those in the art can produce intermediates such as 31. Bromination followed by Suzuki coupling under standard conditions with an appropriate boronic acid provides compounds of this invention exemplified by 33. Appropriate functionalization of intermediates used in this invention to prepare compounds similar to 33 can be achieved through the Suzuki reaction with boronic acids or boronate esters, Stille reaction or simple reactions known to those in the art.

Scheme 9

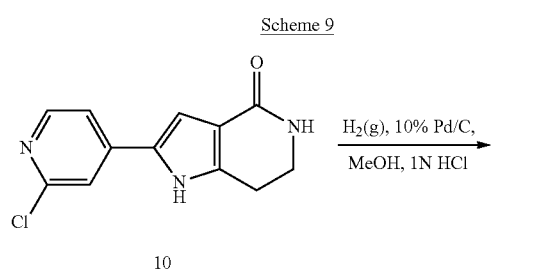

10

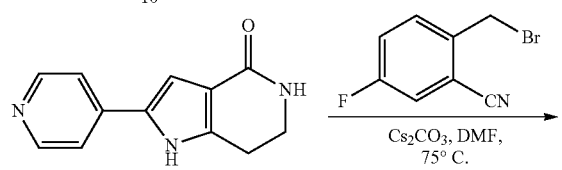

30

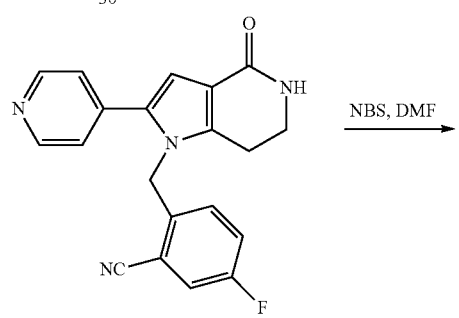

31

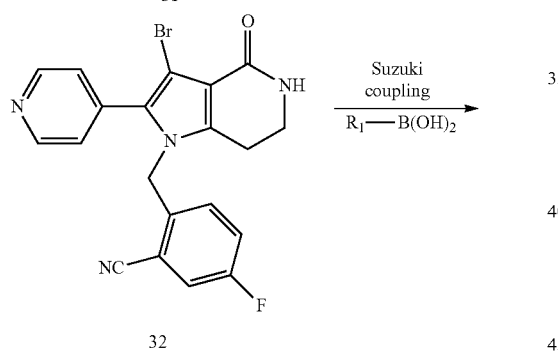

32

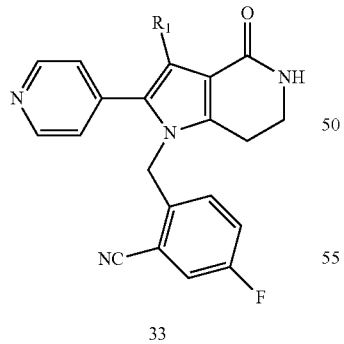

33

Scheme 10 illustrates an approach to the synthesis of compounds exemplified by 37. Analogous to Scheme 1, pyrrole 34 can be prepared by cyclization of an alpha amino ketone and piperidine-2,4-dione. Halogenation of the pyrrole, followed by alkylation of the pyrrole using conditions listed or alternative appropriate conditions known to those in the art of organic synthesis would yield pyrrole 36. Functionalization of intermediate 36 can be achieved through a Suzuki coupling reaction to provide compounds of the type exemplified by 37. Appropriate functionalization of intermediates used in this invention to prepare compounds similar to 37 can be achieved through the Suzuki reaction, Stille reaction or simple reactions known to those in the art of organic synthesis.

Scheme 10

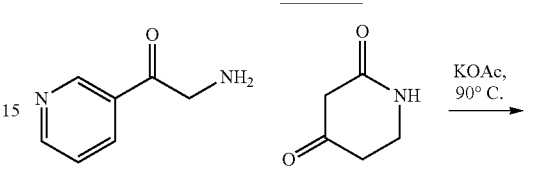

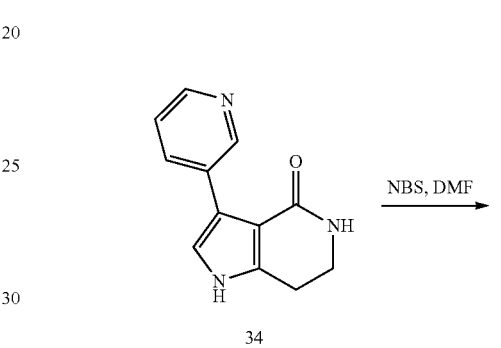

34

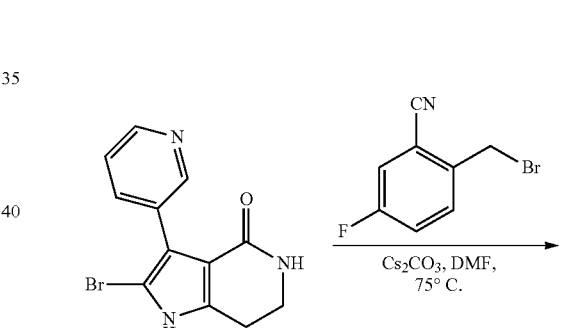

35

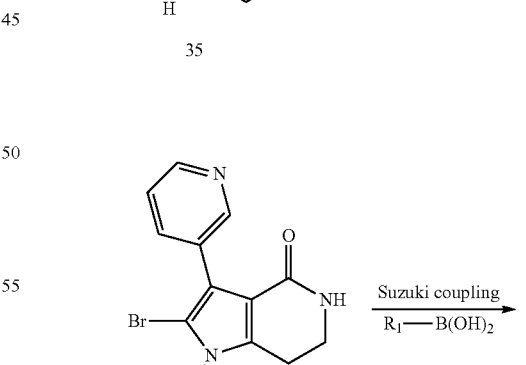

36

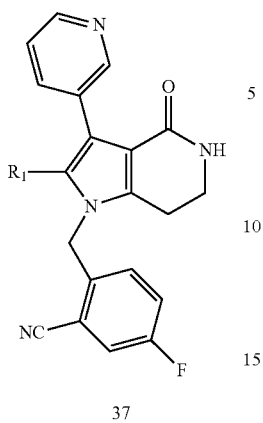

37

An approach to alternative lactam substitution is highlighted in Scheme 11. The lactam could be assembled from 2-cyano-2,2-dimethylpropanoate which can undergo reduction to amine 38 in the presence of Raney nickel. Intermediate 39 would be available from 38 and monomethyl malonate using the standard coupling conditions shown below or alternative conditions known to those in the art. The substituted piperidine-2,4-dione 41 could be generated by base-mediated Claisen condensation to yield 40, followed by subsequent decarboxylation. Pyrrole core 42 could be accessed via cyclization with an appropriately substituted alpha amino ketone, in a similar fashion to that reported in Scheme 1. Bromination of 42 under standard conditions would provide pyrrole 43. Alkylation of pyrrole 43 with a suitable electrophile under conditions listed or alternative appropriate conditions known to those in the art of organic synthesis would yield pyrroles of the type exemplified by 44. Suzuki coupling, or an alternative coupling know to those in the art, would yield compounds of this invention similar to 45.

Scheme 11

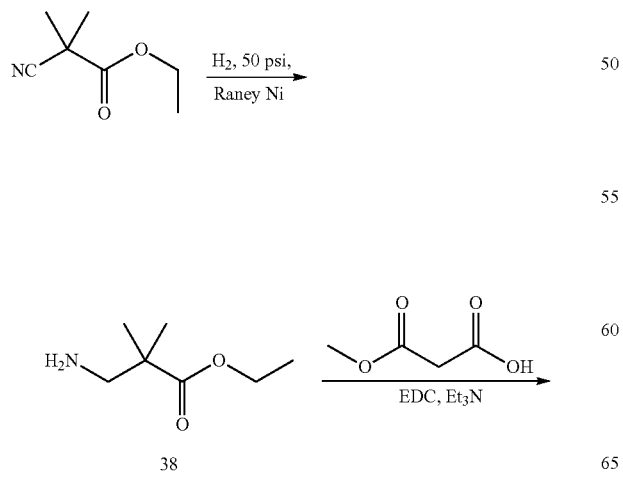

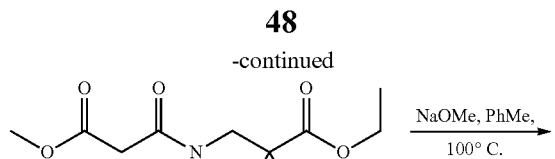

39

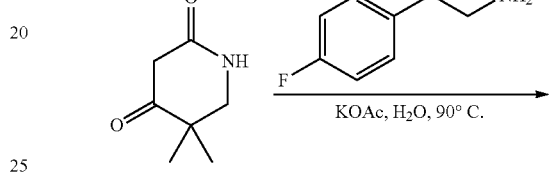

40

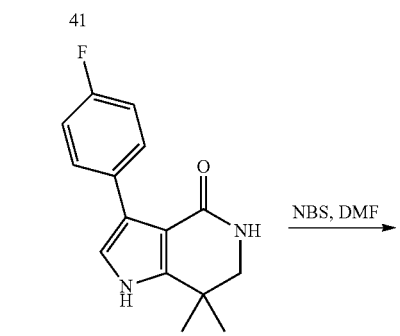

41

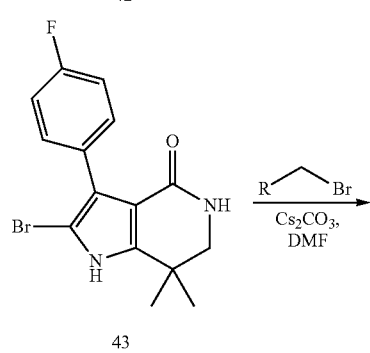

42

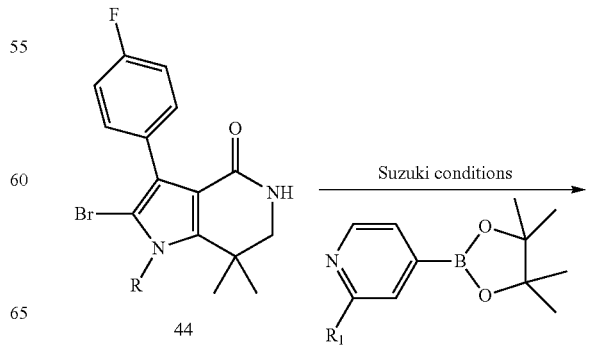

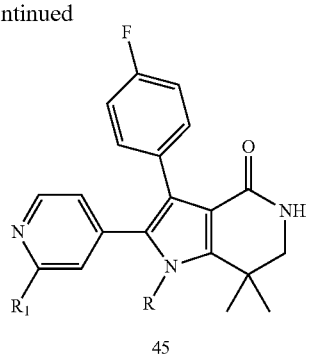

Scheme 12 outlines an additional method to access compounds of this invention. Pyrrololactam 26 can undergo an oxidation mediated by DDQ to yield 46. Intermediate 46 can be further elaborated to compounds of the type exemplified by 47 using palladium-mediated coupling of a suitable amine under the conditions shown, or alternative conditions known to those in the art of organic synthesis. Alternatively, chlorine removal on 46 under hydrogenation conditions would provide pyridine 48.

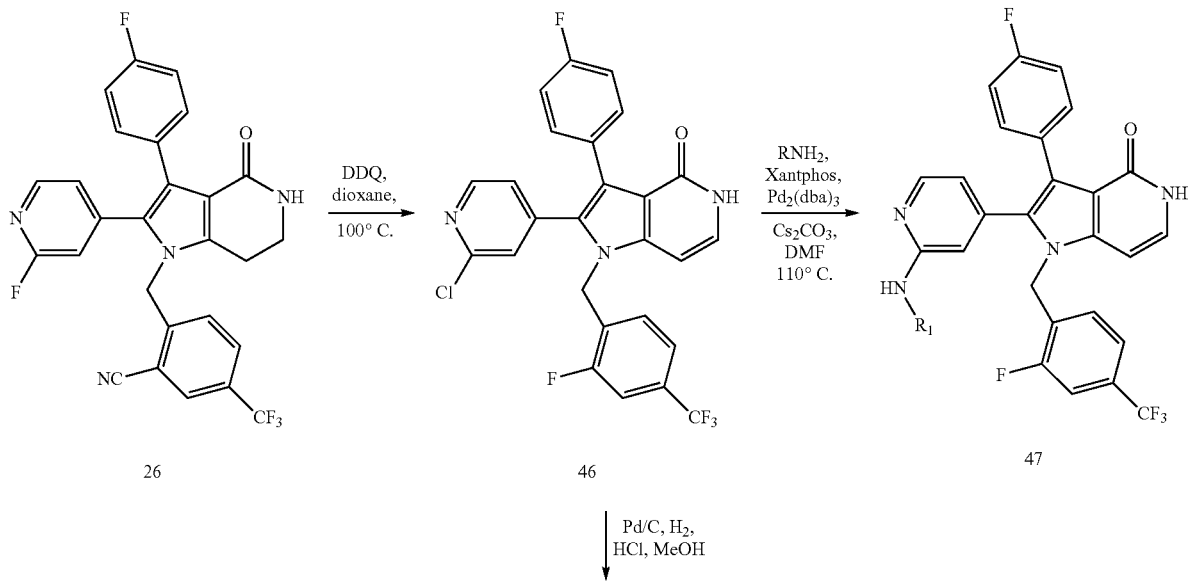

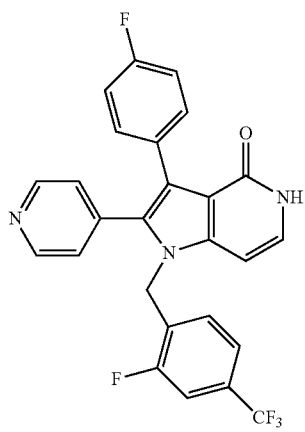

Compounds having alternative substitution of the pyrrole with sulfur instead of carbon can be accessed from 2 as outlined in Scheme 13. Use of a sulfonyl chloride can produce sulfonamide 49. Suzuki coupling, or an alternative coupling know to those in the art, would yield compounds of this invention similar to 50.

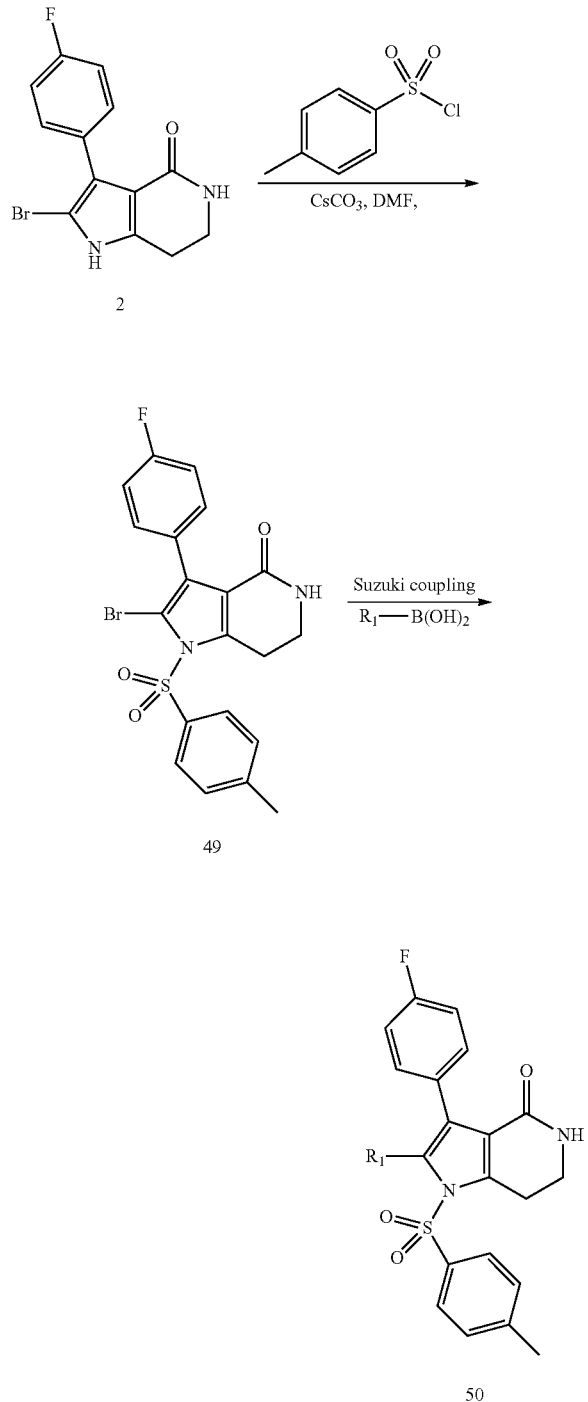

Purification of intermediates and final products was carried out via either normal or reverse phase chromatography. Normal phase chromatography was carried out using pre- packed SiO$_2$ cartridges eluting with either gradients of hexanes and ethyl acetate or dichloromethane and methanol unless otherwise indicated. Reverse phase preparative HPLC or LCMS was carried out using C18 columns eluting with gradients of Solvent A (90% water, 10% methanol, 0.1% TFA) and Solvent B (10% water, 90% methanol, 0.1% TFA, UV 220 nm), or with gradients of Solvent A (95% water, 5% acetonitrile, 0.1% TFA) and Solvent B (5% water, 95% acetonitrile, 0.1% TFA, UV 220 nm), or with gradients of Solvent A (98% water, 2% acetonitrile, 0.05% TFA) and Solvent B (98% acetonitrile, 2% water, 0.05% TFA, UV 254 nm), or with gradients of Solvent A (95% water, 5% acetonitrile with 10 mM ammonium acetate) and Solvent B (95% acetonitrile, 5% water with 10 mM ammonium acetate).

In the majority of examples, two analytical LCMS injections were used to determine final purity:

Method A: Column: Waters Acquity UPLC BEH C18, 2.1×50 mm, 1.7 µM particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.11 mL/min; Detection: UV at 220 nm; and Method B: Column: Waters Acquity UPLC BEH C18, 2.1×50 mm, 1.7 µm particles; Mobile Phase A: 5:95 acetonitrile:water with 0.1% TFA; Mobile Phase B: 95:5 acetonitrile:water with 0.1% TFA; Temperature: 50° C.; Gradient: 0-100% B over 3 min, then a 0.75 min hold at 100% B; Flow: 1.11 mL/min; Detection: UV at 220 nm.

In a minority of examples, analytical HPLC injections were used to determine final purity:

Method A: Column: SunFire C18, 3.0×150 mm, 3.5 µM particles; Mobile Phase A: 5:95 acetonitrile:water with 0.1% TFA; Mobile Phase B: 95:5 acetonitrile:water with 0.1% TFA; Gradient: 0-100% B over 10 minutes; Flow: 1 mL/min; Detection: UV at 220 and 254 nm;

Method B: Column: XBridge Phenyl, 3.0×150 mm, 3.5 µM particles; Mobile Phase A: 5:95 acetonitrile:water with 0.1% TFA; Mobile Phase B: 95:5 acetonitrile:water with 0.1% TFA; Gradient: 0-100% B over 10 minutes; Flow: 1 mL/min; Detection: UV at 220 and 254 nm;

Method C: Column: XBridge C18, 3.0×150 mm, 3.5 µM particles; Mobile Phase A: 5:95 methanol:water with 10 mM ammonium bicarbonate; Mobile Phase B: 95:5 methanol:water with 10 mM ammonium bicarbonate; Gradient: 0-100% B over 15 minutes; Flow: 1 mL/min; Detection: UV at 220 and 254 nm; and Method D: Column:)(Bridge Phenyl, 3.0×150 mm, 3.5 µM particles; Mobile Phase A: 5:95 methanol:water with 10 mM ammonium bicarbonate; Mobile Phase B: 95:5 methanol:water with 10 mM ammonium bicarbonate; Gradient: 0-100% B over 15 minutes; Flow: 1 mL/min; Detection: UV at 220 and 254 nm.

A majority of mass spectra runs were: LCMS(ESI) m/z: [M+H]$^+$ BEH C18, 2.11×50 mm, 1.7 µm; Mobile Phase A: 2:98 water:acetonitrile with 0.1% TFA; Mobile Phase B: 98:2 acetonitrile:water with 0.1% TFA; Gradient: 0-100% B over 2 minutes; Flow: 0.8 mL/min; Detection: UV at 220 nm.

Example 1

5-Fluoro-2-((3-(4-fluorophenyl)-2-(3-methyl-1H-pyrazol-4-yl)-4-oxo-4,5,6,7-tetrahydro-1H-pyrrolo[3,2-c]pyridin-1-yl)methyl)benzonitrile

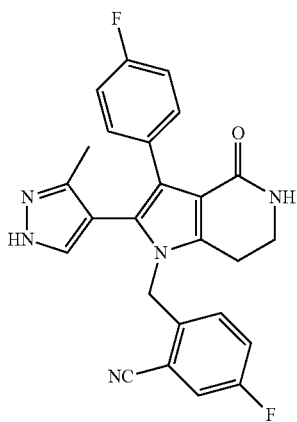 [SMILES: Cc1n[nH]cc1-c1c(-c2ccc(F)cc2)c2c(n1Cc1ccc(F)cc1C#N)CCNC2=O]

1A: 3-(4-Fluorophenyl)-6,7-dihydro-1H-pyrrolo[3,2-c]pyridin-4(5H)-one: A solution of piperidine-2,4-dione (6.93 g, 61.3 mmol), 2-amino-1-(4-fluorophenyl)ethanone hydrochloride (11.62 g, 61.3 mmol) and potassium acetate (12.03 g, 123 mmol) in water (130 mL) was stirred to give a clear solution. Within 5 min a thick white precipitate formed, and the reaction mixture was heated to 90° C. for 2 h. The reaction mixture was cooled down to rt. The solid was collected by filtration to afford the desired product 1A (13.06 g, 93% yield). $^1$H NMR (400 MHz, CD$_3$OD) δ 7.65-7.57 (m, 2H), 7.03-6.92 (m, 2H), 6.79 (s, 1H), 3.54 (t, J=6.9 Hz, 2H), 2.87 (t, J=6.9 Hz, 2H). MS(ESI) m/z 231.2 (M+H).

1B: 2-Bromo-3-(4-fluorophenyl)-6,7-dihydro-1H-pyrrolo[3,2-c]pyridin-4(5H)-one: To a suspension solution of 1A (5.33 g, 23.15 mmol) in DMF (100 mL) at 23° C. was added NBS (4.12 g, 23.15 mmol). The reaction become homogeneous and was stirred for 20 minutes. The reaction mixture was concentrated and triturated with MeOH (10 mL) to yield 1B (6.70 g, 94%). $^1$H NMR (400 MHz, DMSO-d$_6$) δ 12.02 (br. s., 1H), 7.44-7.34 (m, 2H), 7.18-7.09 (m, 2H), 6.95 (br. s., 1H), 3.36 (td, J=6.8, 2.9 Hz, 2H), 2.78-2.70 (m, 2H). MS(ESI) m/z 311.1 (M+H).

1C: 2-((2-Bromo-3-(4-fluorophenyl)-4-oxo-4,5,6,7-tetrahydro-1H-pyrrolo[3,2-c]pyridin-1-yl)methyl)-5-fluorobenzonitrile: A suspension solution of 1B (2.1 g, 6.79 mmol), 2-(bromomethyl)-5-fluorobenzonitrile (1.724 g, 7.81 mmol) and Cs$_2$CO$_3$ (3.32 g, 10.19 mmol) in DMF (54 mL) was heated to 100° C. for 20 minutes in a microwave reactor. The reaction mixture was filtered and concentrated. Water (80 mL) was added. After stirring for 20 minutes, the solid was collected as 1C (3 g, 97% yield). $^1$H NMR (400 MHz, CD$_3$OD) δ 7.66 (dd, J=8.1, 2.6 Hz, 1H), 7.51-7.39 (m, 3H), 7.11-7.02 (m, 2H), 6.92 (dd, J=8.8, 5.1 Hz, 1H), 5.51 (s, 2H), 3.57 (t, J=6.9 Hz, 2H), 2.87 (t, J=6.9 Hz, 2H). MS(ESI) m/z 442.3 (M+H).

Example 1: 5-Fluoro-2-((3-(4-fluorophenyl)-4-oxo-2-(2-(trifluoromethyl)pyridin-4-yl)-4,5,6,7-tetrahydro-1H-pyrrolo[3,2-c]pyridin-1-yl)methyl)benzonitrile: A degassed solution of 1C (20 mg, 0.045 mmol), 3-methyl-4-(4,4,5,5-tetramethyl-1,3,2-dioxaborolan-2-yl)-1H-pyrazole (18.82 mg, 0.090 mmol), PdCl$_2$(dppf)-CH$_2$Cl$_2$ adduct (3.69 mg, 4.52 μmol) and potassium phosphate tribasic 2M solution (0.068 mL, 0.136 mmol) in DMF (0.5 mL) was heated to 90° C. for 1 h. The reaction mixture was purified on preparative HPLC to give 1 (14.8 mg, 74% yield). $^1$H NMR (500 MHz, DMSO-hd6) δ 7.94 (d, J=5.7 Hz, 1H), 7.63-7.54 (m, 1H), 7.41 (dd, J=8.1, 5.7 Hz, 2H), 7.21-7.09 (m, 3H), 6.88 (dd, J=8.6, 5.2 Hz, 1H), 5.45 (s, 2H), 3.41 (br. s., 2H), 2.80 (t, J=6.6 Hz, 2H), 2.50 (s, 3H merge with DMSO). MS(ESI) m/z 444.1 (M+H).

Example 2

3-((3-(4-Fluorophenyl)-4-oxo-2-(pyridin-4-yl)-4,5,6,7-tetrahydro-1H-pyrrolo[3,2-c]pyridin-1-yl)methyl)benzonitrile

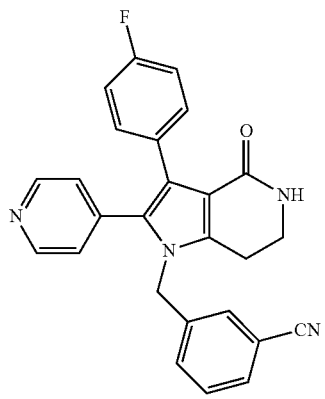 [SMILES: N#Cc1cccc(Cn2c3c(c(-c4ccc(F)cc4)c2-c2ccncc2)C(=O)NCC3)c1]

2A: tert-Butyl 3-bromo-4-oxo-2-(pyridin-4-yl)-6,7-dihydro-1H-pyrrolo[3,2-c]pyridine-5(4H)-carboxylate: N-Bromosuccinimide (254 mg, 1.43 mmol) was added to a stirred solution of tert-butyl 4-oxo-2-(pyridin-4-yl)-6,7-dihydro-1H-pyrrolo[3,2-c]pyridine-5(4H)-carboxylate (448 mg, 1.43 mmol) (prepared as described in *J. Med. Chem.*, 51:487 (2008)) in DMF (14 mL) at RT. After 0.5 h, the reaction was partitioned between EtOAc and water. The aqueous phase was extracted with EtOAc and the combined organic phases were washed with water and brine. After drying with sodium sulfate, the solvent was removed to leave 2A (560 mg) as a thick red gum that was used as such. $^1$H NMR (500 MHz, CDCl$_3$) δ 11.12 (br. s., 1H), 8.51 (d, J=5.3 Hz, 2H), 7.74 (d, J=6.0 Hz, 2H), 4.09 (t, J=6.3 Hz, 2H), 3.01 (t, J=6.3 Hz, 2H), 1.54 (s, 9H). MS(ES) m/z 394.0 (M+H).

2B: tert-Butyl 3-(4-fluorophenyl)-4-oxo-2-(pyridin-4-yl)-6,7-dihydro-1H-pyrrolo[3,2-c]pyridine-5(4H)-carboxylate (6-cyanopyridin-2-yl)carbamate: A mixture of 6A (560 mg, 1.43 mmol), (4-fluorophenyl)boronic acid (300 mg, 2.14 mmol), [1,1'-bis(diphenylphosphino)ferrocene]dichloropalladium(II) (104 mg, 0.143 mmol) and sodium carbonate (227 mg, 2.14 mmol) in a microwave vial was flushed with nitrogen. A mixture of dioxane (10 mL) and water (2 mL) that had been sparged with nitrogen for 5 min was added and the vial was sealed and heated at 90° C. ON. EtOAc and water were added and the suspension was filtered through CELITE®. The organic phase of the filtrate was separated, washed with brine and dried with sodium sulfate. Removal of the solvent followed by silica gel radial chromatography eluting with DCM containing 0 to 7% MeOH gave 2B (234 mg, 40% yield) as a brown foam. $^1$H NMR (500 MHz, CDCl$_3$) δ 10.64 (br. s., 1H), 8.31 (d, J=5.6 Hz, 2H), 7.25-7.19 (m, 2H), 6.99 (d, J=6.0 Hz, 2H), 6.93 (t, J=8.7 Hz, 2H), 4.08 (t, J=6.2 Hz, 2H), 2.84 (t, J=6.3 Hz, 2H), 1.49 (s, 9H). MS(ES) m/z 408.2 (M+H).

Example 2: Dry DMF (1 mL) was added to a mixture of 2B (30 mg, 0.074 mmol), 3-(bromomethyl)benzonitrile (22 mg, 0.11 mmol) and cesium carbonate (84 mg, 0.26 mmol) in a dried vial that had been flushed with nitrogen. This was left stirring overnight and then partitioned between DCM and water. The aqueous phase was separated and extracted with additional DCM. The combined organic phases were dried with sodium sulfate and the solvent removed. The residue was dissolved in DCM (1.0 mL) and TFA (1.0 mL) was added. After 1 h the solvents were removed and the residue was dissolved in DMSO and purified via preparative HPLC (100×30 mm Luna C18 column, gradient elution with A:B=0:100 to A:B=45:55 [A=95% H$_2$O: 5% MeOH: 0.1% TFA; B=5% H$_2$O: 95% MeOH: 0.1% TFA] over 20 min) followed by SCX capture and release with 2 N NH$_3$ in MeOH afforded the title compound (7.4 mg, 23% yield). $^1$H NMR (500 MHz, CDCl$_3$) δ 8.52-8.48 (m, 2H), 7.63 (d, J=7.9 Hz, 1H), 7.50 (t, J=7.9 Hz, 1H), 7.27-7.22 (m, 3H), 7.14 (s, 1H), 6.96-6.90 (m, 4H), 5.35 (br. s., 1H), 5.14 (s, 2H), 3.65-3.59 (m, 2H), 2.78 (t, J=6.9 Hz, 2H). MS(ES) m/z 423.1 (M+H).

Example 3

N-(4-(3-(4-Fluorophenyl)-4-oxo-1-((tetrahydro-2H-pyran-4-yl)methyl)-4,5,6,7-tetrahydro-1H-pyrrolo[3,2-c]pyridin-2-yl)pyridin-2-yl)acetamide

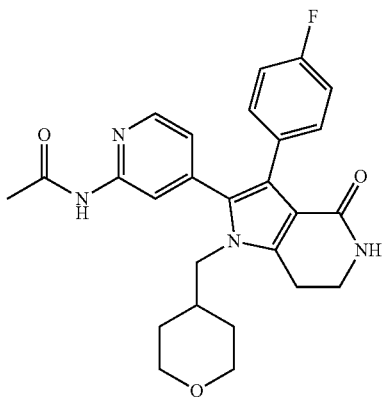 [SMILES: CC(=O)Nc1cc(-c2c(-c3ccc(F)cc3)c3c(n2CC2CCOCC2)CCNC3=O)ccn1]

3A: 2-Bromo-1-(2-chloropyridin-4-yl)ethanone, hydrobromide: To an acetic acid (80 ml) solution of 1-(2-chloropyridin-4-yl)ethanone (3.11 g, 19.99 mmol), bromine (1.133 ml, 21.99 mmol) and HBr in acetic acid (3.29 ml, 19.99 mmol) were added. The reaction was stirred at rt for 2 h. The suspension was filtered. The collected solid was washed with diethyl ether and dried under vacuum, yielding 3A (6.06 g, 19.21 mmol, 96% yield) as a white solid. MS(ES+) m/z 235.9 (M+H).

3B: 2-(2-Chloropyridin-4-yl)-6,7-dihydro-1H-pyrrolo[3,2-c]pyridin-4(5H)-one: To a round bottom flask charged with 3A (6.06 g, 19.21 mmol), piperidine-2,4-dione (2.391 g, 21.14 mmol), ammonium acetate (5.92 g, 77 mmol) and ethanol (64.0 ml) were added. The reaction mixture was stirred at rt for 2 h. Water (20 ml) was added and stirring was continued for 3 h. The product was collected via filtration. The collected solid was washed with water and dried under vacuum ON, yielding 3B (2.26 g, 9.12 mmol, 47.5% yield) as a white solid. MS(ES+) m/z 248.0 (M+H).

3C: 3-Bromo-2-(2-chloropyridin-4-yl)-6,7-dihydro-1H-pyrrolo[3,2-c]pyridin-4(5H)-one: To a DMF (48.4 ml) suspension of 3B (3 g, 12.11 mmol), NBS (2.264 g, 12.72 mmol) was added. The reaction was stirred at rt for 1 h. Water (200 ml) was added and stirring was continued for 30 minutes. The product was collected via filtration. The collected solid was dried under vacuum, yielding 3C (3.53 g, 10.81 mmol, 89% yield) as a white solid. $^1$H NMR (400 MHz, CD$_3$OD) δ 8.34 (d, J=5.5 Hz, 1H), 7.83 (s, 1H), 7.79 (d, J=5.5 Hz, 1H), 3.54 (t, J=6.9 Hz, 2H), 2.95 (t, J=6.9 Hz, 2H). MS(ES+) m/z 248.0 (M+H).

3D: tert-Butyl 3-bromo-2-(2-chloropyridin-4-yl)-4-oxo-6,7-dihydro-1H-pyrrolo[3,2-c]pyridine-5(4H)-carboxylate: To a round bottom flask charged with 3C (2.25 g, 6.89 mmol), Boc$_2$O (1.680 ml, 7.23 mmol), DMF (17.22 ml) and Hunig's base (2.407 ml, 13.78 mmol) were added. DMAP (0.084 g, 0.689 mmol) was added. The reaction was stirred at rt for 3 h. The reaction was diluted with ethyl acetate and washed successively with 10% LiCl, water and brine. The ethyl acetate extract was dried over sodium sulfate, filtered and concentrated on silica gel under reduced pressure. The product was purified via medium pressure chromatography (0-10% ethyl acetate-hexanes solvent system over 10 column volumes held at 10% for 4 CVs), yielding 3D (1.52 g, 3.56 mmol, 51.7% yield) as a white solid. $^1$H NMR (400 MHz, DMSO-d$_6$) δ 8.49 (d, J=5.1 Hz, 1H), 7.58 (d, J=0.7 Hz, 1H), 7.49 (br. s., 1H), 7.44 (dd, J=5.1, 1.3 Hz, 1H), 5.40-5.30 (m, 1H), 3.42 (td, J=6.9, 2.6 Hz, 2H), 3.19-3.11 (m, 2H), 1.24 (s, 9H). MS(ES+) m/z 428.2 (M+H).

3E: tert-Butyl 2-(2-chloropyridin-4-yl)-3-(4-fluorophenyl)-4-oxo-6,7-dihydro-1H-pyrrolo[3,2-c]pyridine-5(4H)-carboxylate: To a pressure relief vial charged with 3D (1.50 g, 3.52 mmol), (4-fluorophenyl)boronic acid (0.590 g, 4.22 mmol), and PdCl$_2$(dppf)-CH$_2$Cl$_2$ adduct (0.287 g, 0.352 mmol) were added. 1,4-Dioxane (23.44 ml) and 2.0 M potassium phosphate, tribasic (5.27 ml, 10.55 mmol) were added. The suspension was purged with nitrogen for 5 min. The vial was sealed and heated to 90° C. for 1 h. The reaction was diluted with methanol (10 ml), filtered and concentrated under reduced pressure, yielding an oil. The oil was diluted with ethyl acetate and washed successively with water and brine. The ethyl acetate extract was dried over sodium sulfate, filtered and concentrated on silica gel under reduced pressure. The product was purified via medium pressure chromatography (0-10% DCM-MeOH solvent system over 10 column volumes; held at 10% for 4 CVs), yielding 3E (1.14 g, 2.58 mmol, 73.4% yield) as a white solid. MS(ES+) m/z 442.3 (M+H).

3F: 2-(2-Chloropyridin-4-yl)-3-(4-fluorophenyl)-1-((tetrahydro-2H-pyran-4-yl)methyl)-6,7-dihydro-1H-pyrrolo[3,2-c]pyridin-4(5H)-one: To a reaction pressure relief vial charged with 3E (0.5 g, 1.132 mmol) and cesium carbonate (1.106 g, 3.39 mmol), DMF (5.7 ml) and 4-(bromomethyl)tetrahydro-2H-pyran (0.304 g, 1.697 mmol) were added. The suspension was purged with nitrogen, sealed and heated to 75° C. for 16 h. The reaction was cooled to rt, diluted with ethyl acetate and washed successively with water, 10% LiCl, water and brine. The ethyl acetate extract was dried over sodium sulfate, filtered and concentrated on silica gel under reduced pressure. The product was purified via medium pressure chromatography (0-10% ethyl acetate-hexanes solvent system over 10 column volumes, held at 10% for 10 CVs), yielding 3F (297 mg, 0.675 mmol, 59.7% yield) as a white solid. MS(ES+) m/z 440.4 (M+H).

Example 3: To a pressure relief vial charged with 3F (15 mg, 0.034 mmol), acetamide (4.03 mg, 0.068 mmol), tris (dibenzylideneacetone)dipalladium(O) (6.24 mg, 6.82 µmol), cesium carbonate (22.22 mg, 0.068 mmol) and Xantphos (3.95 mg, 6.82 µmol) was added 1,4-dioxane (136 µl). The suspension was purged with nitrogen for 5 min, sealed and heated to 110° C. for 1 h. The reaction was cooled to rt, diluted with methanol, filtered and concentrated under reduced pressure, yielding a brown oil. The oil was diluted with ethyl acetate and washed successively with water, saturated ammonium chloride, water and brine. The ethyl acetate extract was dried with sodium sulfate, filtered and concentrated under reduced pressure. The solid was taken up in DMF (2 ml) and chromatographed using reverse-phase HPLC (Column: Waters XBridge 5µ, C18 19×200), yielding 3 (2.4 mg, 5.19 µmol, 15.22% yield) as a white solid. $^1$H NMR (500 MHz, DMSO-$d_6$) δ 8.21 (d, J=4.7 Hz, 1H), 7.17-7.09 (m, 2H), 7.04 (br. s., 1H), 6.96 (t, J=8.8 Hz, 2H), 6.76 (d, J=4.7 Hz, 1H), 3.84 (d, J=7.1 Hz, 1H), 3.69 (d, J=9.8 Hz, 1H), 3.43 (br. s., 1H), 3.08 (t, J=11.3 Hz, 2H), 2.97-2.86 (m, 2H), 2.73 (s, 1H), 2.51 (br. s., 2H), 2.07 (s, 3H), 1.61 (br. s., 1H), 1.21 (d, J=12.5 Hz, 2H), 1.04-0.92 (m, 2H). MS(ES+) m/z 463.2 (M+H).

Example 4

N-(4-(3-(4-Fluorophenyl)-1-(4-methylbenzyl)-4-oxo-4,5,6,7-tetrahydro-1H-pyrrolo[3,2-c]pyridin-2-yl)pyridin-2-yl)acetamide

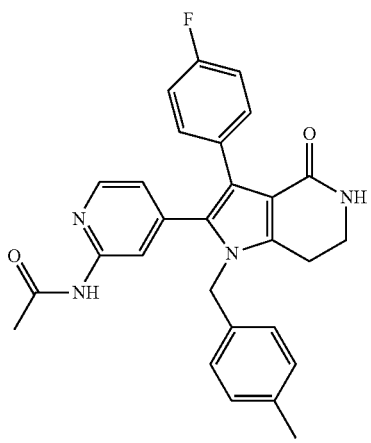 [SMILES: CC(=O)Nc1cc(-c2c(-c3ccc(F)cc3)c3c(n2Cc2ccc(C)cc2)CCNC3=O)ccn1]

4A: tert-Butyl 2-(2-acetamidopyridin-4-yl)-3-(4-fluorophenyl)-4-oxo-6,7-dihydro-1H-pyrrolo[3,2-c]pyridine-5(4H)-carboxylate: The compound was prepared starting from 3E (485 mg, 1.098 mmol) and acetamide (130 mg, 2.195 mmol) using the procedure for Example 3, yielding 4A (386.0 mg, 0.833 mmol, 75.86% yield) as a white solid. MS(ESI) m/z 465.3 (M+H).

4B: N-(4-(3-(4-Fluorophenyl)-4-oxo-4,5,6,7-tetrahydro-1H-pyrrolo[3,2-c]pyridin-2-yl)pyridin-2-yl)acetamide: To a DCM (5.4 ml) solution of 4A (125 mg, 0.269 mmol), TFA (99 µl, 1.346 mmol) was added dropwise. The solution was stirred at rt for 1 h. The reaction was concentrated under reduced pressure, yielding a brown oil. The oil was diluted with ethyl acetate and washed successively with 1.5 M potassium phosphate, dibasic, water, and brine. The ethyl acetate extract was dried with sodium sulfate, filtered and concentrated under reduced pressure yielding 4B (91 mg, 0.250 mmol, 93% yield) as a faint yellow solid. MS(ESI) m/z 365.2 (M+H).

Example 4: The compound was prepared starting from 4B (20 mg, 0.055 mmol) and 1-(bromomethyl)-4-methylbenzene (15.24 mg, 0.082 mmol) using the procedure for Example 3F. The solid was taken up in DMF (2 ml) and chromatographed using reverse-phase HPLC (Column: Waters XBridge 5µ C18 19×200), yielding N-(4-(3-(4-fluorophenyl)-1-(4-methylbenzyl)-4-oxo-4,5,6,7-tetrahydro-1H-pyrrolo[3,2-c]pyridin-2-yl)pyridin-2-yl)acetamide (2.1 mg, 4.26 µmol, 7.76% yield) as a white solid. $^1$H NMR (400 MHz, CD$_3$OD) δ 8.06 (dd, J=5.1, 0.7 Hz, 1H), 7.90 (s, 1H), 7.23-7.17 (m, 2H), 7.08 (d, J=7.7 Hz, 2H), 6.92-6.85 (m, 2H), 6.78 (d, J=7.9 Hz, 2H), 6.68 (dd, J=5.3, 1.5 Hz, 1H), 5.17 (s, 2H), 3.54 (t, J=6.9 Hz, 2H), 2.84 (t, J=6.9 Hz, 2H), 2.27 (s, 3H), 2.11 (s, 3H). MS(ESI) m/z 469.4 (M+H).

Example 5

3-([1,1'-Biphenyl]-3-yl)-2-(pyridin-4-yl)-1-((tetrahydro-2H-pyran-4-yl)methyl)-6,7-dihydro-1H-pyrrolo[3,2-c]pyridin-4(5H)-one

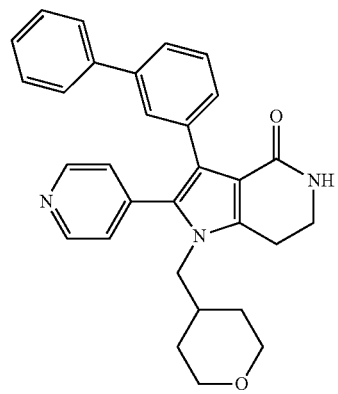 [SMILES: O=C1NCCc2c1c(-c1cccc(-c3ccccc3)c1)c(-c1ccncc1)n2CC1CCOCC1]

5A: tert-Butyl 3-bromo-4-oxo-2-(pyridin-4-yl)-1-((tetrahydro-2H-pyran-4-yl)methyl)-6,7-dihydro-1H-pyrrolo[3,2-c]pyridine-5(4H)-carboxylate: To a vial charged with 2A (0.624 g, 1.591 mmol) and 4-(bromomethyl)tetrahydropyran (0.427 g, 2.386 mmol) in DMF (3.98 ml) was added cesium carbonate (1.555 g, 4.77 mmol). The vial was capped and stirred at 75° C. ON. The reaction mixture was poured into a separatory funnel containing water and ethyl acetate. The aqueous layer was extracted with ethyl acetate (3×). The combined organics were washed with 10% lithium chloride solution (4×), dried over anhydrous sodium sulfate, filtered and concentrated in vacuo. The crude residue was purified by column chromatography on the Isco system (80 g, 0-10% MeOH/CH$_2$Cl$_2$) providing 5A (0.3973 g, 0.810 mmol, 50.9% yield). MS(ESI) m/z 490.3 (M+H).

Example 5: To a pressure relief vial charged with 5A (10 mg, 0.020 mmol), [1,1'-biphenyl]-3-ylboronic acid (8.08 mg, 0.041 mmol), and PdCl$_2$(dppf)-CH$_2$Cl$_2$ adduct (1.67 mg, 2.04 nmol) were added DMF (0.25 ml) and 2.0 M aqueous cesium carbonate (30.6 µl, 0.061 mmol). The suspension was purged with nitrogen for 5 min. The vial was sealed and heated at 105° C. for 75 min. The reaction was blown dry at 50° C. for 1 h. Dichloromethane (0.5 mL) was added followed by TFA (0.5 mL) and the reaction mixture was stirred at rt for 1 h. Excess solvent was removed by concentration in vacuo. The crude material was purified via preparative LCMS to yield 5 (5.6 mg, 60% yield). $^1$H NMR (500 MHz, DMSO-$d_6$) δ 8.54 (d, J=5.5 Hz, 2H), 7.44-7.35 (m, 6H), 7.34-7.28 (m, 1H), 7.24 (d, J=5.5 Hz, 2H), 7.21 (t, J=7.6 Hz, 1H), 7.09-7.04 (m, 2H), 3.85 (d, J=7.3 Hz, 2H), 3.68 (d, J=7.9 Hz, 2H), 3.06 (t, J=11.0 Hz, 2H), 2.93 (t, J=6.4 Hz, 2H), 1.54 (br. s., 1H), 1.20 (d, J=12.8 Hz, 2H), 1.02-0.89 (m, 2H). MS(ES+) m/z 464.2 (M+H).

Example 6

2-(2-Chloropyridin-4-yl)-1-(2-fluoro-4-(trifluoromethyl)benzyl)-3-(4-fluorophenyl)-6,7-dihydro-1H-pyrrolo[3,2-c]pyridin-4(5H)-one

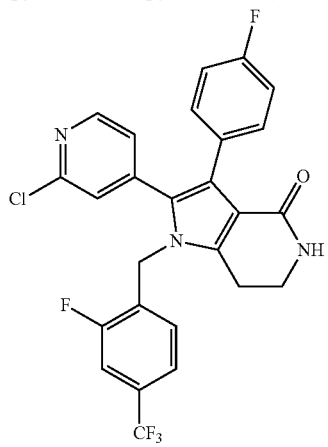 [SMILES: O=C1NCCc2c1c(-c1ccc(F)cc1)c(-c1ccnc(Cl)c1)n2Cc1ccc(C(F)(F)F)cc1F]

The compound was prepared starting from a suspension solution of 13A (20 mg, 0.059 mmol), 1-(bromomethyl)-2-fluoro-4-(trifluoromethyl)benzene (17.30 mg, 0.067 mmol) and $Cs_2CO_3$ (28.6 mg, 0.088 mmol) in DMF (1 mL) which was heated to 100° C. for 20 min under microwave conditions. The crude product was diluted with DMF and purified via preparative LCMS to isolate the final compound (17.4 mg, 0.034 mmol, 57% yield). $^1$H NMR (500 MHz, DMSO-$d_6$, water suppressed) δ 8.24 (d, J=5.0 Hz, 1H), 7.64 (d, J=9.8 Hz, 1H), 7.52 (d, J=7.7 Hz, 1H), 7.23-7.14 (m, 3H), 7.10 (s, 1H), 7.06-6.99 (m, 3H), 6.92 (t, J=7.7 Hz, 1H), 5.34 (s, 2H), 3.50-3.38 (m, 2H), 2.84 (t, J=6.6 Hz, 2H). MS(ESI) m/z 518.1 (M+H).

Example 7

N-(4-(1-(2-Fluoro-4-(trifluoromethyl)benzyl)-3-(4-fluorophenyl)-4-oxo-4,5,6,7-tetrahydro-1H-pyrrolo[3,2-c]pyridin-2-yl)pyridin-2-yl)isobutyramide

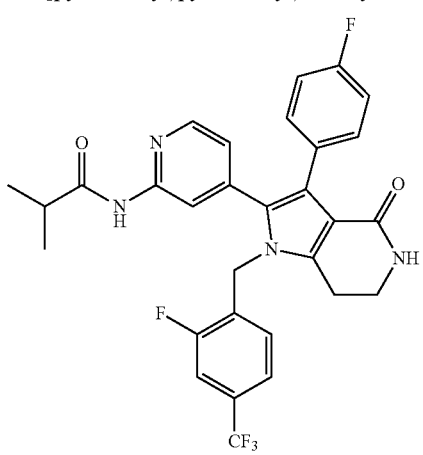

The compound was prepared starting from 6 (20 mg, 0.039 mmol) and isobutyramide (6.73 mg, 0.077 mmol) using the procedure for Example 3, yielding N-(4-(1-(2-fluoro-4-(trifluoromethyl)benzyl)-3-(4-fluorophenyl)-4-oxo-4,5,6,7-tetrahydro-1H-pyrrolo[3,2-c]pyridin-2-yl)pyridin-2-yl)isobutyramide (3.5 mg, 6.16 μmol, 15.94% yield) as a white solid. $^1$H NMR (500 MHz, DMSO-$d_6$) δ 8.10 (d, J=5.0 Hz, 1H), 7.67 (s, 1H), 7.54 (d, J=10.4 Hz, 1H), 7.49 (d, J=8.1 Hz, 1H), 7.18-7.12 (m, 2H), 7.06 (br. s., 1H), 6.96 (t, J=8.9 Hz, 2H), 6.87 (t, J=7.6 Hz, 1H), 6.64 (d, J=5.0 Hz, 1H), 5.23 (s, 2H), 3.44 (br. s., 2H), 2.82 (t, J=6.6 Hz, 2H), 2.60 (dt, J=13.6, 6.6 Hz, 1H), 0.97 (d, J=6.7 Hz, 6H). MS(ESI) m/z 569.3 (M+H).

Example 8

N-(4-(1-(2-Fluoro-4-(trifluoromethyl)benzyl)-3-(4-fluorophenyl)-4-oxo-4,5,6,7-tetrahydro-1H-pyrrolo[3,2-c]pyridin-2-yl)pyridin-2-yl)cyclopropanecarboxamide

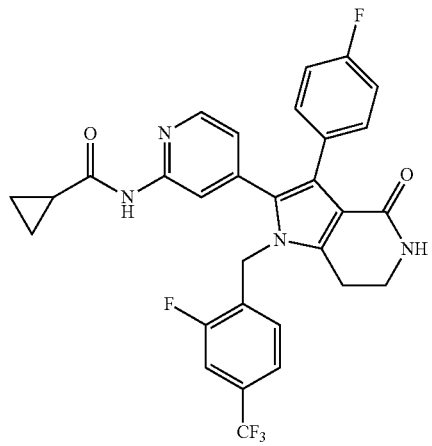 [SMILES: O=C1NCCc2c1c(-c1ccc(F)cc1)c(-c1ccnc(NC(=O)C3CC3)c1)n2Cc1ccc(C(F)(F)F)cc1F]

The compound was prepared starting from 6 (35 mg, 0.068 mmol) and cyclopropanecarboxamide (11.50 mg, 0.135 mmol) using the procedure for Example 3, yielding N-(4-(1-(2-fluoro-4-(trifluoromethyl)benzyl)-3-(4-fluorophenyl)-4-oxo-4,5,6,7-tetrahydro-1H-pyrrolo[3,2-c]pyridin-2-yl)pyridin-2-yl)cyclopropane carboxamide (3.0 mg, 5.30 μmol, 7.84% yield) as a white solid. $^1$H NMR (500 MHz, DMSO-$d_6$) δ 8.11 (d, J=5.0 Hz, 1H), 7.57 (d, J=10.1 Hz, 1H), 7.50 (d, J=8.1 Hz, 1H), 7.18-7.13 (m, 2H), 7.11 (br. s., 1H), 6.97 (t, J=8.8 Hz, 2H), 6.86 (t, J=7.6 Hz, 1H), 6.62 (d, J=5.0 Hz, 1H), 5.24 (s, 2H), 3.43-3.31 (m, 2H), 2.81 (t, J=6.6 Hz, 2H), 0.77-0.65 (m, 4H). MS(ESI) m/z 567.3 (M+H).

Example 9

5-Fluoro-2-((4-oxo-2-(pyridin-4-yl)-3-(4-(trifluoromethyl)phenyl)-4,5,6,7-tetrahydro-1H-pyrrolo[3,2-c]pyridin-1-yl)methyl)benzonitrile

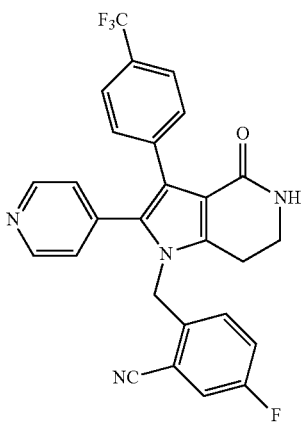 [SMILES: N#Cc1cc(F)ccc1Cn1c2c(c(-c3ccc(C(F)(F)F)cc3)c1-c1ccncc1)C(=O)NCC2]

9A: 3-Bromo-2-(pyridin-4-yl)-6,7-dihydro-1H-pyrrolo[3,2-c]pyridin-4(5H)-one: To a round bottom flask charged with 2A (0.45 g, 1.147 mmol) in dichloromethane (10.33 ml) was added TFA (1.147 ml). The reaction mixture was stirred at rt 2 h. Excess TFA was removed by concentration in vacuo. The crude residue was partitioned between ethyl acetate and saturated aqueous sodium bicarbonate. The aqueous layer was extracted with ethyl acetate (3×). The combined organics were dried over anhydrous sodium sulfate, filtered and concentrated in vacuo. The aqueous and organic layers were combined and concentrated in vacuo to remove the organics. Water was added and the solid was isolated by vacuum filtration. 3-Bromo-2-(pyridin-4-yl)-6,7-dihydro-1H-pyrrolo[3,2-c]pyridin-4(5H)-one (0.288 g, 0.986 mmol, 86% yield) was isolated as a tan solid. MS(ESI) m/z 292.2 (M+H).

9B: 2-((3-Bromo-4-oxo-2-(pyridin-4-yl)-4,5,6,7-tetrahydro-1H-pyrrolo[3,2-c]pyridin-1-yl)methyl)-5-fluorobenzonitrile: To a round bottom flask charged with 9A (0.288 g, 0.986 mmol) in DMF (6.57 ml) was added cesium carbonate (0.964 g, 2.96 mmol) and 2-(bromomethyl)-5-fluorobenzonitrile (0.232 g, 1.084 mmol). The reaction mixture was heated at 75° C. 8 h and cooled to rt ON. Additional reagents were added and heating continued 4 h. After cooling to rt, the reaction mixture was transferred to a separatory funnel containing 1:1 ethyl acetate and water. The aqueous layer was extracted with ethyl acetate (3×). The combined organics were washed with 10% lithium chloride solution (3×), dried over anhydrous sodium sulfate, filtered and concentrated in vacuo. 9B was isolated (0.259 g, 61% yield). MS(ESI) m/z 425.1 (M+H).

Example 9: To a vial charged with 9B (16 mg, 0.038 mmol) was added (4-(trifluoromethyl)phenyl)boronic acid (14.3 mg, 0.075 mmol), PdCl$_2$(dppf)-CH$_2$Cl$_2$ adduct (3.07 mg, 3.76 µmol), 2M potassium phosphate, tribasic solution (56.4 µL, 0.113 mmol) and DMF (0.4 mL). The vial was degassed with nitrogen, capped and heated at 90° C. for 1 h. After cooling to rt, the reaction mixture was purified by preparative LCMS. 5-Fluoro-2-((4-oxo-2-(pyridin-4-yl)-3-(4-(trifluoromethyl)phenyl)-4,5,6,7-tetrahydro-1H-pyrrolo[3,2-c]pyridin-1-yl)methyl)benzonitrile was isolated (6.2 mg, 33% yield). $^1$H NMR (500 MHz, DMSO-d$_6$) δ 8.48 (d, J=4.9 Hz, 2H), 7.81 (d, J=8.5 Hz, 1H), 7.56-7.47 (m, 3H), 7.36 (d, J=7.9 Hz, 2H), 7.25 (br. s., 1H), 7.13 (d, J=5.5 Hz, 2H), 6.87 (dd, J=8.2, 5.2 Hz, 1H), 5.39 (s, 2H), 2.85 (t, J=6.4 Hz, 2H) Note: CH$_2$ under water peak. MS(ESI) m/z 491.2 (M+H).

Example 10

1-(2-Fluoro-4-(trifluoromethyl)benzyl)-2-(2-(methylamino)pyridin-4-yl)-3-(4-(trifluoromethyl)phenyl)-6,7-dihydro-1H-pyrrolo[3,2-c]pyridin-4(5H)-one

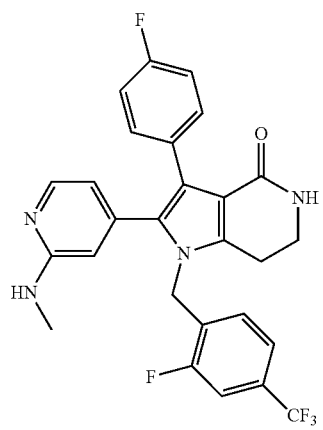 [SMILES: CNc1cc(-c2c(-c3ccc(F)cc3)c3c(n2Cc2ccc(C(F)(F)F)cc2F)CCNC3=O)ccn1]

A mixture of 6 (22 mg, 0.042 mmol) and methanamine 33% weight in ethanol (1999 µl, 14.87 mmol) was heated to 120° C. in a sealed tube for 16 h. After cooling to rt, the reaction mixture was purified by preparative LCMS producing the final compound (8.6 mg, 38% yield). $^1$H NMR (500 MHz, DMSO-d$_6$) δ 7.80 (d, J=4.7 Hz, 1H), 7.64 (d, J=9.8 Hz, 1H), 7.54 (d, J=7.4 Hz, 1H), 7.19 (br. s., 2H), 7.06 (br. s., 1H), 6.98 (t, J=8.4 Hz, 2H), 6.85 (t, J=7.2 Hz, 1H), 6.38 (d, J=4.0 Hz, 1H), 6.11 (d, J=4.4 Hz, 1H), 6.02 (br. s., 1H), 5.23 (br. s., 2H), 3.40 (br. s., 2H), 2.79-2.69 (m, 2H), 2.57 (d, J=3.4 Hz, 3H). MS(ESI) m/z 513.2 (M+H).

Example 11

2-((2-(2-Chloropyridin-4-yl)-4-oxo-3-(pyridin-3-yl)-4,5,6,7-tetrahydro-1H-pyrrolo[3,2-c]pyridin-1-yl)methyl)-5-fluorobenzonitrile

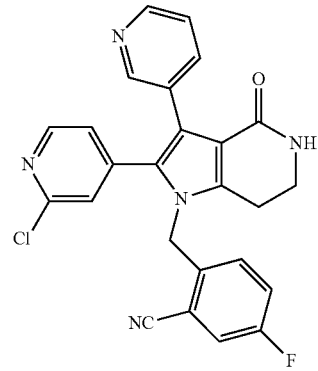 [SMILES: N#Cc1cc(F)ccc1Cn1c2c(c(-c3cccnc3)c1-c1ccnc(Cl)c1)C(=O)NCC2]

11A: 3-(Pyridin-3-yl)-6,7-dihydro-1H-pyrrolo[3,2-c]pyridin-4(5H)-one: A solution of piperidine-2,4-dione (2.16 g, 19.10 mmol), 2-amino-1-(pyridin-3-yl)ethanone, 2 HCl (3.99 g, 19.10 mmol) and potassium acetate (5.62 g, 57.3 mmol) in water (40 mL) was heated to 90° C. for 2 h. The reaction mixture was cooled down to rt and basified with 1.5M Na$_2$HPO$_4$ solution until ~pH 10. The solid product 3-(pyridin-3-yl)-6,7-dihydro-1H-pyrrolo[3,2-c]pyridin-4(5H)-one (3.473 g, 16.2 mmol, 85% yield) was isolated by filtration. $^1$H NMR (400 MHz, CD$_3$OD) δ 8.78 (dd, J=2.2, 0.7 Hz, 1H), 8.32 (dd, 1.5 Hz, 1H), 8.13 (dt, J=8.2, 1.8 Hz, 1H), 7.35 (ddd, J=7.9, 5.0, 0.8 Hz, 1H), 6.95 (s, 1H), 3.56 (t, J=6.9 Hz, 2H), 2.89 (t, J=6.9 Hz, 2H). MS(ESI) m/z 214.1 (M+H).

11B: 2-Bromo-3-(pyridin-3-yl)-6,7-dihydro-1H-pyrrolo[3,2-c]pyridin-4(5H)-one: To a suspension solution of 11A (3.71 g, 17.40 mmol) in DMF (70 mL) at 23° C. was added NBS (3.10 g, 17.40 mmol). The reaction mixture became homogeneous and was stirred for 20 min. The reaction mixture was concentrated and triturated in MeOH (20 mL). The solid product was collected and the triturant was concentrated in vacuo. Additional product was isolated by addition of 1N NaOH (5 mL) to the triturant residue and stirring for 10 min. The solid was collected and triturated in 5 mL of MeOH. The solid was collected by filtration and combined with the first batch to yield 11B (4.14 g, 14.2 mmol, 81% yield). $^1$H NMR (400 MHz, CD$_3$OD) δ 8.62 (dd, J=2.1, 0.7 Hz, 1H), 8.42 (dd, J=5.0, 1.7 Hz, 1H), 7.94 (dt, J=7.9, 1.9 Hz, 1H), 7.43 (ddd, 5.0, 0.7 Hz, 1H), 3.58 (t, J=7.0 Hz, 2H), 2.92-2.88 (m, 2H). MS(ESI) m/z 294.0 (M+H).

11C: 2-((2-Bromo-4-oxo-3-(pyridin-3-yl)-4,5,6,7-tetrahydro-1H-pyrrolo[3,2-c]pyridin-1-yl)methyl)-5-fluorobenzonitrile: A suspension solution of 11B (300 mg, 1.027 mmol), 2-(bromomethyl)-5-fluorobenzonitrile (261 mg, 1.181 mmol) and Cs$_2$CO$_3$ (502 mg, 1.540 mmol) in DMF (4 mL) was heated to 100° C. for 20 min under microwave conditions, after which it was concentrated to give a brown oil. The oil was dissolved EtOAc (100 mL) and washed with 10% LiCl solution (20 mL), brine (20 mL) and dried over Na$_2$SO$_4$. The organics were concentrated in vacuo. The crude product was purified by column chromatography on the Isco system (5% MeOH/CH$_2$Cl$_2$) to yield 11C (212 mg, 0.499 mmol, 49% yield). $^1$H NMR (400 MHz, CD$_3$OD) δ 8.62 (dd, J=2.2, 0.7 Hz, 1H), 8.43 (dd, J=5.0, 1.7 Hz, 1H), 7.94 (dt, J=7.9, 1.9 Hz, 1H), 7.67 (dd, J=8.3, 2.8 Hz, 1H), 7.50-7.41 (m, 2H), 6.96 (dd, J=8.8, 5.1 Hz, 1H), 5.54 (s, 2H), 3.58 (t, J=7.0 Hz, 2H), 2.89 (t, J=6.9 Hz, 2H). MS(ESI) m/z 425.2 (M+H).

Example 11: A degassed solution of 11C (15 mg, 0.035 mmol), 2-chloro-4-(4,4,5,5-tetramethyl-1,3,2-dioxaborolan-2-yl)pyridine (16.90 mg, 0.071 mmol), PdCl$_2$(dppf)-CH$_2$Cl$_2$ adduct (2.88 mg, 3.53 nmol) and potassium phosphate tribasic 2M solution (0.053 mL, 0.106 mmol) in DMF (0.5 mL) was heated to 90° C. for 1 h. The crude reaction mixture was purified by preparative LCMS to yield the final compound (3.1 mg, 6.57 nmol, 19% yield). $^1$H NMR (500 MHz, DMSO-d$_6$, water suppressed) δ 8.35 (d, J=3.7 Hz, 1H), 8.31 (s, 1H), 8.22 (d, J=5.0 Hz, 1H), 7.78 (dd, J=8.4, 2.4 Hz, 1H), 7.62 (d, J=7.7 Hz, 1H), 7.47 (td, J=8.5, 2.5 Hz, 1H), 7.28 (dd, J=7.6, 4.9 Hz, 1H), 7.22 (br. s., 1H), 7.17 (s, 1H), 7.00 (d, J=4.7 Hz, 1H), 6.88 (dd, J=8.8, 5.4 Hz, 1H), 5.38 (s, 2H), 3.50-3.42 (m, J=4.4 Hz, 2H), 2.86 (t, J=6.7 Hz, 2H). MS(ESI) m/z 458.1 (M+H).

Example 12

2-(2-Aminopyridin-4-yl)-1-(2-fluoro-4-(trifluoromethyl)benzyl)-3-(4-fluorophenyl)-6,7-dihydro-1H-pyrrolo[3,2-c]pyridin-4(5H)-one

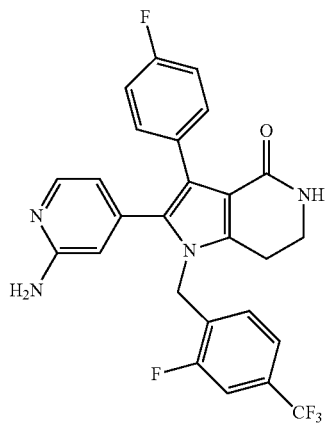 [SMILES: Nc1cc(-c2c(-c3ccc(F)cc3)c3c(n2Cc2ccc(C(F)(F)F)cc2F)CCNC3=O)ccn1]

12A: tert-Butyl(4-(1-(2-fluoro-4-(trifluoromethyl)benzyl)-3-(4-fluorophenyl)-4-oxo-4,5,6,7-tetrahydro-1H-pyrrolo[3,2-c]pyridin-2-yl)pyridin-2-yl)carbamate: To a reaction vial charged with 6 (0.19 g, 0.367 mmol), tert-butyl carbamate (0.086 g, 0.734 mmol), tris(dibenzylideneacetone)dipalladium(O) (0.067 g, 0.073 mmol), cesium carbonate (0.239 g, 0.734 mmol), and Xantphos (0.042 g, 0.073 mmol) was added dioxane (1.468 ml). The suspension was purged with nitrogen for 5 minutes, sealed and heated to 110° C. for 1 h. The reaction was diluted with methanol, filtered and concentrated under reduced pressure, yielding a brown oil. The crude residue was purified by column chromatography on the Isco system (12 g, 0-10% MeOH/CH$_2$Cl$_2$). Additional purification was done by preparative HPLC on the neutral system. Material carried forward as is.

Example 12: To a round bottom flask charged with tert-butyl (4-(1-(2-fluoro-4-(trifluoromethyl)benzyl)-3-(4-fluorophenyl)-4-oxo-4,5,6,7-tetrahydro-1H-pyrrolo[3,2-c]pyridin-2-yl)pyridin-2-yl)carbamate (12 mg, 0.020 mmol) in dichloromethane (80 μl) was added TFA (20.05 μl). The reaction mixture stirred at rt 3 h. Solvent and excess TFA were removed under vacuum. The crude residue was taken up in methanol and free based using a PHENOMENEX® Strata 1 g column. The column was flushed with 3 column volumes methanol and 1 column volume 7 N NH$_3$/MeOH. The ammonia-containing fraction was concentrated in vacuo. The crude product was purified via preparative LCMS. $^1$H NMR (500 MHz, DMSO-d$_6$, water suppressed) δ 7.74 (d, J=5.0 Hz, 1H), 7.65 (d, J=10.1 Hz, 1H), 7.54 (d, J=7.7 Hz, 1H), 7.24-7.16 (m, 2H), 7.08 (br. s., 1H), 6.99 (t, J=8.8 Hz, 2H), 6.83 (t, J=7.6 Hz, 1H), 6.12 (d, J=5.0 Hz, 1H), 6.16-6.10 (m, 1H), 6.09 (s, 1H), 5.92 (br. s., 1H), 5.24 (br. s., 2H), 3.41 (br. s., 2H), 2.76-2.68 (m, 2H). MS(ESI) m/z 499.3 (M+H).

Example 13

3-(4-Fluorophenyl)-1-(4-(3-methyl-1,2,4-oxadiazol-5-yl)benzyl)-2-(pyridin-4-yl)-6,7-dihydro-1H-pyrrolo[3,2-c]pyridin-4(5H)-one

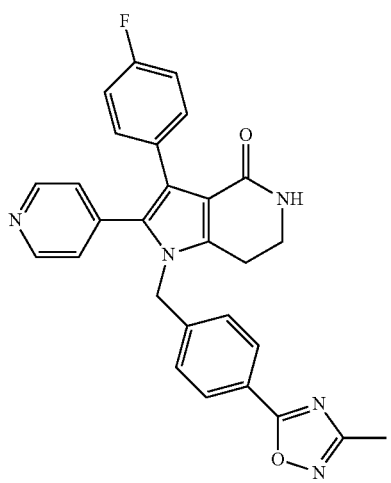 [SMILES: Cc1noc(-c2ccc(Cn3c4c(c(-c5ccc(F)cc5)c3-c3ccncc3)C(=O)NCC4)cc2)n1]

13A: 2-(2-Chloropyridin-4-yl)-3-(4-fluorophenyl)-6,7-dihydro-1H-pyrrolo[3,2-c]pyridin-4(5H)-one: To a round bottom flask charged with 3C (1.235 g, 3.78 mmol), (4-fluorophenyl)boronic acid (0.635 g, 4.54 mmol), and PdCl$_2$(dppf)-CH$_2$Cl$_2$ adduct (0.309 g, 0.378 mmol) were added dioxane (25.2 ml) and potassium phosphate, tribasic (2M in H$_2$O, 5.67 ml, 11.34 mmol). The suspension was purged with nitrogen for 5 minutes. The reaction mixture was heated to 75° C. for 30 min. After cooling to rt, the reaction was diluted methanol, filtered and concentrated under reduced pressure, yielding a dark oil. The crude oil was purified by column chromatography on the Isco system (40 g, 0-10% MeOH/CH$_2$Cl$_2$). 13A (1.015 g, 2.97 mmol, 79% yield) was isolated as a tan solid. MS(ESI) m/z 342.2 (M+H).

13B: 3-(4-Fluorophenyl)-2-(pyridin-4-yl)-6,7-dihydro-1H-pyrrolo[3,2-c]pyridin-4(5H)-one: To a flask charged with 13A (1.015 g, 2.97 mmol) in methanol and flushed with nitrogen, was added 10% Pd/C-Degussa Type (200 mg, 1.879 mmol) under nitrogen. 1 N Hydrochloric acid (2.97 ml, 2.97 mmol) was added. The reaction was evacuated and purged with hydrogen (4×). The suspension was stirred under hydrogen 2 d. Recharged the flask (3× evacuate and purge) with hydrogen and stirred 6 h. After sparging reaction with nitrogen, additional 10% Pd/C-Degussa Type (200 mg, 1.879 mmol) was added, and the reaction mixture was sparged with hydrogen (3× evacuate and purge). Stirring continued 3 h at rt. The reaction mixture was diluted with methanol to get all the product into solution, filtered through a pad of CELITE®, and concentrated under reduced pressure. The desired 3-(4-fluorophenyl)-2-(pyridin-4-yl)-6,7-dihydro-1H-pyrrolo[3,2-c]pyridin-4(5H)-one, 2 HCl (1.07 g, 2.81 mmol, 95% yield) was obtained as a yellow solid. MS(ESI) m/z 308.2 (M+H).

Example 13: A vial was charged with 13B (14 mg, 0.046 mmol) in DMF (0.5 mL). Cesium carbonate (44.5 mg, 0.137 mmol) and 5-(4-(bromomethyl)phenyl)-3-methyl-1,2,4-oxadiazole (23.06 mg, 0.091 mmol) were added. The reaction mixture was stirred ON at rt. The crude sample was diluted with DMF and directly purified via preparative LCMS to yield 9.75 (5.6 mg, 0.012 mmol, 26% yield). $^1$H NMR (500 MHz, DMSO-d$_6$, water suppressed) δ 8.41 (br. s., 2H), 8.01 (d, J=8.1 Hz, 2H), 7.21-7.10 (m, 5H), 7.05-6.94 (m, 4H), 5.28 (br. s., 2H), 3.47-3.29 (m, 2H), 2.77 (t, J=6.4 Hz, 2H), 2.39 (s, 3H). MS(ESI) m/z 480.2 (M+H).

Example 14

5-Fluoro-2-((4-oxo-2-(pyridin-4-yl)-3-(thiophen-2-yl)-4,5,6,7-tetrahydro-1H-pyrrolo[3,2-c]pyridin-1-yl)methyl)benzonitrile

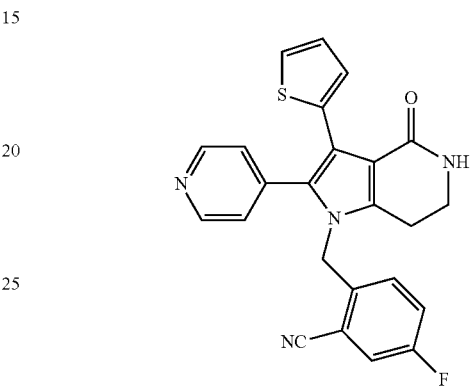

14A: 2-(Pyridin-4-yl)-6,7-dihydro-1H-pyrrolo[3,2-c]pyridin-4(5H)-one: To a flask charged with 3B (3 g, 12.11 mmol) in methanol and flushed with nitrogen, was added 10% Pd/C-Degussa Type (0.3 g, 2.82 mmol) under nitrogen. 1 N Hydrochloric acid (12.11 ml, 12.11 mmol) was added. The reaction was evacuated and purged with hydrogen (3×). The suspension was stirred under hydrogen 4 h. The reaction was evacuated and purged with nitrogen. The reaction was diluted with significant methanol (100 ml) to get all the product into solution, at which point the reaction mixture was filtered through CELITE®, and the filtrate was concentrated under reduced pressure. The desired 2-(pyridin-4-yl)-6,7-dihydro-1H-pyrrolo[3,2-c]pyridin-4(5H)-one, 2 HCl (3.17 g, 11.08 mmol, 91% yield) was obtained as a pale yellow solid. $^1$H NMR (400 MHz, DMSO-d$_6$) δ 12.67 (br. s., 1H), 8.70 (d, J=7.0 Hz, 2H), 8.16 (d, J=6.8 Hz, 2H), 7.58 (d, J=2.3 Hz, 1H), 7.29 (br. s., 1H), 3.47-3.40 (m, 2H), 2.92 (t, J=6.8 Hz, 2H). MS(ESI) m/z 214.2 (M+H).

14B: 5-Fluoro-2-((4-oxo-2-(pyridin-4-yl)-4,5,6,7-tetrahydro-1H-pyrrolo[3,2-c]pyridin-1-yl)methyl)benzonitrile: To a round bottom flask charged with 14A (2.667 g, 10.68 mmol), cesium carbonate (10.44 g, 32.0 mmol) and 2-(bromomethyl)-5-fluorobenzonitrile (2.51 g, 11.75 mmol), DMF (42.7 ml) was added. The reaction mixture was heated at 75° C. 2 h. The reaction mixture was diluted with water and ethyl acetate. The aqueous layer was extracted with ethyl acetate (3×). The combined organics were washed with 10% lithium chloride solution, dried over anhydrous sodium sulfate, filtered and concentrated in vacuo. The crude residue was purified by column chromatography on the Isco system (40 g, 0-10% MeOH/CH$_2$Cl$_2$). 5-Fluoro-2-((4-oxo-2-(pyridin-4-yl)-4,5,6,7-tetrahydro-1H-pyrrolo[3,2-c]pyridin-1-yl)methyl)benzonitrile (1.115 g, 3.22 mmol, 30.1% yield) was isolated. MS(ESI) m/z 347.2 (M+H).

14C: 2-((3-Bromo-4-oxo-2-(pyridin-4-yl)-4,5,6,7-tetrahydro-1H-pyrrolo[3,2-c]pyridin-1-yl)methyl)-5-fluorobenzonitrile: To a round bottom flask charged with 14B (28 mg, 0.081 mmol) in DMF (0.35 ml) was added NBS (15 mg, 0.085 mmol). The reaction mixture was stirred at rt ON. Water (5 mL) was added and a solid precipitated as the water was being added. The slurry was stirred at rt for 30 min and filtered. The filtrate was transferred to a separatory funnel and extracted with ethyl acetate (3×). The combined organics were washed with 10% lithium chloride solution (3×), dried over anhydrous sodium sulfate, filtered and concentrated in vacuo. 2-((3-Bromo-4-oxo-2-(pyridin-4-yl)-4,5,6,7-tetrahydro-1H-pyrrolo[3,2-c]pyridin-1-yl)methyl)-5-fluorobenzonitrile (23 mg, 0.054 mmol, 66.9% yield) was isolated as a white solid. MS(ESI) m/z 425.2 (M+H).

Example 14: To a vial charged with 14C (14 mg, 0.033 mmol) in DMF (0.4 mL) was added $PdCl_2(dppf)$-$CH_2Cl_2$ adduct (2.69 mg, 3.29 µmol), thiophen-2-ylboronic acid (8.4 mg, 0.066 mmol) and tripotassium phosphate (2M in $H_2O$, 49.4 µl, 0.099 mmol). The vial was capped, degassed and purged with nitrogen (3×), and heated at 90° C. 1 h. After cooling to rt, the reaction mixture was diluted with DMF and purified by preparative LCMS to yield the final compound (5.3 mg, 0.012 mmol, 38% yield). $^1$H NMR (500 MHz, DMSO-$d_6$, water suppressed) δ 8.44 (br. s., 2H), 7.73 (dd, J=8.4, 2.4 Hz, 1H), 7.47 (td, J=8.4, 2.4 Hz, 1H), 7.26 (d, J=4.7 Hz, 1H), 7.15 (br. s., 1H), 7.11-7.04 (m, 3H), 6.87-6.83 (m, 1H), 6.81 (dd, J=8.6, 5.2 Hz, 1H), 5.27 (s, 2H), 3.43 (br. s., 2H), 2.82 (t, J=6.6 Hz, 2H). MS(ESI) m/z 429.2 (M+H).

The following compounds in Table 1 were made in a similar manner as Example 1:

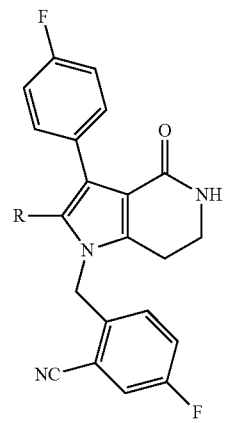

TABLE 1

| Ex. No. | R | M + H | $^1$H NMR: (500 MHz, DMSO-$d_6$) |
|---|---|---|---|
| 15 | 4-methyl-3-methoxypyridine | 471.2 | δ 7.69 (d, J = 8.1 Hz, 1H), 7.46 (d, J = 8.4 Hz, 1H), 7.26 (s, 1H), 7.15 (s, 1H), 7.09 (d, J = 5.7 Hz, 2H), 7.05 (s, 1H), 6.92 (t, J = 8.8 Hz, 2H), 6.86 (d, J = 8.1 Hz, 1H), 6.77 (br. s., 1H), 5.28-5.08 (m, 2H), 3.69 (s, 3H), 3.45 (br, s., 2H), 2.92-2.82 (m, 2H) |
| 16 | 2-(trifluoromethyl)pyridin-4-yl | 509.1 | δ 8.57 (d, J = 4.7 Hz, 1H), 7.75 (d, J = 7.4 Hz, 1H), 7.53-7.40 (m, 1H), 7.34-7.26 (m, 2H), 7.18-7.08 (m, 3H), 6.99 (t, J = 8.8 Hz, 2H), 6.88 (dd, J = 8.6, 5.2 Hz, 1H), 5.39 (s, 2H), 3.46 (br. s., 2H), 2.91-2.81 (m, 2H) |
| 17 | pyrimidin-5-yl | 442.2 | δ 9.01 (s, 1H), 8.43 (s, 2H), 7.76 (d, J = 8.4 Hz, 1H), 7.52-7.42 (m, 1H), 7.19-7.13 (m, 3H), 6.97 (t, J = 8.8 Hz, 2H), 6.88 (dd, J = 8.6, 5.2 Hz, 1H), 5.33 (s, 2H), 3.45 (br. s., 2H), 2.93-2.80 (m, 2H) |
| 18 | 2-fluoropyridin-4-yl | 459.2 | δ 8.01 (d, J = 5.0 Hz, 1H), 7.73 (d, J = 6.4 Hz, 1H), 7.50-7.42 (m, 1H), 7.17-7.09 (m, 3H), 6.98 (t, J = 8.9 Hz, 2H), 6.88-6.80 (m, 3H), 5.37 (s, 2H), 3.48-3.40 (m, 2H), 2.84 (t, J = 6.7 Hz, 2H) |
| 19 | 1H-indol-5-yl | 479.2 | (water suppressed) δ 11.15 (br. s., 1H), 7.78-7.72 (m, 1H), 7.56-7.48 (m, 1H), 7.31 (br. s., 1H), 7.27-7.15 (m, 4H), 7.04 (br. s., 1H), 6.87 (t, J = 8.9 Hz, 2H), 6.80 (dd, J = 8.6, 5.2 Hz, 1H), 6.72 (d, J = 8.1 Hz, 1H), 6.30 (br. s., 1H), 5.20 (s, 2H), 3.47-3.34 (m, 2H), 2.75 (br. s., 2H) |
| 20 | 2-methylpyridin-4-yl | 455.2 | (water suppressed) δ 8.38 (d, J = 5.4 Hz, 1H), 7.80 (d, J = 6.1 Hz, 1H), 7.53-7.46 (m, 1H), 7.42 (br. s., 1H), 7.26-7.14 (m, 3H), 7.02 (t, J = 8.9 Hz, 2H), 6.96 (d, J = 5.4 Hz, 1H), 6.86 (dd, J = 8.6, 5.2 Hz, 1H), 5.44 (s, 2H), 3.43 (d, J = 4.4 Hz, 2H), 2.85 (t, J = 6.6 Hz, 2H), 2.48 (br. s., 3H) |

TABLE 1-continued

| Ex. No. | R | M + H | ¹H NMR: (500 MHz, DMSO-d$_6$) |
|---|---|---|---|
| 21 | 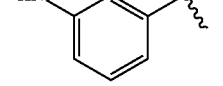 | 497.3 | (water suppressed) δ 9.86 (s, 1H), 7.75 (d, J = 5.7 Hz, 1H), 7.54-7.38 (m, 2H), 7.29 (s, 1H), 7.21-7.09 (m, 3H), 6.92 (t, J = 8.8 Hz, 2H), 6.83-6.75 (m, 1H), 6.63 (d, J = 7.4 Hz, 1H), 5.21 (s, 2H), 3.42 (d, J = 10.1 Hz, 2H), 2.79 (t, J = 6.4 Hz, 2H), 1.96 (s, 3H) |
| 22 | 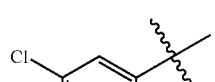 | 475.2 | (water suppressed) δ 8.20 (d, J = 5.0 Hz, 1H), 7.79 (d, J = 8.4 Hz, 1H), 7.52-7.46 (m, 1H), 7.16 (br. s., 3H), 7.11 (s, 1H), 7.04-6.97 (m, 2H), 6.95 (d, J = 4.7 Hz, 1H), 6.89-6.81 (m, 1H), 5.37 (s, 2H), 3.45 (d, J = 7.7 Hz, 2H), 2.84 (t, J = 6.4 Hz, 2H) |
| 23 | 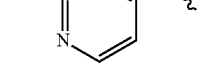 | 430.2 | (water suppressed) δ 7.84 (dd, J = 8.4, 2.4 Hz, 1H), 7.58 (s, 1H), 7.56-7.50 (m, 1H), 7.47 (s, 1H), 7.29-7.22 (m, 2H), 7.05 (br. s., 1H), 7.03-6.94 (m, 2H), 6.81 (dd, J = 8.6, 5.2 Hz, 1H), 6.07 (s, 1H), 5.27 (s, 2H), 3.40 (d, J = 6.1 Hz, 2H), 2.78 (t, J = 6.6 Hz, 2H) |
| 24 | 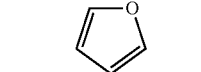 | 444.3 | (water suppressed) δ 7.83 (dd, J = 8.2, 2.2 Hz, 1H), 7.53 (td, J = 8.4, 2.4 Hz, 1H), 7.49 (s, 1H), 7.26-7.20 (m, 2H), 7.02 (br. s., 1H), 7.00-6.94 (m, 3H), 6.82 (dd, J = 8.6, 5.2 Hz, 1H), 5.21 (s, 2H), 3.72 (s, 3H), 3.39 (br. s., 2H), 2.76 (t, J = 6.4 Hz, 2H) |
| 25 |  | 446.2 | (water suppressed) δ 7.79 (d, J = 6.7 Hz, 1H), 7.50 (t, J = 7.9 Hz, 1H), 7.42 (br. s., 1H), 7.24 (br. s., 1H), 7.19 (t, J = 6.7 Hz, 2H), 7.06 (br. s., 1H), 6.95 (t, J = 8.8 Hz, 2H), 6.84-6.77 (m, 1H), 6.62 (d, J = 4.7 Hz, 1H), 5.25 (s, 2H), 3.40 (br. s., 2H), 2.79 (t, J = 6.2 Hz, 2H) |
| 26 | 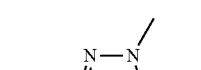 | 472.2 | (water suppressed) δ 8.24 (s, 2H), 7.82 (d, J = 6.1 Hz, 1H), 7.54-7.47 (m, 1H), 7.21-7.16 (m, 2H), 7.12 (br. s., 1H), 6.99 (t, J = 8.8 Hz, 2H), 6.88 (dd, J = 8.4, 5.0 Hz, 1H), 5.28 (s, 2H), 3.85 (s, 3H), 3.47-3.35 (m, 2H), 2.82 (t, J = 6.4 Hz, 2H) |
| 27 | 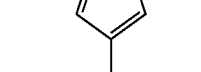 | 459.3 | (500 MHz, CD$_3$OD) δ 8.34 (d, J = 1.0 Hz, 1H), 8.21 (d, J = 4.9 Hz, 1H), 7.46 (dd, J = 8.1, 2.7 Hz, 1H), 7.32 (td, J = 8.5, 2.7 Hz, 1H), 7.21-7.14 (m, 2H), 7.13-7.07 (m, 1H), 6.93-6.83 (m, 3H), 5.35 (br s, 2H), 3.63 (t, J = 7.0 Hz, 2H), 2.99 (s, 2H) |

The following Examples in Table 2 were made in a similar manner as Example 2 and/or Example 13:

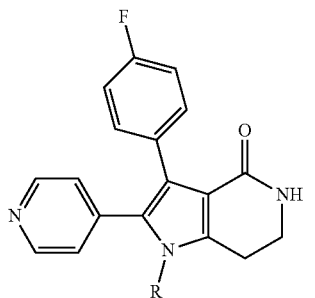

TABLE 2

| Ex. No. | R | M + H | ¹H NMR |
|---|---|---|---|
| 28 | 4-CN-benzyl-CH₂- (structure) | 423.1 | (500 MHz, CDCl₃) δ 8.51-8.46 (m, 2H), 7.70-7.65 (m, 2H), 7.26-7.20 (m, 2H), 7.06 (d, J = 8.4 Hz, 2H), 6.95-6.90 (m, 4H), 5.42 (br. s., 1H), 5.16 (s, 2H), 3.61 (td, J = 6.8, 2.7 Hz, 2H), 2.77 (t, J = 6.8 Hz, 2H) |
| 29 | cyclohexenyl (structure) | 388.1 | (500 MHz, CD₃OD) δ 8.26 (d, J = 7.3 Hz, 2H), 7.54 (d, J = 7.2 Hz, 2H), 7.38-7.32 (m, 2H), 7.18-7.11 (m, 2H), 6.37-6.31 (m, 1H), 5.74 (dd, J = 10.0, 2.4 Hz, 1H), 5.04 (br. s., 1H), 3.56 (t, J = 6.9 Hz, 2H), 2.97 (t, J = 6.8 Hz, 2H), 2.31-2.21 (m, 2H), 2.21-2.16 (m, 1H), 1.89-1.80 (m, 1H), 1.76 (quin, J = 5.9 Hz, 2H) |
| 30 | 4-piperidinyl-CH₂- (structure) | 405.2 | (500 MHz, CD₃OD) δ 8.51-8.47 (m, 2H), 7.28-7.24 (m, 2H), 7.18-7.13 (m, 2H), 6.93-6.86 (m, 2H), 3.95 (d, J = 7.6 Hz, 2H), 3.61 (t, J = 6.9 Hz, 2H), 3.02 (t, J = 6.9 Hz, 2H), 2.92 (d, J = 12.4 Hz, 2H), 2.37 (td, J = 12.4, 2.3 Hz, 2H), 1.51 (ddd, J = 11.3, 7.6, 3.7 Hz, 1H), 1.36 (d, J = 11.6 Hz, 2H), 0.97 (qd, J = 12.3, 4.1 Hz, 2H) |
| 31 | tetrahydropyran-4-yl-CH₂- (structure) | 406.1 | (500 MHz, DMSO-d₆) δ 8.56-8.51 (m, 2H), 7.21-7.17 (m, 2H), 7.15-7.10 (m, 2H), 7.09 (br. s., 1H), 7.00-6.92 (m, 2H), 3.86 (d, J = 7.6 Hz, 2H), 3.70 (dd, J = 11.1, 2.9 Hz, 2H), 3.44 (td, J = 6.6, 2.6 Hz, 2H), 3.07 (t, J = 10.8 Hz, 2H), 2.97-2.89 (m, 2H), 1.53 (td, J = 7.5, 4.0 Hz, 1H), 1.20 (d, J = 10.7 Hz, 2H), 0.95 (qd, J = 12.2, 4.1 Hz, 2H) |
| 32 | 3-piperidinyl (structure) | 405.1 | (500 MHz, DMSO-d₆) δ 8.56-8.50 (m, 2H), 7.22-7.16 (m, 2H), 7.16-7.11 (m, 2H), 7.08 (br. s., 1H), 6.98 (t, J = 9.0 Hz, 2H), 3.85 (t, J = 6.9 Hz, 3H), 3.44 (d, J = 2.4 Hz, 2H), 3.44-3.42 (m, 2H), 2.95-2.85 (m, 2H), 2.73-2.65 (m, 1H), 2.31 (t, J = 10.2 Hz, 1H), 2.02-1.94 (m, 1H), 1.38 (br. s., 3H), 1.20-1.10 (m, 1H), 0.88-0.79 (m, 1H) |
| 33 | 4-CF₃-benzyl-CH₂- (structure) | 466.1 | (500 MHz, DMSO-d₆) δ 8.42 (d, J = 5.5 Hz, 2H), 7.67 (d, J = 8.5 Hz, 2H), 7.17 (dd, J = 8.5, 6.1 Hz, 2H), 7.11 (d, J = 7.9 Hz, 3H), 7.04-6.95 (m, 4H), 5.27 (s, 2H), 3.41-3.39 (m, 2H), 2.78-2.70 (m, 2H) |
| 34 | 2-CN-4-F-benzyl-CH₂- (structure) | 441.1 | (500 MHz, DMSO-d₆) δ 8.39 (d, J = 5.5 Hz, 2H), 7.78 (dd, J = 8.5, 3.1 Hz, 1H), 7.49 (td, J = 8.7, 2.7 Hz, 1H), 7.17-7.12 (m, 3H), 7.01-6.93 (m, 4H), 6.81 (dd, J = 8.9, 5.2 Hz, 1H), 5.34 (s, 2H), 3.47-3.41 (m, 2H), 2.82 (t, J = 6.7 Hz, 2H) |
| 35 | 3-CN-4-F-benzyl-CH₂- (structure) | 441.1 | (500 MHz, DMSO-d₆) δ 8.43 (d, J = 6.1 Hz, 2H), 7.49-7.40 (m, 2H), 7.21 (t, J = 6.1 Hz, 1H), 7.16 (dd, J = 8.5, 5.5 Hz, 2H), 7.12 (br. s., 1H), 7.06-7.00 (m, 2H), 6.97 (t, J = 8.9 Hz, 2H), 5.18 (s, 2H), 3.42 (d, J = 2.4 Hz, 2H), 2.78 (t, J = 6.7 Hz, 2H) |
| 36 | α-methylbenzyl (structure) | 412.2 | (500 MHz, DMSO-d₆) δ 8.50 (d, J = 5.5 Hz, 2H), 7.41-7.34 (m, 2H), 7.32-7.27 (m, 1H), 7.18 (d, J = 5.5 Hz, 2H), 7.16-7.08 (m, 4H), 7.04 (br. s., 1H), 6.96 (t, J = 8.9 Hz, 2H), 5.32 (q, J = 6.7 Hz, 1H), 3.29-3.22 (m, J = 6.1 Hz, 1H), 3.19-3.08 (m, J = 12.8 Hz, 1H), 2.80-2.70 (m, 1H), 2.11 (dt, J = 16.2, 5.6 Hz, 1H), 1.81 (d, J = 6 7 Hz, 3H) |
| 37 | 4-OMe-phenethyl (structure) | 442.2 | (500 MHz, DMSO-d₆) δ 8.50 (d, J = 5.5 Hz, 2H), 7.13-7.06 (m, 4H), 7.02-6.93 (m, 3H), 6.83-6.74 (m, 4H), 4.03 (t, J = 7.3 Hz, 2H), 3.69 (s, 3H), 3.31-3.26 (m, 2H), 2.69 (t, J = 6.7 Hz, 2H), 2.60 (t, J = 7.0 Hz, 2H) |

TABLE 2-continued

| Ex. No. | R | M + H | ¹H NMR |
|---|---|---|---|
| 38 | 4-methoxybenzyl | 428.1 | (500 MHz, DMSO-d$_6$) δ 8.52 (d, J = 4.9 Hz, 2H), 7.21 (d, J = 6.1 Hz, 2H), 7.16 (dd, J = 8.5, 5.5 Hz, 2H), 7.13 (br. s., 1H), 7.02-6.96 (m, 2H), 6.88-6.79 (m, 4H), 5.14 (s, 2H), 3.69 (s, 3H), 3.39 (d, J = 6.1 Hz, 2H), 2.78 (t, J = 6.7 Hz, 2H) |
| 39 | 4-tert-butylbenzyl | 452.2 | (500 MHz, DMSO-d$_6$) δ 8.52 (d, J = 4.9 Hz, 2H), 7.31 (d, J = 8.5 Hz, 2H), 7.22-7.15 (m, 4H), 7.13 (s, 1H), 7.01 (t, J = 8.9 Hz, 2H), 6.83 (d, J = 7.9 Hz, 2H), 5.18 (s, 2H), 3.39 (t, J = 6.4 Hz, 2H), 2.75 (t, J = 6.7 Hz, 2H), 1.22 (s, 9H) |
| 40 | 3-chloro-4-(trifluoromethoxy)benzyl | 516.2 | (500 MHz, DMSO-d$_6$) δ 8.43 (d, J = 6.1 Hz, 2H), 7.48 (d, J = 8.5 Hz, 1H), 7.21 (s, 1H), 7.16 (dd, J = 8.9, 5.8 Hz, 2H), 7.12 (br. s., 1H), 7.02 (d, J = 6.1 Hz, 2H), 6.98 (t, J = 8.9 Hz, 2H), 6.89 (d, J = 8.5 Hz, 1H), 5.21 (s, 2H), 2.78 (t, J = 6.7 Hz, 2H) Note: CH$_2$ buried under water |
| 41 | 3-fluoro-5-(trifluoromethyl)benzyl | 484.3 | (500 MHz, DMSO-d$_6$) δ 8.42 (d, J = 6.1 Hz, 2H), 7.56 (d, J = 8.5 Hz, 1H), 7.18-7.11 (m, 3H), 7.05-6.93 (m, 6H), 5.29 (s, 2H), 2.80 (t, J = 6.7 Hz, 2H) Note: CH$_2$ buried under water |
| 42 | 4-(methylsulfonyl)benzyl | 476.3 | (500 MHz, DMSO-d$_6$) δ 8.42 (d, J = 6.1 Hz, 2H), 7.85 (d, J = 8.5 Hz, 2H), 7.21-7.10 (m, 5H), 7.06-6.94 (m, 4H), 5.29 (s, 2H), 3.17 (s, 3H), 2.77-2.73 (m, 2H) Note: CH$_2$ buried under water |
| 43 | 2-fluoro-4-(trifluoromethyl)benzyl | 484.1 | (500 MHz, DMSO-d$_6$) δ 8.41 (d, J = 6.1 Hz, 2H), 7.63 (d, J = 9.8 Hz, 1H), 7.51 (d, J = 7.9 Hz, 1H), 7.19-7.12 (m, 3H), 7.05-6.94 (m, 4H), 6.87 (t, J = 7.3 Hz, 1H), 5.30 (s, 2H), 3.45-3.42 (m, 2H), 2.80 (t, J = 6.7 Hz, 2H) |
| 44 | 4-fluorobenzyl | 416.3 | (500 MHz, DMSO-d$_6$) δ 8.51 (d, J = 4.9 Hz, 2H), 7.21-7.07 (m, 7H), 7.00 (t, J = 8.9 Hz, 2H), 6.93 (dd, J = 8.2, 5.8 Hz, 2H), 5.20 (s, 2H), 3.41 (t, J = 5.8 Hz, 2H), 2.78 (t, J = 6.7 Hz, 2H) |
| 45 | 4-methylbenzyl | 412.3 | (500 MHz, DMSO-d$_6$) δ 8.43 (d, J = 6.1 Hz, 2H), 7.15 (dd, J = 8.9, 5.8 Hz, 2H), 7.10 (d, J = 7.9 Hz, 2H), 7.07 (br. s., 1H), 7.02 (d, J = 6.1 Hz, 2H), 6.97 (t, J = 8.9 Hz, 2H), 6.77 (d, J = 7.9 Hz, 2H), 5.10 (s, 2H), 3.39 (br. s., 2H), 2.76-2.71 (m, 2H), 2.23 (s, 3H) |
| 46 | 3-fluoro-4-methylbenzyl | 430.2 | (500 MHz, DMSO-d$_6$) δ 8.43 (d, J = 5.5 Hz, 2H), 7.15 (dd, J = 8.5, 6.1 Hz, 2H), 7.08 (br. s., 1H), 7.03 (d, J = 6.1 Hz, 3H), 7.00-6.93 (m, 2H), 6.82 (d, J = 6.1 Hz, 1H), 6.67 (br. s., 1H), 5.09 (s, 2H), 2.76 (t, J = 6.7 Hz, 2H), 2.14 (s, 3H) Note: CH$_2$ buried under water |
| 47 | (5-cyclopropyl-1,3,4-thiadiazol-2-yl)methyl | 446.2 | (500 MHz, DMSO-d$_6$, water suppressed) δ 8.60 (d, J = 5.0 Hz, 2H), 7.31 (d, J = 5.7 Hz, 2H), 7.21 (br. s., 1H), 7.18-7.12 (m, 2H), 7.01 (t, J = 8.8 Hz, 2H), 5.59 (s, 2H), 3.46-3.40 (m, 2H), 2.93-2.87 (m, 2H), 2.48-2.42 (m, 1H), 1.20-1.14 (m, 2H), 0.99-0.93 (m, 2H) |

TABLE 2-continued

| Ex. No. | R | M + H | ¹H NMR |
|---|---|---|---|
| 48 | (3-fluoro-4-(5-methyl-1,2,4-oxadiazol-3-yl)phenyl)methyl group | 498.2 | (500 MHz, DMSO-$d_6$, water suppressed) δ 8.41 (d, J = 5.7 Hz, 2H), 7.75 (d, J = 8.1 Hz, 1H), 7.65 (d, J = 10.8 Hz, 1H), 7.19-7.12 (m, 3H), 7.03 (d, J = 5.7 Hz, 2H), 6.98 (t, J = 8.9 Hz, 2H), 6.88 (t, J = 7.7 Hz, 1H), 5.29 (s, 2H), 3.46-3.40 (m, 2H), 2.83 (t, J = 6.7 Hz, 2H), 2.65 (s, 3H) |
| 49 | cyanomethyl group | 347.2 | (500 MHz, DMSO-$d_6$, water suppressed) δ 8.57 (d, J = 5.7 Hz, 2H), 7.21 (br. s., 1H), 7.18-7.10 (m, 4H), 7.00 (t, J = 8.9 Hz, 2H), 5.20 (s, 2H), 3.47 (br. s., 2H), 2.97 (t, J = 6.6 Hz, 2H) |
| 50 | (3,5-dimethylisoxazol-4-yl)methyl group | 417.2 | (500 MHz, DMSO-$d_6$, water suppressed) δ 8.42 (d, J = 4.7 Hz, 2H), 7.13-7.07 (m, 3H), 7.03 (d, J = 5.4 Hz, 2H), 6.96 (t, J = 8.8 Hz, 2H), 5.02 (s, 2H), 3.42 (br. s., 2H), 2.87 (t, J = 6.7 Hz, 2H), 1.86 (s, 3H), 1.78 (s, 3H) |
| 51 | (4-cyano-2-fluorophenyl)methyl group | 441.1 | (500 MHz, DMSO-$d_6$, water suppressed) δ 8.41 (d, J = 5.4 Hz, 2H), 7.78 (d, J = 9.8 Hz, 1H), 7.60 (d, J = 8.1 Hz, 1H), 7.18-7.09 (m, 3H), 7.04-6.93 (m, 4H), 6.82 (t, J = 7.7 Hz, 1H), 5.29 (s, 2H), 3.48-3.39 (m, 2H), 2.79 (t, J = 6.7 Hz, 2H) |
| 52 | (4-cyclopropylphenyl)methyl group | 438.3 | (500 MHz, DMSO-$d_6$ water suppressed) δ 8.43 (d, J = 5.0 Hz, 2H), 7.18-7.12 (m, 2H), 7.07 (br. s., 1H), 7.02 (d, J = 5.0 Hz, 2H), 7.00-6.94 (m, 4H), 6.75 (d, J = 7.7 Hz, 2H), 5.09 (s, 2H), 3.39 (d, J = 11.8 Hz, 2H), 2.75-2.70 (m, 2H), 1.88-1.80 (m, 1H), 0.90 (d, J = 6.7 Hz, 2H), 0.60 (d, J = 4.7 Hz, 2H) |
| 53 | (2,4-bis(trifluoromethyl)phenyl)methyl group | 534.0 | (500 MHz, DMSO-$d_6$, water suppressed) δ 8.38 (d, J = 5.7 Hz, 2H), 8.07 (d, J = 8.1 Hz, 1H), 8.00 (s, 1H), 7.22-7.16 (m, 3H), 7.03-6.96 (m, 4H), 6.89 (d, J = 8.1 Hz, 1H), 5.37 (s, 2H), 3.47-3.35 (m, 2H), 2.76 (t, J = 6.7 Hz, 2H) |
| 54 | (5-cyanopyridin-2-yl)methyl group | 424.1 | (500 MHz, DMSO-$d_6$, water suppressed) δ 8.96 (s, 1H), 8.41 (d, J = 5.7 Hz, 2H), 8.25 (dd, J = 8.2, 1.9 Hz, 1H), 7.19-7.09 (m, 4H), 7.03-6.95 (m, 4H), 5.32 (s, 2H), 3.38 (br. s., 2H), 2.76 (t, J = 6.7 Hz, 2H) |
| 55 | (4-fluoro-2-(trifluoromethyl)phenyl)methyl group | 484.1 | (500 MHz, DMSO-$d_6$, water suppressed) δ 8.39 (d, J = 5.7 Hz, 2H), 7.62 (dd, J = 8.8, 2.4 Hz, 1H), 7.55-7.49 (m, 1H), 7.21-7.14 (m, 3H), 7.03-6.95 (m, 4H), 6.68 (dd, J = 8.4, 5.4 Hz, 1H), 5.25 (s, 2H), 3.46-3.34 (m, 2H), 2.74 (t, J = 6.7 Hz, 2H) |
| 56 | (5-cyclopropyl-1,3,4-oxadiazol-2-yl)methyl group | 430.1 | (500 MHz, DMSO-$d_6$, water suppressed) δ 8.51 (d, J = 5.4 Hz, 2H), 7.17-7.08 (m, 5H), 6.98 (t, J = 8.9 Hz, 2H), 5.33 (s, 2H), 3.47-3.41 (m, 2H), 2.93-2.89 (m, 2H), 2.22-2.14 (m, 1H), 1.14-1.07 (m, 2H), 0.92-0.85 (m, 2H) |
| 57 | n-butyl group | 364.2 | (500 MHz, DMSO-$d_6$ water suppressed) δ 8.52 (d, J = 5.7 Hz, 2H), 7.16 (d, J = 5.7 Hz, 2H), 7.10 (dd, J = 8.2, 5.9 Hz, 2H), 7.04 (br. s., 1H), 6.96 (t, J = 8.9 Hz, 2H), 3.85 (t, J = 7.6 Hz, 2H), 3.43 (br. s., 2H), 2.93-2.86 (m, 2H), 1.40 (quin, J = 7.5 Hz, 2H), 1.09 (sxt, J = 7.3 Hz, 2H), 0.71 (t, J = 7.4 Hz, 3H) |
| 58 | isobutyl group | 364.1 | (500 MHz, DMSO-$d_6$, water suppressed) δ 8.50 (d, J = 5.4 Hz, 2H), 7.16 (d, J = 5.7 Hz, 2H), 7.11 (dd, J = 8.2, 5.9 Hz, 2H), 7.06 (br. s., 1H), 6.96 (t, J = 8.8 Hz, 2H), 3.77 (d, J = 7.4 Hz, 2H), 3.42 (br. s., 2H), 2.89 (t, J = 6.7 Hz, 2H), 1.50 (dt, J = 13.5, 6.7 Hz, 1H), 0.61 (d, J = 6.7 Hz, 6H) |

TABLE 2-continued

| Ex. No. | R | M + H | ¹H NMR |
|---|---|---|---|
| 59 | (butyronitrile chain, CN) | 375.3 | (500 MHz, DMSO-d$_6$, water suppressed) δ 8.52 (d, J = 5.7 Hz, 2H), 7.19 (d, J = 5.4 Hz, 2H), 7.13-7.05 (m, 3H), 6.96 (t, J = 8.9 Hz, 2H), 3.94 (t, J = 7.6 Hz, 2H), 3.44 (br. s., 2H), 3.48-3.41 (m, 1H), 2.92 (t, J = 6.6 Hz, 2H), 2.40 (t, J = 7.1 Hz, 2H), 1.73 (quin, J = 7.2 Hz, 2H) |
| 60 | (2-methylthiazol-4-ylmethyl) | 419.2 | (500 MHz, DMSO-d$_6$, water suppressed) δ 8.60 (d, J = 5.7 Hz, 2H), 7.43 (d, J = 5.7 Hz, 2H), 7.18-7.12 (m, 3H), 7.04-6.99 (m, 2H), 5.17 (s, 2H), 3.42 (t, J = 5.7 Hz, 2H), 2.91-2.87 (m, 2H), 2.61 (s, 3H) |
| 61 | (neopentyl) | 378.3 | (500 MHz, DMSO-d$_6$, water suppressed) δ 8.49 (br. s., 2H), 7.15 (br. s., 2H), 7.12-7.07 (m, 3H), 6.99-6.93 (m, 2H), 3.94 (br. s., 2H), 3.36 (br. s., 2H), 2.94 (d, J = 6.7 Hz, 2H), 0.61 (s, 9H) |
| 62 | (sec-butyl) | 336.1 | (500 MHz, DMSO-d$_6$ water suppressed) δ 8.57 (d, J = 5.4 Hz, 2H), 7.26 (d, J = 5.0 Hz, 2H), 7.14-7.08 (m, 3H), 6.99-6.95 (m, 2H), 3.90 (d, J = 7.1 Hz, 2H), 3.44 (br. s., 2H), 2.92 (t, J = 6.7 Hz, 2H), 1.11 (t, J = 7.2 Hz, 3H) |
| 63 | (2-methylbutyl) | 364.1 | (500 MHz, DMSO-d$_6$, water suppressed) δ 8.54 (br. s., 2H), 7.16 (d, J = 4.4 Hz, 2H), 7.11-7.04 (m, 3H), 6.93 (t, J = 8.8 Hz, 2H), 3.94 (d, J = 7.4 Hz, 1H), 3.41 (br. s., 2H), 2.99 (q, J = 7.0 Hz, 2H), 1.79 (d, J = 8.1 Hz, 1H), 1.68 (dd, J = 14.0, 6.9 Hz, 1H), 1.44 (d, J = 7.1 Hz, 3H), 0.62 (t, J = 7.2 Hz, 3H) |
| 64 | (2,4-difluorobenzyl) | 434.2 | (500 MHz, DMSO-d$_6$, water suppressed) δ 8.42 (d, J = 5.4 Hz, 2H), 7.20-7.08 (m, 4H), 7.20-7.08 (m, 4H), 7.02 (d, J = 6.1 Hz, 2H), 7.00-6.93 (m, 3H), 6.74-6.66 (m, 1H), 5.17 (s, 2H), 3.48-3.38 (m, 2H), 2.81 (t, J = 6.6 Hz, 2H) |
| 65 | (1,3-dimethylpyrazol-5-ylmethyl) | 416.2 | (500 MHz, DMSO-d$_6$, water suppressed) δ 8.46 (d, J = 4.7 Hz, 2H), 7.17-7.08 (m, 3H), 7.03-6.94 (m, 4H), 5.50 (s, 1H), 5.13 (s, 2H), 3.50 (s, 3H), 3.45-3.35 (m, 2H), 2.78 (t, J = 6.6 Hz, 2H), 2.02 (s, 3H) |
| 66 | (pyridin-4-ylmethyl) | 399.2 | (500 MHz, DMSO-d$_6$, water suppressed) δ 8.47 (d, J = 5.0 Hz, 2H), 8.41 (d, J = 5.4 Hz, 2H), 7.17 (dd, J = 8.2, 5.9 Hz, 2H), 7.12 (br. s., 1H), 7.04-6.95 (m, 4H), 6.89 (d, J = 5.4 Hz, 2H), 5.21 (s, 2H), 3.46-3.35 (m, 2H), 2.77-2.72 (m, 2H) |
| 67 | (2-methoxy-4-trifluoromethylbenzyl) | 496.2 | (500 MHz, DMSO-d$_6$, water suppressed) δ 8.55 (br. s., 2H), 7.28-7.17 (m, 8H), 7.02 (t, J = 8.8 Hz, 2H), 6.71 (d, J = 7.7 Hz, 1H), 5.19 (s, 2H), 3.82 (s, 3H), 3.40 (t, J = 5.9 Hz, 2H), 2.78-2.73 (m, 2H) |
| 68 | (2-cyanobenzyl) | 423.3 | (500 MHz, DMSO-d$_6$ water suppressed) δ 8.37 (d, J = 5.7 Hz, 2H), 7.74 (d, J = 7.7 Hz, 1H), 7.62 (t, J = 7.7 Hz, 1H), 7.42 (t, J = 7.6 Hz, 1H), 7.18-7.09 (m, 3H), 7.01-6.94 (m, 4H), 6.78 (d, J = 7.7 Hz, 1H), 5.36 (s, 2H), 3.43 (br. s., 2H), 2.81 (t, J = 6.7 Hz, 2H) |
| 69 | (4-hydroxybutyl) | 366.2 | (500 MHz, DMSO-d$_6$, water suppressed) δ 8.51 (d, J = 4.4 Hz, 2H), 7.16 (d, J = 4.7 Hz, 2H), 7.12-7.07 (m, 2H), 7.04 (br. s., 1H), 6.96 (t, J = 8.8 Hz, 2H), 3.93 (t, J = 7.1 Hz, 2H), 3.43 (br. s., 2H), 3.25 (br. s., 2H), 2.90 (t, J = 6.4 Hz, 2H), 1.59-1.51 (m, 2H) |

TABLE 2-continued

| Ex. No. | R | M + H | ¹H NMR |
|---|---|---|---|
| 70 | 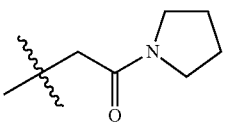 [SMILES: *CC(=O)N1CCCC1] | 419.2 | (500 MHz, DMSO-$d_6$, water suppressed) δ 8.49 (d, J = 5.4 Hz, 2H), 7.11 (dd, J = 8.4, 5.7 Hz, 2H), 7.05 (br. s., 1H), 7.03-6.94 (m, 4H), 4.66 (s, 2H), 3.47-3.34 (m, 4H), 3.29 (t, J = 6.6 Hz, 2H), 2.75 (t, J = 6.7 Hz, 2H), 1.88-1.81 (m, 2H), 1.75 (quin, J = 6.6 Hz, 2H) |
| 71 | 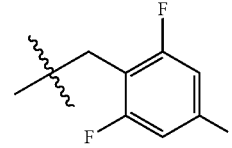 | 452.2 | (500 MHz, DMSO-$d_6$, water suppressed) δ 8.42 (d, J = 5.0 Hz, 2H), 7.12-6.99 (m, 7H), 6.93 (t, J = 8.8 Hz, 2H), 5.22 (s, 2H), 3.43 (br. s., 2H), 2.86 (t, J = 6.7 Hz, 2H) |
| 72 | 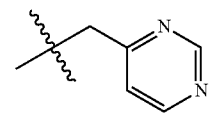 | 400.1 | (500 MHz, DMSO-$d_6$, water suppressed) δ 9.10 (s, 1H), 8.87 (d, J = 5.0 Hz, 1H), 8.68 (d, J = 6.4 Hz, 2H), 7.65 (d, J = 4.7 Hz, 1H), 7.56 (d, J = 6.1 Hz, 2H), 7.39-7.32 (m, 2H), 7.29-7.21 (m, 4H), 5.79 (s, 2H), 3.44 (d, J = 13.1 Hz, 2H), 3.00-2.93 (m, 2H) |
| 73 | 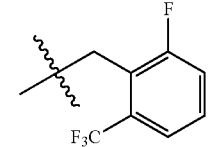 | 484.1 | (500 MHz, DMSO-$d_6$ water suppressed) δ 8.35 (d, J = 5.0 Hz, 2H), 7.51 (d, J = 2.4 Hz, 2H), 7.45-7.37 (m, 1H), 7.11-7.05 (m, 3H), 7.00 (d, J = 5.4 Hz, 2H), 6.93 (t, J = 8.9 Hz, 2H), 5.38 (s, 2H), 3.36 (br. s., 2H), 2.67 (t, J = 6.6 Hz, 2H) |
| 74 | 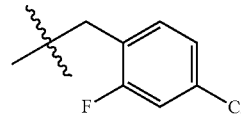 | 450.2 | (500 MHz, DMSO-$d_6$, water suppressed) δ 8.42 (d, J = 5.4 Hz, 2H), 7.39-7.34 (m, 1H), 7.20 (d, J = 8.4 Hz, 1H), 7.17-7.10 (m, 3H), 7.02 (d, J = 5.4 Hz, 2H), 6.97 (t, J = 8.8 Hz, 2H), 6.67 (t, J = 8.2 Hz, 1H), 5.19 (s, 2H), 3.41 (d, J = 8.4 Hz, 2H), 2.80 (t, J = 6.7 Hz, 2H) |
| 75 | 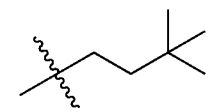 [SMILES: *CCC(C)(C)C] | 392.2 | (500 MHz, DMSO-$d_6$, water suppressed) δ 8.53 (d, J = 3.7 Hz, 2H), 7.19 (d, J = 4.4 Hz, 2H), 7.15-7.08 (m, 2H), 7.04 (br. s., 1H), 7.00-6.92 (m, 2H), 3.82 (br. s., 2H), 3.44 (br. s., 2H), 2.93-2.84 (m, 2H), 1.35 (br. s., 2H), 0.75 (br. s., 9H) |
| 76 | 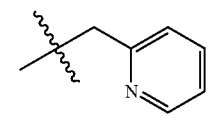 [SMILES: *Cc1ccccn1] | 399.2 | (500 MHz, DMSO-$d_6$, water suppressed) δ 8.50 (d, J = 4.4 Hz, 1H), 8.42 (d, J = 5.7 Hz, 2H), 7.74 (t, J = 7.1 Hz, 1H), 7.30-7.25 (m, 1H), 7.14 (dd, J = 8.4, 5.7 Hz, 2H), 7.07 (br. s., 1H), 7.04 (d, J = 5.7 Hz, 2H), 6.97 (t, J = 8.9 Hz, 2H), 6.92 (d, J = 7.7 Hz, 1H), 5.20 (s, 2H), 3.16 (s, 2H), 2.76 (t, J = 6.7 Hz, 2H) |
| 77 | 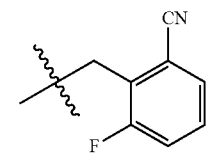 [SMILES: *Cc1c(F)cccc1C#N] | 441.2 | (500 MHz, DMSO-$d_6$, water suppressed) δ 8.32 (d, J = 5.0 Hz, 2H), 7.51 (d, J = 7.4 Hz, 1H), 7.46-7.33 (m, 2H), 7.11-7.04 (m, 3H), 6.98 (d, J = 5.7 Hz, 2H), 6.93 (t, J = 8.9 Hz, 2H), 5.45 (s, 2H), 3.49-3.37 (m, 2H), 2.88 (t, J = 6.7 Hz, 2H) |
| 78 | 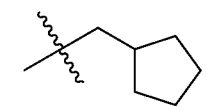 [SMILES: *CC1CCCC1] | 390.3 | (500 MHz, DMSO-$d_6$, water suppressed) δ 8.51 (br. s., 2H), 7.16 (d, J = 3.7 Hz, 2H), 7.11 (dd, J = 8.2, 5.9 Hz, 2H), 7.05 (br. s., 1H), 6.95 (t, J = 8.8 Hz, 2H), 3.87 (d, J = 7.4 Hz, 2H), 3.46-3.36 (m, 2H), 2.94-2.89 (m, 2H), 1.83 (dt, J = 14.2, 7.2 Hz, 1H), 1.41-1.32 (m, 6H), 0.97-0.87 (m, 2H) |
| 79 | 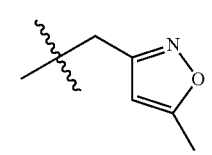 [SMILES: *Cc1cc(C)on1] | 403.2 | (500 MHz, DMSO-$d_6$, water suppressed) δ 8.49 (d, J = 5.4 Hz, 2H), 7.10 (dd, J = 15.1, 5.7 Hz, 5H), 6.98 (t, J = 8.8 Hz, 2H), 5.97 (s, 1H), 5.13 (s, 2H), 3.41 (d, J = 12.8 Hz, 2H), 2.84 (t, J = 6.6 Hz, 2H), 2.35 (s, 3H) |

TABLE 2-continued

| Ex. No. | R | M + H | ¹H NMR |
|---|---|---|---|
| 80 | 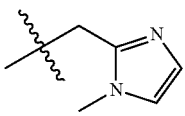 [SMILES: *Cc1nccn1C] | 402.2 | (500 MHz, DMSO-$d_6$, water suppressed) δ 8.49 (d, J = 6.7 Hz, 2H), 7.52 (d, J = 6.4 Hz, 2H), 7.35-7.29 (m, 2H), 7.24-7.19 (m, 3H), 7.12 (br. s., 1H), 6.86 (s, 1H), 5.61 (s, 2H), 3.68 (s, 3H), 3.39 (br. s., 2H), 2.91 (br. s., 2H) |
| 81 | 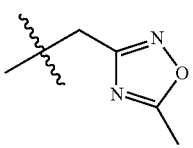 [SMILES: *Cc1noc(C)n1] | 404.2 | (500 MHz, DMSO-$d_6$, water suppressed) δ 8.49 (d, J = 5.0 Hz, 2H), 7.16-7.08 (m, 5H), 6.98 (t, J = 8.8 Hz, 2H), 5.22 (s, 2H), 3.41 (d, J = 14.8 Hz, 2H), 2.88 (t, J = 6.6 Hz, 2H), 2.57 (s, 3H) |
| 82 | 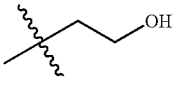 | 352.1 | (500 MHz, DMSO-$d_6$, water suppressed) δ 8.49 (d, J = 5.0 Hz, 2H), 7.16-7.08 (m, 5H), 6.98 (t, J = 8.8 Hz, 2H), 5.22 (s, 2H), 3.41 (d, J = 14.8 Hz, 2H), 2.88 (t, J = 6.6 Hz, 2H), 2.57 (s, 3H) |
| 83 | 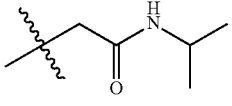 [SMILES: *CC(=O)NC(C)C] | 407.3 | (500 MHz, DMSO-$d_6$, water suppressed) δ 8.48 (d, J = 5.4 Hz, 2H), 8.03 (d, J = 7.7 Hz, 1H), 7.14-7.08 (m, 2H), 7.04 (d, J = 6.1 Hz, 3H), 6.97 (t, J = 8.9 Hz, 2H), 4.41 (s, 2H), 3.81 (dq, J = 13.4, 6.6 Hz, 1H), 3.41 (m, 2H), 2.78 (t, J = 6.7 Hz, 2H), 1.01 (d, J = 6.4Hz, 6H) |
| 84 | 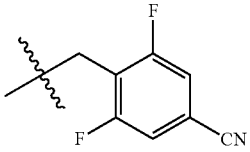 [SMILES: *Cc1c(F)cc(C#N)cc1F] | 459.1 | (500 MHz, DMSO-$d_6$, water suppressed) δ 8.42 (d, J = 5.0 Hz, 2H), 7.63 (d, J = 7.4 Hz, 2H), 7.13-7.06 (m, 3H), 7.04 (d, J = 5.4 Hz, 2H), 6.94 (t, J = 8.8 Hz, 2H), 5.34 (s, 2H), 3.43 (br. s., 2H), 2.86 (t, J = 6.6 Hz, 2H) |

The following compounds in Table 3 were made in a similar manner as Example 3:

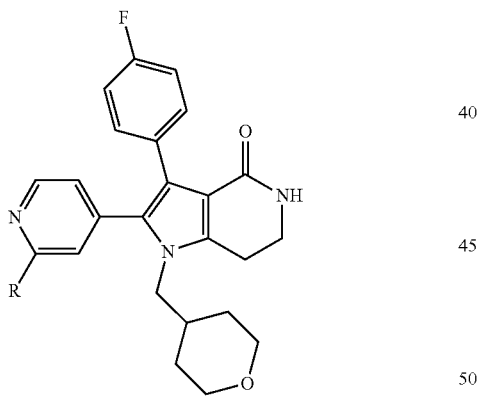

TABLE 3

| Ex. No. | R | M + H | ¹H NMR: (500 MHz, DMSO-$d_6$) |
|---|---|---|---|
| 85 | 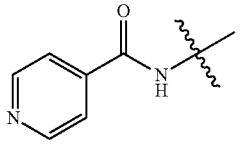 [SMILES: *NC(=O)c1ccncc1] | 526.4 | δ 8.76 (d, J = 5.7 Hz, 2H), 8.31 (d, J = 4.7 Hz, 1H), 7.89 (d, J = 5.7 Hz, 2H), 7.15 (dd, J = 8.2, 5.9 Hz, 2H), 7.06 (br. s., 1H), 6.97 (t, J = 8.8 Hz, 2H), 6.86 (d, J = 4.7 Hz, 1H), 3.95-3.87 (m, 2H), 3.69 (d, J = 8.8 Hz, 2H), 3.43 (br. s., 1H), 3.16 (d, J = 3.7 Hz, 1H), 3.09 (t, J = 11.3 Hz, 2H), 2.93 (t, J = 6.6 Hz, 2H), 1.63 (br. s., 1H), 1.23 (d, J = 11.4 Hz, 2H), 1.07-0.93 (m, 2H) |

TABLE 3-continued

| Ex. No. | R | M + H | ¹H NMR: (500 MHz, DMSO-d$_6$) |
|---|---|---|---|
| 86 | benzamide | 525.3 | δ 8.29 (d, J = 4.7 Hz, 1H), 8.01 (d, J = 7.7 Hz, 2H), 7.63-7.57 (m, 1H), 7.54-7.48 (m, 2H), 7.20-7.13 (m, 2H), 7.07 (br. s., 1H), 6.97 (t, J = 8.8 Hz, 2H), 6.81 (d, J = 4.7 Hz, 1H), 3.96-3.88 (m, 2H), 3.70 (d, J = 9.8 Hz, 2H), 3.09 (t, J = 11.3 Hz, 2H), 2.93 (t, J = 6.4 Hz, 2H), 2.89 (s, 1H), 2.73 (s, 1H), 1.64 (br. s., 1H), 1.23 (d, J = 11.4 Hz, 2H), 1.07-0.94 (m, 2H) |
| 87 | cyclopropanecarboxamide | 489.4 | δ 8.20 (d, J = 5.0 Hz, 1H), 7.14-7.08 (m, 2H), 7.03 (br. s., 1H), 6.94 (t, J = 8.8 Hz, 2H), 6.73 (d, J = 4.4 Hz, 1H), 3.81 (d, J = 7.1 Hz, 2H), 3.68 (d, J = 8.8 Hz, 2H), 3.43 (br. s., 1H), 3.06 (t, J = 11.3 Hz, 2H), 2.93-2.86 (m, 2H), 1.96 (br. s., 1H), 1.60 (br. s., 1H), 1.19 (d, J = 12.1 Hz, 2H), 1.02-0.90 (m, 2H), 0.78 (br. s., 4H) |
| 88 | isobutyramide | 491.3 | δ 8.20 (d, J = 4.7 Hz, 1H), 7.13 (t, J = 6.6 Hz, 2H), 7.05 (br. s., 1H), 6.95 (t, J = 8.4 Hz, 2H), 6.73 (d, J = 4.7 Hz, 1H), 3.84 (d, J = 7.1 Hz, 2H), 3.69 (d, J = 8.8 Hz, 2H), 3.43 (br. s., 1H), 3.08 (t, J = 11.3 Hz, 2H), 2.96-2.85 (m, 2H), 2.76-2.69 (m, 2H), 1.62 (br. s., 1H), 1.21 (d, J = 12.8 Hz, 2H), 1.06 (d, J = 6.7 Hz, 6H), 0.98 (d, J = 9.8 Hz, 2H) |
| 89 | 4-methoxybenzamide | 555.4 | δ 8.28 (d, J = 4.7 Hz, 1H), 8.06 (s, 1H), 8.02 (d, J = 8.8 Hz, 2H), 7.21-7.13 (m, 2H), 7.04 (d, J = 8.8 Hz, 2H), 6.97 (t, J = 8.8 Hz, 2H), 6.80 (d, J = 4.4 Hz, 1H), 3.95-3.88 (m, 2H), 3.84 (s, 3H), 3.70 (d, J = 10.1 Hz, 2H), 3.46 (br. s., 1H), 3.10 (t, J = 11.3 Hz, 2H), 2.96-2.91 (m, 3H), 1.64 (br. s., 1H), 1.24 (d, J = 12.1 Hz, 2H), 1.00 (d, J = 9.1 Hz, 2H) |
| 90 | propionamide | 477.4 | δ 8.19 (d, J = 5.0 Hz, 1H), 7.15-7.09 (m, 2H), 7.02 (br. s., 1H), 6.95 (t, J = 8.9 Hz, 2H), 6.74 (d, J = 4.7 Hz, 1H), 3.83 (d, J = 7.1 Hz, 2H), 3.68 (d, J = 10.1 Hz, 2H), 3.42 (br. s., 2H), 3.07 (t, J = 11.3 Hz, 2H), 2.93-2.90 (m, 2H), 2.36 (q, J = 7.5 Hz, 2H), 1.60 (br. s., 1H), 1.20 (d, J = 12.8 Hz, 2H), 1.03 (t, J = 7.6 Hz, 3H), 0.97 (d, J = 12.1 Hz, 2H) |
| 91 | isopropyl carbamate | 507.3 | δ 8.15 (d, J = 5.0 Hz, 1H), 7.16-7.09 (m, 2H), 7.04 (br. s., 1H), 6.95 (t, J = 8.8 Hz, 2H), 6.71 (d, J = 4.4 Hz, 1H), 4.86 (dt, J = 12.5, 6.2 Hz, 1H), 3.84 (d, J = 7.4 Hz, 2H), 3.69 (d, J = 9.4 Hz, 2H), 3.41 (d, J = 6.7 Hz, 2H), 3.07 (t, J = 11.1 Hz, 2H), 2.91 (br. s., 1H), 1.60 (br. s., 1H), 1.26-1.14 (m, 8H), 0.98 (d, J = 8.8 Hz, 2H) |
| 92 | methanesulfonamide | 499.2 | δ 8.12 (d, J = 5.0 Hz, 1H), 7.13 (m, 2H), 7.07 (br. s., 1H), 6.98 (t, J = 8.8 Hz, 2H), 6.81 (d, J = 4.4 Hz, 1H), 3.84 (d, J = 7.4 Hz, 2H), 3.70 (d, J = 9.4 Hz, 2H), 3.39 (d, J = 6.7 Hz, 1H), 3.09 (t, J = 11.1 Hz, 3H), 2.89 (s, 4H), 1.93 (br. s., 1H), 1.58 (br. s., 1H), 1.20 (d, J = 10.8 Hz, 2H), 1.00 (d, J = 8.8 Hz, 2H) |
| 93 | isovaleramide | 505.3 | δ 8.20 (d, J = 5.0 Hz, 1H), 7.12 (dd, J = 8.2, 5.9 Hz, 2H), 7.05 (br. s., 1H), 6.95 (t, J = 8.9 Hz, 2H), 6.76 (d, J = 4.7 Hz, 1H), 3.85 (d, J = 7.1 Hz, 1H), 3.68 (d, J = 8.8 Hz, 1H), 3.43 (br. s., 1H), 3.07 (t, J = 11.1 Hz, 2H), 2.96-2.86 (m, 3H), 2.24 (d, J = 7.1 Hz, 2H), 2.03 (dt, J = 13.7, 6.8 Hz, 1H), 1.61 (br. s., 1H), 1.21 (d, J = 12.8 Hz, 2H), 1.04-0.94 (m, 2H), 0.89 (d, J = 6.7 Hz, 6H) |
| 94 | butyramide | 491.3 | δ 8.21 (d, J = 5.0 Hz, 1H), 7.17-7.10 (m, 2H), 7.06 (br. s., 1H), 6.96 (t, J = 8.8 Hz, 2H), 6.75 (d, J = 4.7 Hz, 1H), 3.85 (d, J = 7.4 Hz, 1H), 3.70 (d, J = 9.4 Hz, 1H), 3.43 (br. s., 1H), 3.08 (t, J = 11.4 Hz, 1H), 2.96-2.87 (m, 2H), 2.51 (br. s., 3H), 2.35 (t, J = 7.2 Hz, 2H), 1.58 (quin, J = 7.4 Hz, 3H), 1.21 (d, J = 12.5 Hz, 2H), 1.05-0.93 (m, 2H), 0.88 (t, J = 7.4 Hz, 3H) |

TABLE 3-continued

| Ex. No. | R | M + H | ¹H NMR: (500 MHz, DMSO-d₆) |
|---|---|---|---|
| 95 | ethyl carbamate | 493.2 | δ 8.17 (br. s., 1H), 7.16-7.10 (m, 2H), 7.06 (br. s., 1H), 6.96 (t, J = 8.8 Hz, 2H), 6.72 (d, J = 4.4 Hz, 1H), 4.11 (q, J = 7.1 Hz, 2H), 3.84 (d, J = 7.4 Hz, 2H), 3.69 (d, J = 8.8 Hz, 2H), 3.42 (br. s., 1H), 3.08 (t, J = 11.3 Hz, 2H), 2.91 (t, J = 6.6 Hz, 2H), 1.60 (br. s., 1H), 1.21 (t, J = 7.1 Hz, 5H), 1.04-0.92 (m, 2H) |
| 96 | methyl urea | 477.4 | δ 8.09 (d, J = 4.7 Hz, 1H), 7.14 (br. s., 2H), 7.12 (br. s., 1H), 6.97 (t, J = 8.8 Hz, 2H), 6.67 (br. s., 1H), 3.84 (d, J = 7.1 Hz, 2H), 3.69 (d, J = 8.8 Hz, 2H), 3.42 (t, J = 6.2 Hz, 2H), 3.08 (t, J = 11.1 Hz, 2H), 2.91 (t, J = 6.6 Hz, 2H), 2.71 (d, J = 3.0 Hz, 3H), 1.59 (br. s., 1H), 1.19 (d, J = 12.1 Hz, 2H), 1.06-0.92 (m, 2H) |
| 97 | ethyl urea | 492.3 | δ 8.08 (d, J = 4.7 Hz, 1H), 7.17 (br. s., 1H), 7.13 (dd, J = 8.2, 5.9 Hz, 2H), 6.97 (t, J = 8.8 Hz, 2H), 6.66 (d, J = 4.7 Hz, 1H), 3.84 (d, J = 7.1 Hz, 2H), 3.70 (d, J = 8.8 Hz, 2H), 3.23-3.14 (m, 2H), 3.09 (t, J = 11.1 Hz, 2H), 2.91 (t, J = 6.7 Hz, 2H), 1.60 (br. s., 1H), 1.20 (d, J = 12.5 Hz, 2H), 1.08 (t, J = 7.1 Hz, 3H), 1.04-0.93 (m, 2H) |
| 98 | isopropyl urea | 506.3 | δ 8.07 (br. s., 1H), 7.18 (br. s., 1H), 7.13 (br. s., 2H), 7.01-6.92 (m, 2H), 6.65 (br. s., 1H), 3.84 (d, J = 6.4 Hz, 3H), 3.70 (d, J = 9.8 Hz, 2H), 3.42 (br. s., 2H), 3.09 (t, J = 11.1 Hz, 2H), 2.91 (br. s., 2H), 1.60 (br. s., 1H), 1.20 (d, J = 12.1 Hz, 2H), 1.12 (d, J = 5.7 Hz, 6H), 0.99 (d, J = 10.4 Hz, 2H) |

The following compounds in Table 4 were made in a similar manner as Example 4:

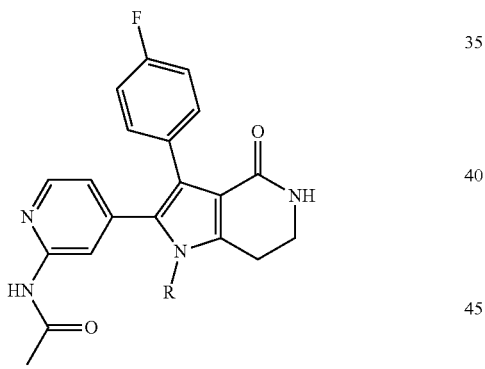

TABLE 4

| Ex. No. | R | M + H | ¹H NMR |
|---|---|---|---|
| 99 | 4-fluoro-3-cyanobenzyl | 498.2 | (500 MHz, DMSO-d₆) δ 8.12 (d, J = 5.0 Hz, 1H), 7.44-7.33 (m, 2H), 7.20 (br. s., 1H), 7.16-7.11 (m, 2H), 7.03 (br. s., 1H), 6.95 (t, J = 8.8 Hz, 2H), 6.67 (d, J = 4.7 Hz, 1H), 5.12 (br. s., 2H), 3.42 (br. s., 2H), 2.79 (t, J = 6.6 Hz, 2H), 2.00 (s, 3H) |
| 100 | 2-cyano-4-fluorobenzyl | 498.4 | (400 MHz, CD₃OD) δ 8.08 (d, J = 5.7 Hz, 1H), 7.52 (dd, J = 8.3, 2.8 Hz, 1H), 7.48 (s, 1H), 7.38 (td, J = 8.5, 2.8 Hz, 1H), 7.27-7.20 (m, 2H), 6.98-6.91 (m, 3H), 6.86 (dd, J = 5.7, 1.5 Hz, 1H), 5.47 (s, 2H), 3.62 (t, J = 6.9 Hz, 2H), 2.95 (t, J = 6.9 Hz, 2H), 2.17 (s, 3H) |

TABLE 4-continued

| Ex. No. | R | M + H | ¹H NMR |
|---|---|---|---|
| 101 | 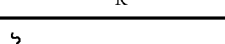 | 541.4 | (400 MHz, CD$_3$OD) δ 8.09 (d, J = 5.5 Hz, 1H), 7.57 (s, 1H), 7.46-7.37 (m, 2H), 7.23 (dd, J = 8.5, 5.4 Hz, 2H), 6.92 (t, J = 8.8 Hz, 3H), 6.84 (d, J = 4.6 Hz, 1H), 5.39 (s, 2H), 3.59 (t, J = 6.9 Hz, 2H), 2.92 (t, J = 6.8 Hz, 2H), 2.14 (s, 3H) |
| 102 |  | 523.2 | (500 MHz, DMSO-d$_6$) δ 8.12 (d, J = 5.0 Hz, 1H), 7.65 (d, J = 8.1 Hz, 2H), 7.21-7.15 (m, 2H), 7.13-7.06 (m, 3H), 6.98 (t, J = 8.9 Hz, 2H), 6.66 (d, J = 4.4 Hz, 1H), 5.26 (s, 2H), 3.44-3.29 (m, 2H), 2.73 (t, J = 6.6 Hz, 2H), 2.00 (s, 3H) |

The following compounds in Table 5 were made in a similar manner as Example 5:

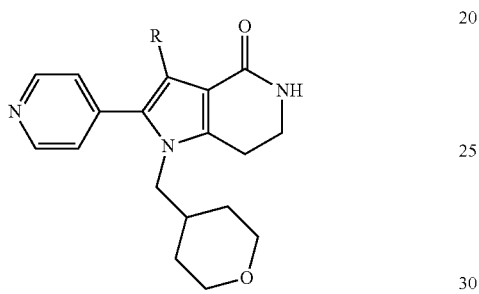

TABLE 5

| Ex. No. | R | M + H | ¹H NMR: (500 MHz, DMSO-d$_6$) |
|---|---|---|---|
| 103 | 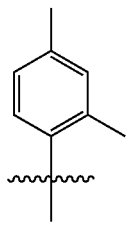 [SMILES: *c1ccc(C)cc1C] | 416.4 | δ 8.42 (d, J = 3.7 Hz, 2H), 7.05 (d, J = 6.1 Hz, 2H), 6.94 (br. s., 1H), 6.89 (s, 1H), 6.77-6.72 (m, 1H), 6.71-6.68 (m, 1H), 3.96-3.84 (m, 2H), 3.68 (t, J = 10.4 Hz, 2H), 3.05 (td, J = 10.7, 6.1 Hz, 2H), 2.92 (d, J = 3.1 Hz, 2H), 2.20 (s, 3H), 1.98 (s, 3H), 1.53 (d, J = 3.7 Hz, 1H), 1.14 (d, J = 9.8 Hz, 2H), 1.01-0.83 (m, 2H) |
| 104 | 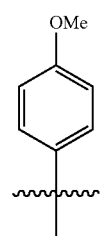 [SMILES: *c1ccc(OC)cc1] | 418.3 | δ 8.50 (d, J = 4.9 Hz, 2H), 7.16 (d, J = 5.5 Hz, 2H), 7.04-6.97 (m, 3H), 6.69 (d, J = 8.5 Hz, 2H), 3.87-3.79 (m, 2H), 3.71-3.64 (m, 5H), 3.04 (t, J = 11.3 Hz, 2H), 2.93-2.88 (m, 2H), 1.56-1.45 (m, 1H), 1.17 (d, J = 12.2 Hz, 2H), 0.99-0.87 (m, 2H) |
| 105 | 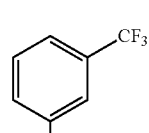 | 456.4 | δ 8.53 (d, J = 5.5 Hz, 2H), 7.45 (d, J = 5.5 Hz, 1H), 7.42 (s, 1H), 7.38-7.32 (m, 2H), 7.21 (d, J = 6.1 Hz, 2H), 7.11 (br. s., 1H), 3.84 (d, J = 7.3 Hz, 2H), 3.68 (dd, J = 11.3, 2.7 Hz, 2H), 3.05 (t, J = 11.0 Hz, 2H), 2.93 (t, J = 7.0 Hz, 2H), 1.60-1.48 (m, 1H), 1.19 (d, J = 12.2 Hz, 2H), 1.01-0.87 (m, 2H) |

TABLE 5-continued

| Ex. No. | R | M + H | ¹H NMR: (500 MHz, DMSO-d$_6$) |
|---|---|---|---|
| 106 | 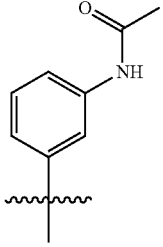 [SMILES: *c1cccc(NC(C)=O)c1] | 445.4 | δ 9.77 (s, 1H), 8.48 (d, J = 4.3 Hz, 2H), 7.40 (d, J = 7.9 Hz, 1H), 7.35 (s, 1H), 7.15 (d, J = 5.5 Hz, 2H), 7.04-6.95 (m, 2H), 6.65 (d, J = 7.3 Hz, 1H), 3.84 (d, J = 6.7 Hz, 2H), 3.68 (d, J = 8.5 Hz, 2H), 3.04 (t, J = 11.6 Hz, 2H), 2.93-2.89 (m, 2H), 1.97 (s, 3H), 1.51 (br. s., 1H), 1.17 (d, J = 12.2 Hz, 2H), 1.00-0.87 (m, 2H) |
| 107 | 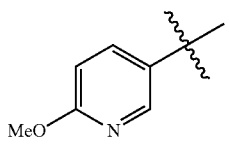 | 419.4 | δ 8.55 (br. s., 2H), 7.78 (d, J = 1.8 Hz, 1H), 7.47 (dd, J = 8.5, 2.4 Hz, 1H), 7.22 (br. s., 2H), 7.09 (br. s., 1H), 6.63 (d, J = 8.5 Hz, 1H), 3.84 (d, J = 7.3 Hz, 2H), 3.76 (s, 3H), 3.67 (d, J = 8.5 Hz, 2H), 3.05 (t, J = 11.0 Hz, 2H), 2.91 (t, J = 6.7 Hz, 2H), 1.51 (d, J = 4.3 Hz, 1H), 1.18 (d, J = 11.6 Hz, 2H), 0.93 (qd, J = 12.2, 4.3 Hz, 2H) |
| 108 | 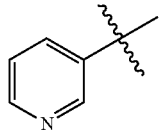 | 389.3 | δ 8.54 (d, J = 4.9 Hz, 2H), 8.28 (d, J = 3.7 Hz, 1H), 8.21 (s, 1H), 7.53 (d, J = 7.9 Hz, 1H), 7.24-7.15 (m, 3H), 7.12 (br. s., 1H), 3.85 (d, J = 7.3 Hz, 2H), 3.68 (d, J = 8.5 Hz, 2H), 3.05 (t, J = 11.3 Hz, 2H), 2.93 (t, J = 6.7 Hz, 2H), 1.53 (br. s., 1H), 1.19 (d, J = 12.2 Hz, 2H), 1.00-0.88 (m, 2H) |
| 109 | 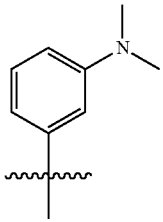 [SMILES: *c1cccc(N(C)C)c1] | 431.4 | δ 8.66 (br. s., 2H), 7.49 (br. s., 2H), 7.10 (br. s., 1H), 7.07-7.01 (m, 2H), 6.74 (s, 1H), 6.56 (d, J = 7.3 Hz, 1H), 3.91 (d, J = 7.3 Hz, 2H), 3.67 (d, J = 11.0 Hz, 2H), 3.43 (t, J = 6.1 Hz, 2H), 3.06 (t, J = 11.3 Hz, 2H), 2.94 (t, J = 6.7 Hz, 2H), 2.80 (s, 6H), 1.53 (br. s., 1H), 1.60-1.48 (m, 1H), 1.17 (d, J = 11.0 Hz, 2H), 1.01-0.89 (m, 2H) |
| 110 | 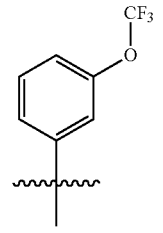 [SMILES: *c1cccc(OC(F)(F)F)c1] | 472.2 | δ 8.53 (d, J = 5.5 Hz, 2H), 7.29-7.22 (m, 1H), 7.21-7.14 (m, 3H), 7.12-7.05 (m, 2H), 6.98 (s, 1H), 3.83 (d, J = 7.3 Hz, 2H), 3.67 (d, J = 7.9 Hz, 2H), 3.05 (t, J = 11.3 Hz, 2H), 2.92 (t, J = 6.7 Hz, 2H), 1.52 (br. s., 1H), 1.19 (d, J = 11.6 Hz, 2H), 1.00-0.87 (m, 2H) |
| 111 | 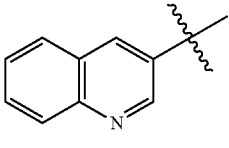 [SMILES: *c1cnc2ccccc2c1] | 439.3 | δ 8.58 (s, 1H), 8.52 (d, J = 4.9 Hz, 2H), 8.01 (s, 1H), 7.94 (s, 1H), 7.91 (d, J = 7.9 Hz, 1H), 7.76 (d, J = 7.9 Hz, 1H), 7.67 (t, J = 7.3 Hz, 1H), 7.52 (t, J = 7.3 Hz, 1H), 7.27 (d, J = 4.3 Hz, 2H), 7.16 (br. s., 1H), 3.93-3.88 (m, 2H), 3.69 (d, J = 9.8 Hz, 2H), 3.07 (t, J = 11.6 Hz, 2H), 2.97 (t, J = 6.4 Hz, 2H), 1.57 (br. s., 1H), 1.22 (d, J = 12.2 Hz, 2H), 1.03-0.90 (m, 2H) |
| 112 | 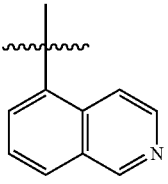 [SMILES: *c1cccc2cnccc12] | 439.2 | δ 9.22 (s, 1H), 9.25-9.20 (m, 1H), 8.34 (d, J = 6.1 Hz, 2H), 7.99-7.92 (m, 2H), 7.52-7.46 (m, 1H), 7.41 (dd, J = 9.8, 6.7 Hz, 2H), 7.04 (d, J = 6.1 Hz, 2H), 6.96 (br. s., 1H), 3.95 (dd, J = 11.0, 7.9 Hz, 2H), 3.70 (t, J = 9.2 Hz, 2H), 3.08 (t, J = 11.6 Hz, 2H), 3.04-2.97 (m, 2H), 1.60 (br. s., 1H), 1.23 (br. s., 2H), 1.07-0.89 (m, 2H) |

The following compounds in Table 6 were made in a similar manner as Example 9 and/or Example 14:

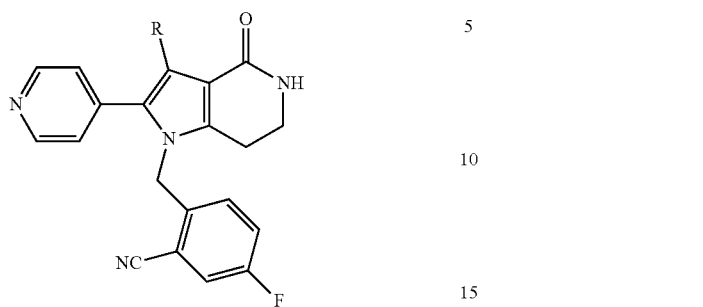

TABLE 6

| Ex. No. | R | M + H | $^1$H NMR: (500 MHz, DMSO-d$_6$) |
|---|---|---|---|
| 113 | OMe, OMe (phenyl) | 483.2 | δ 8.40 (d, J = 4.9 Hz, 2H), 7.78 (d, J = 7.9 Hz, 1H), 7.49 (t, J = 8.2 Hz, 1H), 7.10 (br. s., 1H), 7.01 (d, J = 4.9 Hz, 2H), 6.84-6.78 (m, 1H), 6.77 (s, 1H), 6.71 (d, J = 7.9 Hz, 1H), 6.63 (d, J = 7.9 Hz, 1H), 5.32 (br. s., 2H), 3.67 (s, 3H), 3.50 (s, 3H), 2.81 (br. s., 2H) Note: CH$_2$ under water peak |
| 114 | CF$_3$O (phenyl) | 507.2 | δ 8.41 (d, J = 5.5 Hz, 2H), 7.77 (d, J = 5.5 Hz, 1H), 7.48 (t, J = 8.9 Hz, 1H), 7.32-7.24 (m, 1H), 7.20 (d, J = 9.2 Hz, 2H), 7.10 (d, J = 7.9 Hz, 1H), 7.04-6.97 (m, 3H), 6.87-6.81 (m, 1H), 5.34 (s, 2H), 2.83 (t, J = 6.7 Hz, 2H) Note: CH$_2$ under water peak |
| 115 | F, F (phenyl) | 459.1 | (water suppressed) δ 8.43 (d, J = 4.7 Hz, 2H), 7.79 (d, J = 6.7 Hz, 1H), 7.53-7.45 (m, 1H), 7.27-7.14 (m, 3H), 7.04 (d, J = 5.0 Hz, 2H), 6.87-6.80 (m, 2H), 5.35 (s, 2H), 3.48-3.43 (m, 2H), 2.87-2.80 (m, 2H) |
| 116 | quinolinyl | 474.2 | δ 8.83-8.77 (m, 1H), 8.36 (d, J = 5.5 Hz, 2H), 8.13 (d, J = 7.9 Hz, 1H), 7.82-7.75 (m, 2H), 7.68 (s, 1H), 7.55-7.48 (m, 2H), 7.43 (dd, J = 8.5, 4.3 Hz, 1H), 7.19 (br. s., 1H), 7.03 (d, J = 6.1 Hz, 2H), 6.86 (dd, J = 8.5, 5.5 Hz, 1H), 5.40 (s, 2H), 3.51-3.45 (m, 2H), 2.88-2.84 (m, 2H) |
| 117 | MeO, F (phenyl) | 471.2 | (water suppressed) δ 8.42 (d, J = 5.0 Hz, 2H), 7.77 (d, J = 5.7 Hz, 1H), 7.52-7.44 (m, 1H), 7.16 (br. s., 1H), 7.03 (d, J = 5.7 Hz, 2H), 6.82 (dd, J = 8.4, 5.4 Hz, 1H), 6.56 (dd, J = 18.7, 10.6 Hz, 2H), 6.48 (s, 1H), 5.32 (s, 2H), 3.57 (s, 3H), 3.44 (br. s., 2H), 2.82 (t, J = 6.6 Hz, 2H) |

TABLE 6-continued

| Ex. No. | R | M + H | ¹H NMR: (500 MHz, DMSO-d₆) |
|---|---|---|---|
| 118 | 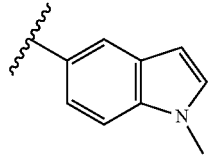 [SMILES: *c1ccc2c(ccn2C)c1] | 476.2 | δ 8.42 (d, J = 5.0 Hz, 2H), 7.77 (d, J = 5.7 Hz, 1H), 7.52-7.44 (m, 1H), 7.16 (br. s., 1H), 7.03 (d, J = 5.7 Hz, 2H), 6.82 (dd, J = 8.4, 5.4 Hz, 1H), 6.56 (dd, J = 18.7, 10.6 Hz, 2H), 6.48 (s, 1H), 5.32 (s, 2H), 3.57 (s, 3H), 3.44 (br. s., 2H), 2.82 (t, J = 6.6 Hz, 2H) Note: CH₂ under water peak |
| 119 | 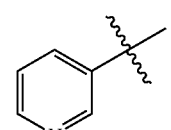 | 424.2 | δ 8.41 (d, J = 5.5 Hz, 2H), 8.30 (d, J = 4.9 Hz, 1H), 8.26 (d, J = 1.8 Hz, 1H), 7.78 (dd, J = 8.5, 2.4 Hz, 1H), 7.56 (d, J = 7.9 Hz, 1H), 7.52-7.45 (m, 1H), 7.23-7.17 (m, 2H), 7.03 (d, J = 5.5 Hz, 2H), 6.84 (dd, J = 8.5, 5.5 Hz, 1H), 5.36 (s, 2H), 3.49-3.43 (m, 2H), 2.84 (t, J = 6.7 Hz, 2H) |
| 120 | 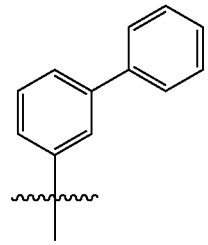 [SMILES: *c1cccc(-c2ccccc2)c1] | 499.2 | δ 8.42 (d, J = 4.9 Hz, 2H), 7.79 (d, J = 6.7 Hz, 1H), 7.53-7.47 (m, 1H), 7.45 (s, 1H), 7.43-7.37 (m, 5H), 7.32 (d, J = 6.1 Hz, 1H), 7.22 (t, J = 7.9 Hz, 1H), 7.17 (br. s., 1H), 7.10 (d, J = 7.9 Hz, 1H), 7.06 (d, J = 5.5 Hz, 2H), 6.84 (dd, J = 9.2, 4.9 Hz, 1H), 5.36 (s, 2H), 3.46 (br. s., 2H), 2.84 (t, J = 6.4 Hz, 2H) |
| 121 | 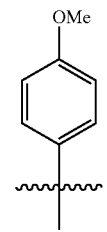 [SMILES: *c1ccc(OC)cc1] | 453.3 | (water suppressed) δ 8.38 (d, J = 4.7 Hz, 2H), 7.77 (d, J = 7.4 Hz, 1H), 7.49 (t, J = 7.9 Hz, 1H), 7.08 (br. s., 1H), 7.04 (d, J = 8.1 Hz, 2H), 6.98 (d, J = 4.7 Hz, 2H), 6.79 (dd, J = 8.2, 5.2 Hz, 1H), 6.71 (d, J = 8.1 Hz, 2H), 5.33 (s, 2H), 3.68 (s, 3H), 3.41 (d, J = 8.1 Hz, 2H), 2.81 (t, J = 6.4 Hz, 2H) |
| 122 | 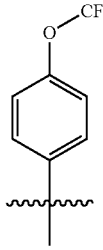 | 507.2 | (water suppressed) δ 8.49 (d, J = 5.4 Hz, 2H), 7.77 (d, J = 8.1 Hz, 1H), 7.51-7.43 (m, 1H), 7.28-7.12 (m, 7H), 6.85 (dd, J = 8.6, 5.2 Hz, 1H), 5.39 (s, 2H), 3.44 (br. s., 2H), 2.82 (t, J = 6.7 Hz, 2H) |
| 123 | 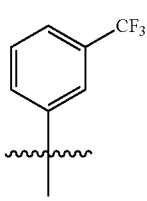 [SMILES: *c1cccc(C(F)(F)F)c1] | 491.2 | (water suppressed) δ 8.50 (d, J = 5.0 Hz, 2H), 7.79 (d, J = 6.7 Hz, 1H), 7.82-7.75 (m, 4H), 7.49 (br. s., 1H), 7.39 (br. s., 2H), 7.22 (d, J = 4.7 Hz, 2H), 6.92-6.85 (m, 1H), 5.40 (s, 2H), 3.45 (d, J = 5.4 Hz, 2H), 2.83 (t, J = 6.4 Hz, 2H) |
| 124 | 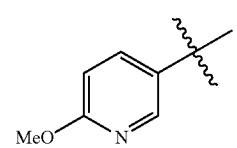 | 454.2 | δ 8.40 (d, J = 5.0 Hz, 2H), 7.80 (s, 1H), 7.75 (d, J = 8.4 Hz, 1H), 7.52-7.44 (m, 2H), 7.13 (br. s., 1H), 7.03 (d, J = 5.4 Hz, 2H), 6.82 (dd, J = 8.6, 5.2 Hz, 1H), 6.64 (d, J = 8.4 Hz, 1H), 5.33 (s, 2H), 3.76 (s, 3H), 3.44 (br. s., 2H), 2.83 (t, J = 6.6 Hz, 2H) |
| 125 | 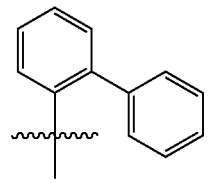 [SMILES: *c1ccccc1-c1ccccc1] | 499.2 | (water suppressed) d 8.16 (d, J = 5.7 Hz, 2H), 7.86 (dd, J = 8.4, 2.4 Hz, 1H), 7.59 (t, J = 8.4 Hz, 1H), 7.42-7.38 (m, 1H), 7.34-7.28 (m, 2H), 7.20-7.12 (m, 5H), 6.80-6.75 (m, 2H), 6.46 (dd, J = 8.6, 4.9 Hz, 1H), 6.25 (d, J = 5.7 Hz, 2H), 5.34 (d, J = 17.8 Hz, 1H), 5.02 (d, J = 17.8 Hz, 1H), 3.51-3.29 (m, 2H), 2.90-2.81 (m, 1H), 2.66-2.55 (m, 1H), 1.91 (s, 3H) Note: Acetate salt |

TABLE 6-continued

| Ex. No. | R | M + H | $^1$H NMR: (500 MHz, DMSO-$d_6$) |
|---|---|---|---|
| 126 | 3-(methylsulfonyl)phenyl | 501.1 | (water suppressed) δ 8.54 (br. s., 2H), 7.81 (dd, J = 8.2, 2.5 Hz, 1H), 7.74-7.67 (m, 2H), 7.53-7.42 (m, 3H), 7.27 (d, J = 5.4 Hz, 2H), 6.88 (dd, J = 8.6, 5.2 Hz, 1H), 5.43 (s, 2H), 3.46 (br. s., 2H), 3.04 (s, 3H), 2.85 (t, J = 6.6 Hz, 2H) |
| 127 | 3-hydroxyphenyl | 439.1 | (water suppressed) δ 8.38 (br. s., 2H), 7.78 (dd, J = 8.4, 2.7 Hz, 1H), 7.50 (td, J = 8.7, 2.5 Hz, 1H), 7.11 (br. s., 1H), 6.98 (d, J = 4.0 Hz, 2H), 6.90 (t, J = 7.9 Hz, 1H), 6.78 (dd, J = 8.6, 5.2 Hz, 1H), 6.61 (s, 1H), 6.50 (dd, J = 18.5, 7.7 Hz, 2H), 5.33 (s, 2H), 3.43 (br. s., 2H), 2.85-2.77 (m, 2H) |
| 128 | thiophen-3-yl | 429.1 | (water suppressed) δ 8.58 (d, J = 4.7 Hz, 2H), 7.77 (dd, J = 8.4, 2.7 Hz, 1H), 7.47 (td, J = 8.6, 2.7 Hz, 1H), 7.38 (d, J = 6.1 Hz, 2H), 7.33 (dd, J = 4.9, 2.9 Hz, 1H), 7.22 (d, J = 2.0 Hz, 1H), 6.92 (d, J = 4.7 Hz, 1H), 6.83 (dd, J = 8.8, 5.0 Hz, 1H), 5.39 (s, 2H), 3.42 (t, J = 6.6 Hz, 2H), 2.81 (t, J = 6.7 Hz, 2H) |
| 129 | 2,3-dichlorophenyl | 491.1 | (water suppressed) δ 8.43 (br. s., 2H), 7.86-7.81 (m, 1H), 7.49 (d, J = 7.7 Hz, 1H), 7.24-7.10 (m, 4H), 7.03 (d, J = 4.7 Hz, 2H), 6.80 (dd, J = 8.6, 5.2 Hz, 1H), 5.43 (br. s., 2H), 3.42 (br. s., 2H), 2.90-2.76 (m, 2H) |
| 130 | 5-chlorothiophen-2-yl | 463.1 | (water suppressed) δ 8.49 (d, J = 5.4 Hz, 2H), 7.76 (dd, J = 8.4, 2.7 Hz, 1H), 7.47 (td, J = 8.6, 2.4 Hz, 1H), 7.26 (br. s., 1H), 7.13 (d, J = 5.7 Hz, 2H), 6.85-6.79 (m, 3H), 5.28 (s, 2H), 3.46-3.38 (m, 2H), 2.81 (t, J = 6.7 Hz, 2H) |
| 131 | 4-methoxy-3-methylpyridin-yl | 454.3 | (water suppressed) δ 8.68 (d, J = 6.7 Hz, 1H), 8.62 (s, 1H), 8.49 (d, J = 5.4 Hz, 2H), 7.82 (dd, J = 8.4, 2.4 Hz, 1H), 7.49 (d, J = 6.7 Hz, 2H), 7.29 (br. s., 1H), 7.18 (d, J = 5.4 Hz, 2H), 6.86 (dd, J = 8.8, 5.0 Hz, 1H), 5.45 (s, 2H), 3.69 (s, 3H), 3.49-3.40 (m, 2H), 2.85 (br. s., 2H) |
| 132 | isoquinolin-4-yl | 474.2 | (water suppressed) δ 9.17 (s, 1H), 8.23 (d, J = 4.7 Hz, 2H), 8.13 (s, 1H), 8.09 (d, J = 8.1 Hz, 1H), 7.79-7.72 (m, 2H), 7.68 (t, J = 7.4 Hz, 1H), 7.65-7.60 (m, 1H), 7.50 (td, J = 8.6, 2.4 Hz, 1H), 7.03 (br. s., 1H), 6.99 (dd, J = 8.8, 5.4 Hz, 1H), 6.90 (d, J = 5.4 Hz, 2H), 5.46 (s, 2H), 5.49-5.43 (m, 2H), 3.57-3.42 (m, 2H), 2.98-2.84 (m, 2H) |
| 133 | 3-sulfamoylphenyl | 502.1 | (water suppressed) δ 8.38 (d, J = 5.0 Hz, 2H), 7.76 (dd, J = 8.4, 2.7 Hz, 1H), 7.63 (s, 1H), 7.58 (d, J = 7.4 Hz, 1H), 7.48 (td, J = 8.5, 2.5 Hz, 1H), 7.35-7.29 (m, 1H), 7.29-7.24 (m, 3H), 7.16 (br. s., 1H), 7.00 (d, J = 5.4 Hz, 2H), 6.82 (dd, J = 8.6, 5.2 Hz, 1H), 5.35 (s, 2H), 3.47 (br. s., 2H), 2.85 (t, J = 6.7 Hz, 2H) |

TABLE 6-continued

| Ex. No. | R | M + H | ¹H NMR: (500 MHz, DMSO-d$_6$) |
|---|---|---|---|
| 134 | 3-hydroxymethylphenyl | 453.2 | (water suppressed) δ 8.36 (d, J = 5.0 Hz, 2H), 7.77 (dd, J = 8.4, 2.7 Hz, 1H), 7.49 (td, J = 8.5, 2.5 Hz, 1H), 7.53-7.45 (m, 1H), 7.12 (s, 1H), 7.07 (d, J = 4.7 Hz, 3H), 6.97 (d, J = 5.4 Hz, 2H), 6.92 (br. s., 1H), 6.79 (dd, J = 8.6, 5.2 Hz, 1H), 5.33 (s, 2H), 4.35 (d, J = 5.4 Hz, 2H), 3.44 (br. s., 2H), 2.82 (t, J = 6.6 Hz, 2H) |
| 135 | 4-(benzyloxy)phenyl | 529.2 | (water suppressed) δ 8.55 (br. s., 2H), 7.81 (dd, J = 8.4, 2.4 Hz, 1H), 7.54-7.46 (m, 1H), 7.45-7.41 (m, 2H), 7.38 (t, J = 7.4 Hz, 2H), 7.35-7.25 (m, 4H), 7.08 (d, J = 8.4 Hz, 2H), 6.84 (d, J = 8.8 Hz, 3H), 5.42 (s, 2H), 5.03 (s, 2H), 3.42 (t, J = 6.2 Hz, 2H), 2.81 (t, J = 6.7 Hz, 2H) |
| 136 | 3,4-dichlorophenyl | 491.1 | (water suppressed) δ 8.43 (d, J = 5.4 Hz, 2H), 7.78 (dd, J = 8.4, 2.4 Hz, 1H), 7.47 (td, J = 8.5, 2.5 Hz, 1H), 7.42 (d, J = 1.7 Hz, 1H), 7.40-7.35 (m, 1H), 7.21 (br. s., 1H), 7.04 (d, J = 5.7 Hz, 2H), 7.00 (dd, J = 8.2, 1.9 Hz, 1H), 6.83 (dd, J = 8.8, 5.4 Hz, 1H), 5.34 (s, 2H), 3.43 (d, J = 8.1 Hz, 2H), 2.82 (t, J = 6.6 Hz, 2H) |
| 137 | 2-hydroxyphenyl | 439.2 | (water suppressed) δ 8.34 (d, J = 4.7 Hz, 2H), 7.78 (dd, J = 8.4, 2.4 Hz, 1H), 7.54-7.47 (m, 2H), 7.01 (t, J = 7.6 Hz, 1H), 6.95 (d, J = 5.4 Hz, 2H), 6.83-6.73 (m, 3H), 6.56 (t, J = 7.2 Hz, 1H), 5.39 (s, 2H), 3.43 (br. s., 2H), 2.83 (t, J = 6.6 Hz, 2H) |
| 138 | 3,5-dichlorophenyl | 491.1 | (water suppressed) δ 8.42 (d, J = 5.0 Hz, 2H), 7.75-7.68 (m, 1H), 7.47-7.41 (m, 1H), 7.33 (s, 1H), 7.15 (br. s., 1H), 7.09 (s, 2H), 7.04 (d, J = 5.0 Hz, 2H), 6.83 (dd, J = 8.4, 5.4 Hz, 1H), 5.31 (s, 2H), 3.45 (br. s., 2H), 2.82 (t, J = 6.7 Hz, 2H) |
| 139 | 3-cyanophenyl | 448.2 | (water suppressed) δ 8.41 (d, J = 4.7 Hz, 2H), 7.77 (dd, J = 8.2, 2.2 Hz, 1H), 7.63-7.56 (m, 2H), 7.51-7.44 (m, 1H), 7.40-7.30 (m, 2H), 7.20 (br. s., 1H), 7.02 (d, J = 5.0 Hz, 2H), 6.84 (dd, J = 8.6, 5.2 Hz, 1H), 5.34 (s, 2H), 3.45 (br. s., 2H), 2.84 (t, J = 6.6 Hz, 2H) |
| 140 | 2-methoxypyridin-3-yl | 454.2 | (water suppressed) δ 8.42 (d, J = 5.0 Hz, 2H), 7.82 (d, J = 2.0 Hz, 1H), 7.78 (dd, J = 8.6, 2.5 Hz, 1H), 7.53-7.45 (m, 2H), 7.18 (br. s., 1H), 7.03 (d, J = 5.7 Hz, 2H), 6.82 (dd, J = 8.6, 5.2 Hz, 1H), 6.64 (d, J = 8.8 Hz, 1H), 5.35 (s, 2H), 3.77 (s, 3H), 3.45 (br. s., 2H), 2.83 (t, J = 6.7 Hz, 2H) |

TABLE 6-continued

| Ex. No. | R | M + H | ¹H NMR: (500 MHz, DMSO-d₆) |
|---|---|---|---|
| 141 | 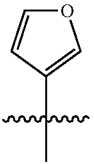 [SMILES: *c1ccoc1] | 413.2 | (water suppressed) δ 8.46 (br. s., 2H), 7.75 (dd, J = 8.4, 2.4 Hz, 1H), 7.45 (td, J = 8.6, 2.4 Hz, 1H), 7.27 (s, 1H), 7.21 (br. s., 1H), 7.10 (d, J = 4.0 Hz, 2H), 6.93 (d, J = 3.4 Hz, 1H), 6.76 (dd, J = 8.6, 5.2 Hz, 1H), 6.35 (br. s., 1H), 5.27 (s, 2H), 3.47-3.39 (m, 2H), 2.81 (t, J = 6.6 Hz, 2H) |
| 142 | 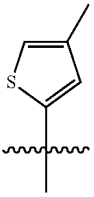 [SMILES: *c1cc(C)cs1] | 443.2 | (water suppressed) δ 8.45 (d, J = 5.0 Hz, 2H), 7.75 (dd, J = 8.4, 2.4 Hz, 1H), 7.47 (td, J = 8.4, 2.4 Hz, 1H), 7.15 (br. s., 1H), 7.09 (d, J = 5.7 Hz, 2H), 6.97 (s, 1H), 6.84-6.76 (m, 2H), 5.27 (s, 2H), 3.48-3.38 (m, 2H), 2.81 (t, J = 6.7 Hz, 2H), 2.07 (s, 3H) |
| 143 | 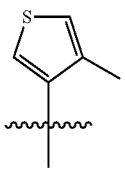 [SMILES: *c1cscc1C] | 443.2 | (water suppressed) δ 8.31 (d, J = 4.4 Hz, 2H), 7.71 (dd, J = 8.4, 2.4 Hz, 1H), 7.49-7.42 (m, 1H), 6.98 (br. s., 2H), 6.93 (d, J = 5.4 Hz, 2H), 6.85 (d, J = 3.0 Hz, 1H), 6.79 (dd, J = 8.6, 5.2 Hz, 1H), 5.35 (br. s., 2H), 3.43 (br. s., 2H), 2.81 (t, J = 6.7 Hz, 2H), 1.94 (s, 3H) |
| 144 | 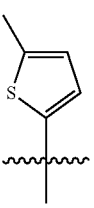 [SMILES: *c1ccc(C)s1] | 443.2 | (water suppressed) δ 8.44 (d, J = 4.4 Hz, 2H), 7.74 (dd, J = 8.4, 2.4 Hz, 1H), 7.47 (td, J = 8.7, 2.5 Hz, 1H), 7.14 (br. s., 1H), 7.08 (d, J = 5.4 Hz, 2H), 6.83 (d, J = 3.4 Hz, 1H), 6.79 (dd, J = 8.6, 5.2 Hz, 1H), 6.52 (d, J = 2.4 Hz, 1H), 5.26 (s, 2H), 3.53-3.37 (m, 2H), 2.80 (t, J = 6.7 Hz, 2H), 2.28 (s, 3H) |
| 145 | 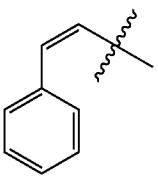 [SMILES: */C=C\c1ccccc1] | 449.2 | (water suppressed) δ 8.56 (d, J = 4.0 Hz, 2H), 7.73 (dd, J = 8.4, 2.4 Hz, 1H), 7.44 (td, J = 8.6, 2.4 Hz, 1H), 7.29-7.11 (m, 10H), 6.75 (dd, J = 8.8, 5.4 Hz, 1H), 5.28 (s, 2H), 3.47-3.40 (m, 2H), 2.80 (t, J = 6.7 Hz, 2H) |

The following compounds in Table 7 were made in a similar manner as Example 10 and/or Example 3:

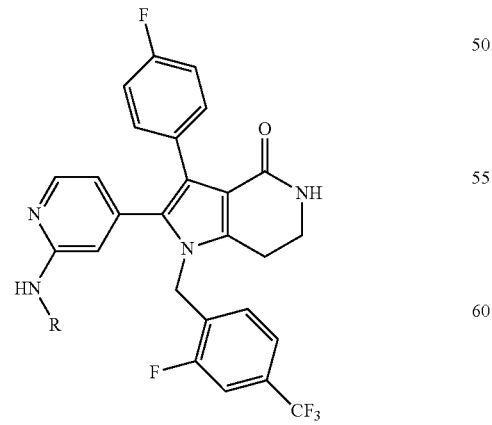

TABLE 7

| Ex. No. | R | M + H | $^1$H NMR: (500 MHz, DMSO-$d_6$) |
|---|---|---|---|
| 146 | 2-hydroxyethyl | 543.4 | δ 7.78 (d, J = 5.4 Hz, 1H), 7.65 (d, J = 10.1 Hz, 1H), 7.54 (d, J = 8.1 Hz, 1H), 7.20 (dd, J = 7.9, 5.9 Hz, 2H), 7.07 (br. s., 1H), 6.99 (t, J = 8.8 Hz, 2H), 6.85 (t, J = 7.6 Hz, 1H), 6.42 (t, J = 5.0 Hz, 1H), 6.14 (s, 1H), 6.08 (d, J = 5.0 Hz, 1H), 5.24 (s, 2H), 3.46 (d, J = 8.1 Hz, 1H), 3.40 (d, J = 5.7 Hz, 2H), 3.21-3.03 (m, 2H), 2.72 (s, 2H), 2.50 (br. m., 2H) |
| 147 | 2-methoxyethyl | 557.5 | δ 7.79 (d, J = 5.0 Hz, 1H), 7.64 (d, J = 10.1 Hz, 1H), 7.53 (d, J = 8.1 Hz, 1H), 7.19 (dd, J = 8.2, 5.9 Hz, 2H), 7.07 (br. s., 1H), 6.98 (t, J = 8.9 Hz, 2H), 6.85 (t, J = 7.6 Hz, 1H), 6.46 (t, J = 5.4 Hz, 1H), 6.15-6.08 (m, 2H), 5.24 (s, 2H), 3.48 (d, J = 7.7 Hz, 1H), 3.40 (br. s., 1H), 3.34-3.27 (m, 2H), 3.26-3.13 (m, 5H), 2.77-2.70 (m, 2H) |
| 148 | ethyl | 527.5 | δ 7.79 (br. s., 1H), 7.64 (d, J = 10.1 Hz, 1H), 7.53 (d, J = 7.7 Hz, 1H), 7.19 (t, J = 6.7 Hz, 2H), 7.05 (br. s., 1H), 6.98 (t, J = 8.8 Hz, 2H), 6.85 (t, J = 7.4 Hz, 1H), 6.36 (br. s., 1H), 6.11 (d, J = 4.4 Hz, 1H), 6.00 (br. s., 1H), 5.23 (br. s., 2H), 3.40 (br. s., 2H), 3.05-2.95 (m, 2H), 2.74 (t, J = 6.6 Hz, 2H), 0.96 (t, J = 6.9 Hz, 3H) |
| 149 | ![structure] | 555.3 | δ 10.35 (s, 1H), 8.11 (d, J = 5.0 Hz, 1H), 7.74 (s, 1H), 7.58 (d, J = 10.1 Hz, 1H), 7.51 (d, J = 8.1 Hz, 1H), 7.17 (dd, J = 8.2, 5.9 Hz, 2H), 7.12 (br. s., 1H), 6.98 (t, J = 8.9 Hz, 2H), 6.89 (t, J = 7.6 Hz, 1H), 6.65 (d, J = 4.4 Hz, 1H), 5.26 (s, 2H), 3.58-3.48 (m, 2H), 2.83 (t, J = 6.6 Hz, 2H), 2.29 (q, J = 7.4 Hz, 2H), 0.97 (t, J = 7.6 Hz, 3H) |
| 150 | ![structure] | 571.3 | δ 9.95 (s, 1H), 8.14 (d, J = 5.0 Hz, 1H), 7.73 (s, 1H), 7.60 (d, J = 10.1 Hz, 1H), 7.51 (d, J = 8.1 Hz, 1H), 7.21-7.10 (m, 3H), 6.98 (t, J = 8.8 Hz, 2H), 6.89 (t, J = 7.6 Hz, 1H), 6.70 (d, J = 4.7 Hz, 1H), 5.29 (s, 2H), 3.96 (s, 2H), 3.46-3.34 (m, 2H), 3.30 (s, 3H), 2.85-2.77 (m, 2H) |
| 151 | cyclopropyl | 539.3 | δ 7.83 (d, J = 4.7 Hz, 1H), 7.68 (d, J = 9.8 Hz, 1H), 7.57 (d, J = 8.1 Hz, 1H), 7.26-7.15 (m, 2H), 7.10 (br. s., 1H), 7.00 (t, J = 8.8 Hz, 2H), 6.91 (t, J = 8.1 Hz, 1H), 6.71 (s, 1H), 6.20 (d, J = 4.7 Hz, 1H), 6.15 (s, 1H), 5.28 (s, 2H), 3.49-3.29 (m, 2H), 2.76 (t, J = 6.6 Hz, 2H), 2.05 (m., 1H), 0.38 (m, 2H), 0.14 (m., 2H) |

Example 152

3-(4-Fluorophenyl)-7,7-dimethyl-2-(pyridin-4-yl)-1-((tetrahydro-2H-pyran-4-yl)methyl)-6,7-dihydro-1H-pyrrolo[3,2-c]pyridin-4(5H)-one

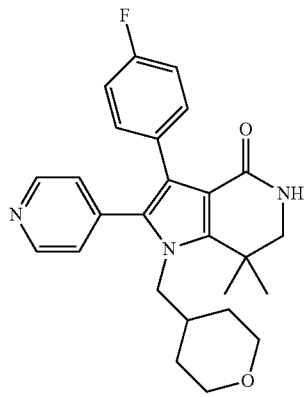 [SMILES: CC1(C)CNC(=O)c2c(-c3ccc(F)cc3)c(-c3ccncc3)n(CC3CCOCC3)c21]

152A: Ethyl 3-amino-2,2-dimethylpropanoate: Raney nickel (1.214 g, 14.17 mmol) was rinsed with MeOH (2 mL) and added to 2-cyano-2-methylpropionic acid ethyl ester (2.066 mL, 14.17 mmol) in ethanol (50 mL). The reaction mixture was put on a Parr shaker under 50 psi $H_2$ for 24 h. The reaction mixture was filtered and concentrated to yield a crude product. The crude product was dissolved in $CH_2Cl_2$ (90 mL) and washed with water (15 mL), brine (15 mL) and dried over $Na_2SO_4$. The mixture was filtered and concentrated in vacuo to yield 152A (1.65 g, 80% yield). $^1$H NMR (400 MHz, CDCl$_3$) δ 4.16 (q, J=7.1 Hz, 2H), 2.76 (s, 2H), 1.28 (t, J=7.1 Hz, 3H), 1.18 (s, 6H).

152B: Ethyl 3-(3-methoxy-3-oxopropanamido)-2,2-dimethylpropanoate: To a solution of 152A (1.346 g, 9.27 mmol) in $CH_2Cl_2$ (20 mL) at 0° C. was added Et$_3$N (1.292 mL, 9.27 mmol), followed by monomethyl malonate (0.873 mL, 8.34 mmol) and EDC (1.777 g, 9.27 mmol). The reaction mixture was stirred at 0° C. for 30 minutes, then warmed to rt and stirred for 16 h. The reaction mixture was diluted with $CH_2Cl_2$ (100 mL) and washed with water (20 mL), saturated $NaHCO_3$ solution (20 mL) and brine (20 mL). The organics were dried over $Na_2SO_4$, filtered and concentrated in vacuo to yield 152B (1.88 g, 83% yield). $^1$H NMR (400 MHz, CDCl$_3$) δ 4.18 (q, J=7.2 Hz, 2H), 3.75 (s, 3H), 3.43 (d, J=6.2 Hz, 2H), 3.33 (s, 2H), 1.29 (t, J=7.0 Hz, 3H), 1.21 (s, 6H).

152C: Methyl 5,5-dimethyl-2,4-dioxopiperidine-3-carboxylate: To a solution of 152B (1.88 g, 7.66 mmol) in toluene (40 mL) was added sodium methoxide (25% wt in MeOH, 1.840 mL, 8.05 mmol) dropwise. The reaction mixture was heated to 100° C. for 2 h. The reaction mixture was concentrated to yield a crude product to which water (20 mL) was added. The aqueous layer was acidified with 1 N HCl (0.671 mL, 8.05 mmol) until pH ~3-4 and saturated with NaCl. The mixture was extracted with $CH_2Cl_2$ (3×20 mL). The combined organic phases were dried over $Na_2SO_4$, filtered and concentrated in vacuo. The crude product was purified by column chromatography on the Isco system (10% MeOH/$CH_2Cl_2$) to yield 152C (0.92 g, 60% yield). $^1$H NMR (400 MHz, CDCl$_3$) δ 14.40 (s, 1H), 3.92 (s, 3H), 3.13 (d, J=3.3 Hz, 2H), 1.27 (s, 6H). MS(ESI) m/z 200.1 (M+H).

152D: 5,5-Dimethylpiperidine-2,4-dione: A solution of 152C (184 mg, 0.924 mmol) in acetonitrile (4 mL) and water (0.200 mL) was heated to 85° C. for 2 h. The reaction mixture was concentrated to yield 152D (124 mg, 95%). $^1$H NMR (400 MHz, CDCl$_3$) δ 3.34 (s, 2H), 3.30 (d, J=3.5 Hz, 2H), 1.22 (s, 6H).

152E: 3-(4-Fluorophenyl)-7,7-dimethyl-6,7-dihydro-1H-pyrrolo[3,2-c]pyridin-4(5H)-one: A solution of 152D (124 mg, 0.878 mmol), 2-amino-1-(4-fluorophenyl) ethanone hydrochloride (167 mg, 0.878 mmol) and KOAc (172 mg, 1.757 mmol) in water (5 mL) was stirred to give a clear solution. Within 5 min a white precipitate formed which was heated to 90° C. for 2 h. The reaction mixture was cooled down to rt. The solid was collected by filtration to give 152E (183 mg, 75% yield). $^1$H NMR (400 MHz, CD$_3$OD) δ 7.59 (dd, J=8.8, 5.5 Hz, 2H), 6.98 (t, J=8.9 Hz, 2H), 6.76 (s, 1H), 3.27 (s, 2H), 1.33 (s, 6H). MS(ESI) m/z 259.1 (M+H).

152F: 2-Bromo-3-(4-fluorophenyl)-7,7-dimethyl-6,7-dihydro-1H-pyrrolo[3,2-c]pyridin-4(5H)-one: To a suspension solution of 152E (183 mg, 0.709 mmol) in DMF (3 mL) at 23° C. was added NBS (126 mg, 0.709 mmol). The reaction mixture became homogeneous and was stirred for 20 min. The reaction mixture was concentrated and triturated in 2 mL of MeOH. The solid was collected as the desired product, and the filtrate was concentrated and purified by column chromatography on the Isco system to yield the second batch of product. The batches of product were combined to provide 152F (160 mg, 67% yield). $^1$H NMR (400 MHz, CD$_3$OD) δ 7.41 (dd, J=8.9, 5.6 Hz, 2H), 7.07-6.99 (m, 2H), 3.27 (s, 2H), 1.33 (s, 6H). MS(ESI) m/z 339.1 (M+H).

152G: 2-Bromo-3-(4-fluorophenyl)-7,7-dimethyl-1-((tetrahydro-2H-pyran-4-yl)methyl)-6,7-dihydro-1H-pyrrolo[3,2-c]pyridin-4(5H)-one: A suspension solution of 152F (30 mg, 0.089 mmol), 4-(bromomethyl)tetrahydropyran (16.73 mg, 0.093 mmol) and Cs$_2$CO$_3$ (43.5 mg, 0.133 mmol) in DMF (1 mL) was heated to 120° C. for 20 min and 140° C. for 1 h under microwave conditions. The reaction mixture was concentrated in vacuo. Water (2 mL) was added and stirred for 5 minutes. The solid was collected as the crude product which was purified by column chromatography on the Isco system to yield 152G (25 mg, 65% yield). MS(ESI) m/z 435.2 (M+H).

Example 152: A degassed solution of 151G (25 mg, 0.057 mmol), 4-(4,4,5,5-tetramethyl-1,3,2-dioxaborolan-2-yl) pyridine (23.55 mg, 0.115 mmol), PdCl$_2$(dppf)-CH$_2$Cl$_2$ adduct (4.69 mg, 5.74 µmol) and potassium phosphate tribasic, 2 M solution (0.086 mL, 0.172 mmol) in DMF (0.5 mL) was heated to 90° C. for 16 h. The crude reaction mixture was purified by preparative LCMS to yield 152 (4.2 mg, 17% yield). $^1$H NMR (500 MHz, DMSO-d$_6$) δ 8.49 (d, J=5.4 Hz, 2H), 7.16 (d, J=5.0 Hz, 3H), 7.08-6.99 (m, 2H), 6.92 (t, J=8.9 Hz, 2H), 4.00 (d, J=7.4 Hz, 2H), 3.70-3.54 (m, 2H, merge with DMSO), 3.16 (br. s., 2H), 3.00 (t, J=11.4 Hz, 2H), 1.62 (br. s., 1H), 1.42 (s, 6H), 1.20 (d, J=12.1 Hz, 2H), 0.81 (d, J=9.1 Hz, 2H). MS(ESI) m/z 434.4 (M+H).

Example 153

3-(4-Fluorophenyl)-7,7-dimethyl-2-(pyridin-4-yl)-6,7-dihydro-1H-pyrrolo[3,2-c]pyridin-4(5H)-one

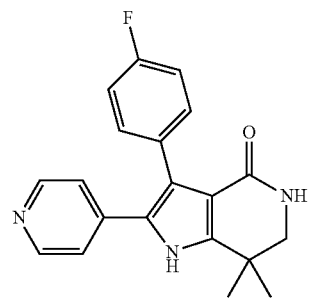 [SMILES: CC1(C)CNC(=O)c2c1[nH]c(-c1ccncc1)c2-c1ccc(F)cc1]

This compound was prepared from a degassed solution of 152F (20 mg, 0.059 mmol), 4-(4,4,5,5-tetramethyl-1,3,2-dioxaborolan-2-yl)pyridine (24.33 mg, 0.119 mmol), PdCl$_2$ (dppf)-CH$_2$Cl$_2$ adduct (4.84 mg, 5.93 µmol) and potassium phosphate tribasic, 2 M solution (0.089 mL, 0.178 mmol) in DMF (0.5 mL) which was heated to 90° C. for 1 h. The reaction mixture was purified using preparative LCMS to afford 153 (11.9 mg, 58% yield). $^1$H NMR (500 MHz, DMSO-d$_6$) δ 11.57 (s, 1H), 8.39 (d, J=6.1 Hz, 2H), 7.25 (dd, J=8.4, 5.7 Hz, 2H), 7.15-7.00 (m, 5H), 3.16 (d, J=2.0 Hz, 2H), 1.35 (s, 6H). MS(ESI) m/z 336.2 (M+H).

Example 154

3-(4-Fluorophenyl)-1,7,7-trimethyl-2-(pyridin-4-yl)-6,7-dihydro-1H-pyrrolo[3,2-c]pyridin-4(5H)-one

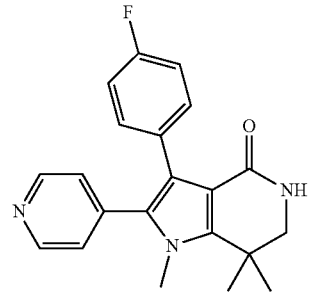 [SMILES: Cn1c(-c2ccncc2)c(-c2ccc(F)cc2)c2c1C(C)(C)CNC2=O]

154A: 2-Bromo-3-(4-fluorophenyl)-7,7-dimethyl-1-((tetrahydro-2H-pyran-4-yl)methyl)-6,7-dihydro-1H-pyrrolo[3,2-c]pyridin-4(5H)-one: A suspension solution of 152F (30 mg, 0.089 mmol), MeI (5.84 µl, 0.093 mmol) and Cs$_2$CO$_3$ (43.5 mg, 0.133 mmol) in DMF (1 mL) was heated to 100° C. for 20 min under microwave conditions.

The reaction mixture was concentrated, yielding a crude product to which water (2 mL) was added and stirred for 5 min. The solid was collected by filtration to yield 154A (17.4 mg, 82% yield). $^1$H NMR (400 MHz, CD$_3$OD) δ 7.36 (dd, J=8.8, 5.5 Hz, 2H), 7.05 (t, J=8.9 Hz, 2H), 3.81 (s, 3H), 3.29 (s, 2H), 1.46 (s, 6H). MS(ESI) m/z 351.1 (M+H).

Example 154: This compound was prepared using 153A (27 mg, 0.077 mmol) following the protocol for Example 152 to provide 153 (6.1 mg, 22% yield). $^1$H NMR (500 MHz, DMSO-$d_6$) δ 8.50 (d, J=5.0 Hz, 2H), 7.18-7.07 (m, 5H), 6.97 (t, J=8.9 Hz, 2H), 3.57 (s, 3H), 3.16 (d, J=1.7 Hz, 2H), 1.41 (s, 6H). MS(ESI) m/z 350.3 (M+H).

Example 155

2-(2-Chloropyridin-4-yl)-1-(2-fluoro-4-(trifluoromethyl)benzyl)-3-(4-fluorophenyl)-1H-pyrrolo[3,2-c]pyridin-4(5H)-one

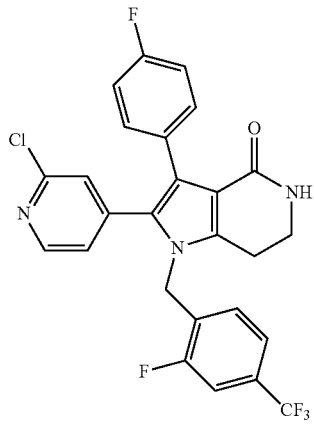 [SMILES: O=C1NCCc2c1c(-c1ccc(F)cc1)c(-c1ccnc(Cl)c1)n2Cc1ccc(C(F)(F)F)cc1F]

This compound was prepared from a solution of 6 (118 mg, 0.228 mmol) and DDQ (103 mg, 0.456 mmol) in dioxane (1.5 mL) which was stirred at rt for 1 h and heated to 100° C. for 16 h. The reaction mixture was concentrated and purified by column chromatography on the Isco system to yield 155 (111 mg, 66% yield). H NMR (500 MHz, DMSO-$d_6$) δ 11.04 (d, J=5.8 Hz, 1H), 8.29 (dd, J=5.1, 0.5 Hz, 1H), 7.63 (d, J=9.2 Hz, 1H), 7.47 (d, J=7.9 Hz, 1H), 7.28-7.22 (m, 3H), 7.18 (dd, J=7.2, 6.0 Hz, 1H), 7.11 (dd, J=5.2, 1.4 Hz, 1H), 7.09-7.02 (m, 2H), 6.84 (t, J=7.7 Hz, 1H), 6.66 (d, J=6.6 Hz, 1H), 5.52 (s, 2H). MS(ESI) m/z 516.3 (M+H).

Example 156

N-(4-(1-(2-Fluoro-4-(trifluoromethyl)benzyl)-3-(4-fluorophenyl)-4-oxo-4,5-dihydro-1H-pyrrolo[3,2-c]pyridin-2-yl)pyridin-2-yl)propionamide

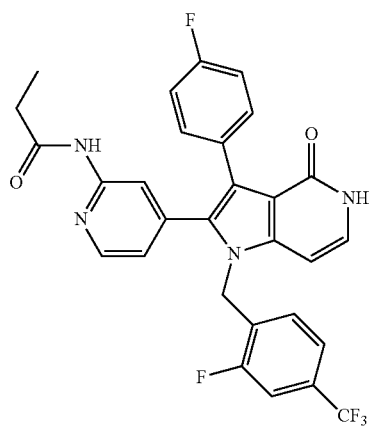 [SMILES: CCC(=O)Nc1cc(-c2c(-c3ccc(F)cc3)c3c(=O)[nH]ccc3n2Cc2ccc(C(F)(F)F)cc2F)ccn1]

This compound was prepared from a degassed solution of 155 (15 mg, 0.024 mmol) and propionamide (2.61 mg, 0.036 mmol) in DMF (1 mL). Xantphos (2.76 mg, 4.76 μmol), Pd$_2$(dba)$_3$ (4.36 mg, 4.76 μmol) and Cs$_2$CO$_3$ (20.17 mg, 0.062 mmol) were added and the reaction mixture was heated to 110° C. for 1 h. The reaction mixture was purified using preparative LCMS to provide 156 (4.6 mg, 34% yield). $^1$H NMR (500 MHz, DMSO-$d_6$) δ 10.98 (d, J=5.4 Hz, 1H), 10.39 (s, 1H), 8.18 (d, J=5.0 Hz, 1H), 7.77 (s, 1H), 7.56 (d, J=9.8 Hz, 1H), 7.46 (d, J=8.1 Hz, 1H), 7.25 (dd, J=8.4, 5.7 Hz, 2H), 7.17 (t, J=6.6 Hz, 1H), 7.02 (t, J=8.9 Hz, 2H), 6.85-6.73 (m, 2H), 6.64 (d, J=7.1 Hz, 1H), 5.43 (s, 2H), 2.29 (q, J=7.4 Hz, 2H), 0.97 (t, J=7.6 Hz, 3H). MS(ESI) m/z 553.3 (M+H).

Example 157

1-(2-Fluoro-4-(trifluoromethyl)benzyl)-3-(4-fluorophenyl)-2-(pyridin-4-yl)-1H-pyrrolo[3,2-c]pyridin-4(5H)-one

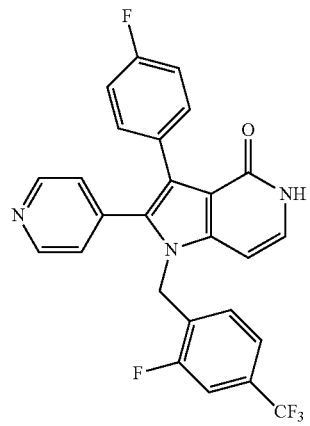 [SMILES: O=c1[nH]ccc2c1c(-c1ccc(F)cc1)c(-c1ccncc1)n2Cc1ccc(C(F)(F)F)cc1F]

This compound was prepared starting from a suspension solution of 155 (20 mg, 0.032 mmol), Pd/C (0.203 mg, 1.905 μmop and HCl (0.032 mL, 0.032 mmol) in MeOH (5 mL) which was stirred at 23° C. under a H$_2$ balloon (0.064 mg, 0.032 mmol) for 16 h. The reaction mixture was filtered and concentrated to yield a crude product which was purified using preparative LCMS to yield 157 (10.6 mg, 69% yield). $^1$H NMR (500 MHz, DMSO-$d_6$) δ 11.00 (d, J=5.7 Hz, 1H), 8.47 (d, J=5.4 Hz, 2H), 7.61 (d, J=10.1 Hz, 1H), 7.46 (d, J=8.1 Hz, 1H), 7.23 (dd, J=8.2, 5.9 Hz, 2H), 7.18-7.09 (m, 3H), 7.02 (t, J=8.8 Hz, 2H), 6.78 (t, J=7.7 Hz, 1H), 6.62 (d, J=7.1 Hz, 1H), 5.48 (s, 2H). MS(ESI) m/z 482.2 (M+H).

The following compounds in Table 8 were made in a similar manner as Example 155:

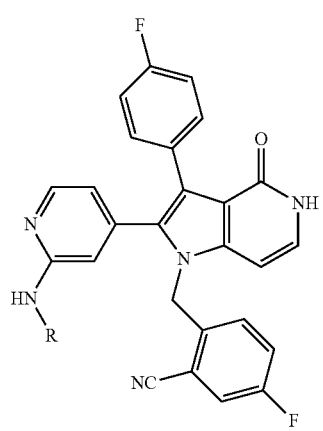

TABLE 8

| Ex. No. | R | M + H | ¹H NMR: (500 MHz, DMSO-d₆) |
|---|---|---|---|
| 158 | 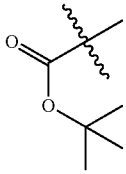 [SMILES: *C(=O)OC(C)(C)C] | 597.4 | δ 11.00 (d, J = 5.4 Hz, 1H), 9.78 (s, 1H), 8.11 (d, J = 5.0 Hz, 1H), 7.61 (d, J = 10.1 Hz, 1H), 7.51 (d, J = 8.1 Hz, 1H), 7.47 (s, 1H), 7.27 (dd, J = 8.1, 5.7 Hz, 2H), 7.16 (t, J = 6.4 Hz, 1H), 7.04 (t, J = 8.8 Hz, 2H), 6.81 (t, J = 7.6 Hz, 1H), 6.66 (d, J = 5.0 Hz, 1H), 6.59 (d, J = 7.4 Hz, 1H), 5.44 (s, 2H), 1.36 (s, 9H) |
| 159 | H | 497.3 | δ 7.95 (s, 1H), 7.83 (d, J = 6.7 Hz, 1H), 7.68 (d, J = 10.1 Hz, 1H), 7.50 (d, J = 8.1 Hz, 1H), 7.31 (dd, J = 8.1, 5.7 Hz, 2H), 7.19 (t, J = 6.4 Hz, 1H), 7.11 (t, J = 8.9 Hz, 2H), 6.88 (t, J = 7.7 Hz, 1H), 6.67 (s, 1H), 6.60 (d, J = 7.1 Hz, 1H), 6.50 (d, J = 6.4 Hz, 1H), 5.56 (s, 2H) |
| 160 | 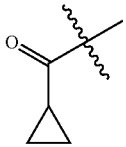 | 565.3 | δ 11.00 (d, J = 5.7 Hz, 1H), 10.77 (s, 1H), 8.19 (d, J = 5.0 Hz, 1H), 7.77 (s, 1H), 7.58 (d, J = 10.1 Hz, 1H), 7.47 (d, J = 8.1 Hz, 1H), 7.30-7.21 (m, 2H), 7.16 (t, J = 6.4 Hz, 1H), 7.03 (t, J = 8.8 Hz, 2H), 6.84-6.70 (m, 2H), 6.62 (d, J = 7.1 Hz, 1H), 5.43 (s, 2H), 1.91 (d, J = 4.4 Hz, 1H), 0.81-0.64 (m, 4H) |
| 161 | 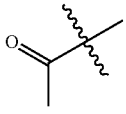 | 516.2 | δ 10.98 (br. s., 1H), 10.46 (br. s., 1H), 8.17 (d, J = 4.7 Hz, 1H), 7.77 (br. s., 1H), 7.57 (d, J = 9.8 Hz, 1H), 7.45 (d, J = 8.1 Hz, 1H), 7.27-7.20 (m, 2H), 7.14 (t, J = 6.4 Hz, 1H), 7.01 (t, J = 8.9 Hz, 2H), 6.78 (d, J = 5.7 Hz, 2H), 6.61 (d, J = 7.1 Hz, 1H), 5.44 (br. s., 2H), 1.99 (s, 3H) |

Example 162

3-(4-Fluorophenyl)-2-(pyridin-4-yl)-1-tosyl-6,7-dihydro-1H-pyrrolo[3,2-c]pyridin-4(5H)-one

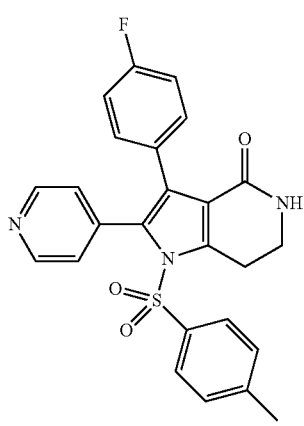 [SMILES: Cc1ccc(S(=O)(=O)n2c3c(c(-c4ccc(F)cc4)c2-c2ccncc2)C(=O)NCC3)cc1]

162A: 2-Bromo-3-(4-fluorophenyl)-1-tosyl-6,7-dihydro-1H-pyrrolo[3,2-c]pyridin-4(5H)-one: A solution of 2-bromo-3-(4-fluorophenyl)-6,7-dihydro-1H-pyrrolo[3,2-c]pyridin-4(5H)-one (300 mg, 0.970 mmol) in DMF (4 mL) at 23° C. was added Cs₂CO₃ (632 mg, 1.941 mmol), followed by p-toluenesulfonyl chloride (370 mg, 1.941 mmol). The reaction mixture was stirred at 23° C. for 3 d. The reaction mixture was diluted with EtOAc (100 mL) and washed with 10% LiCl solution (2×20 mL), brine (20 mL) and dried over Na₂SO₄. The organics were filtered and concentrated in vacuo to yield a crude product which was purified by silica gel chromatography with EtOAc to yield 162A (260.5 mg, 58%). ¹H NMR (400 MHz, CD₃OD) δ 7.93 (d, J=8.6 Hz, 2H), 7.49 (d, J=7.9 Hz, 2H), 7.28-7.22 (m, 2H), 7.07-7.00 (m, 2H), 3.61-3.54 (m, 2H), 3.43-3.37 (m, 2H), 2.47 (s, 3H). MS(ESI) m/z 463.0 (M+H).

Example 162: This compound was prepared using 161A (27 mg, 0.077 mmol) following the protocol for Example 1 to provide 161 (16.1 mg, 54% yield). ¹H NMR (500 MHz, DMSO-d₆) δ 8.43 (br d, J=5.0 Hz, 2H), 7.47 (br d, J=7.7 Hz, 3H), 7.44-7.39 (m, 2H), 7.07-7.01 (m, 4H), 6.93 (t, J=8.9 Hz, 2H), 3.44 (br s, 2H), 3.26-3.19 (m, 2H), 2.40 (s, 3H). MS(ESI) m/z 462.2 (M+H).

The following compounds in Table 9 were made in a similar manner as Example 9 or Example 14:

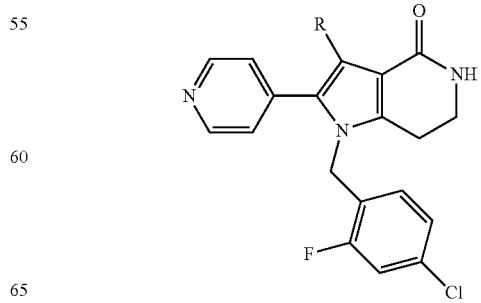

TABLE 9

| Ex. No. | R | M + H | ¹H NMR |
|---|---|---|---|
| 163 | tert-butyl (3-substituted phenyl)carbamate | 547.5 | (500 MHz, acetone-d₆) δ 8.44-8.39 (m, 2H), 8.27 (br s, 1H), 7.47-7.40 (m, 2H), 7.26-7.19 (m, 2H), 7.07-7.04 (m, 2H), 7.02 (t, J = 7.9 Hz, 1H), 6.82-6.73 (m, 2H), 6.28 (br s, 1H), 5.27 (s, 2H), 3.60-3.54 (m, 2H), 2.89 (t, J = 6.8 Hz, 2H), 1.44 (s, 9H) |
| 164 | 5-methylthiophen-2-yl | 452.4 | (500 MHz, acetone-d₆) δ 8.54-8.47 (m, 2H), 7.24-7.18 (m, 2H), 7.18-7.14 (m, 2H), 6.98 (d, J = 3.6 Hz, 1H), 6.74 (t, J = 8.4 Hz, 1H), 6.52-6.48 (m, 1H), 6.30 (br s, 1H), 5.20 (s, 2H), 3.59-3.52 (m, 2H), 2.87 (br t, J = 6.8 Hz, 2H), 2.31 (d, J = 1.1 Hz, 3H) |
| 165 | 1-methyl-1H-pyrazol-4-yl | 436.4 | (500 MHz, acetone-d₆) δ 8.58-8.52 (m, 2H), 7.92 (s, 1H), 7.23-7.15 (m, 4H), 6.98 (s, 1H), 6.69 (t, J = 8.4 Hz, 1H), 6.31 (br s, 1H), 5.17 (s, 2H), 3.75 (s, 3H), 3.55 (td, J = 6.8, 2.8 Hz, 2H), 2.88-2.85 (m, 2H) |
| 166 | 3-fluoropyridin-4-yl | 451.3 | (500 MHz, acetone-d₆) δ 8.47 (br d, J = 5.9 Hz, 2H), 8.28 (br d, J = 1.7 Hz, 1H), 8.20 (br d, J = 4.9 Hz, 1H), 7.27-7.20 (m, 3H), 7.12-7.07 (m, 2H), 6.81 (br t, J = 8.2 Hz, 2H), 6.33 (br s, 1H), 5.34 (s, 2H), 3.61 (td, J = 6.8, 2.7 Hz, 2H), 2.93 (br t, J = 6.8 Hz, 2H) |
| 167 | methyl 3-substituted benzoate | 490.0 | (500 MHz, acetone-d₆) δ 8.46-8.42 (m, 2H), 7.96 (t, J = 1.6 Hz, 1H), 7.78 (dt, J = 7.7, 1.5 Hz, 1H), 7.45-7.41 (m, 1H), 7.29-7.18 (m, 3H), 7.09-7.06 (m, 2H), 6.83-6.76 (m, 1H), 6.32 (br s, 1H), 5.30 (s, 2H), 3.81 (s, 3H), 3.60 (td, J = 6.8, 2.7 Hz, 2H), 2.91 (t, J = 6.8 Hz, 2H) |
| 168 | 2-methylpyridin-4-yl | 447.0 | (500 MHz, acetone-d₆) δ 8.51-8.44 (m, 2H), 8.17 (d, J = 5.1 Hz, 1H), 7.26-7.17 (m, 2H), 7.12-7.07 (m, 3H), 6.93 (dd, J = 5.1, 1.1 Hz, 1H), 6.78 (t, J = 8.3 Hz, 1H), 6.37 (br s, 1H), 5.28 (s, 2H), 3.59 (td, J = 6.8, 2.8 Hz, 2H), 2.91 (t, J = 6.8 Hz, 2H), 2.32 (s, 3H) |
| 169 | 3-aminophenyl | 447.4 | (500 MHz, acetone-d₆) δ 8.42 (br s, 2H), 7.25-7.19 (m, 2H), 7.08-7.04 (m, 2H), 6.88 (d, J = 7.6 Hz, 1H), 6.76 (br t, J = 8.3 Hz, 1H), 6.50 (t, J = 1.7 Hz, 1H), 6.46-6.42 (m, 1H), 6.38 (br s, 1H), 5.27 (s, 2H), 3.59-3.54 (m, 2H), 2.89 (br t, J = 6.8 Hz, 2H) |
| 170 | N-(3-substituted phenyl)butanamide | 517.2 | (400 MHz, CD₃OD) δ 8.36 (br d, J = 4.6 Hz, 2H), 7.44-7.38 (m, 2H), 7.19-7.05 (m, 5H), 6.87 (br d, J = 7.8 Hz, 1H), 6.67 (t, J = 8.1 Hz, 1H), 5.25 (s, 2H), 3.58 (t, J = 7.0 Hz, 2H), 2.91 (br t, J = 6.8 Hz, 2H), 2.27 (t, J = 7.3 Hz, 2H), 1.67 (dq, J = 14.8, 7.4 Hz, 2H), 0.96 (t, J = 7.4 Hz, 3H) |

The following compounds in Table 10 were made in a similar manner as Example 9 or Example 14:

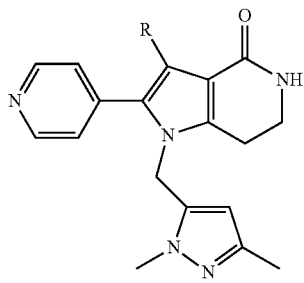

TABLE 10

| Ex. No. | R | M + H | ¹H NMR |
|---|---|---|---|
| 171 | *tert-butyl (3-substituted-phenyl)carbamate* | 513.5 | (500 MHz, acetone-d$_6$) δ 8.45-8.39 (m, 2H), 8.26 (br s, 1H), 7.46 (br d, J = 8.1 Hz, 1H), 7.39 (s, 1H), 7.06-7.01 (m, 3H), 6.79 (dt, J = 7.7, 1.2 Hz, 1H), 6.22 (br s, 1H), 5.22 (s, 2H), 3.60-3.55 (m, 5H), 2.91-2.87 (m, 5H), 1.44 (s, 9H) |
| 172 | *methyl 3-substituted-benzoate* | 456.1 | (500 MHz, acetone-d$_6$) δ 8.46-8.43 (m, 2H), 7.94 (t, J = 1.5 Hz, 1H), 7.78 (dt, J = 7.8, 1.4 Hz, 1H), 7.42 (dt, J = 7.7, 1.5 Hz, 1H), 7.29-7.24 (m, 1H), 7.08-7.03 (m, 2H), 6.25 (br s, 1H), 5.63 (s, 1H), 5.25 (s, 2H), 3.80 (s, 3H), 3.63-3.56 (m, 5H), 2.91 (t, J = 6.9 Hz, 3H), 2.08 (s, 3H) |
| 173 | *3,5-dimethylisoxazol-4-yl phenyl* | 493.5 | (500 MHz, CD$_3$OD) δ 8.46-8.39 (m, 2H), 7.37-7.28 (m, 2H), 7.18-7.11 (m, 3H), 7.06-7.02 (m, 1H), 5.60 (s, 1H), 5.20 (s, 2H), 3.61 (t, J = 6.9 Hz, 2H), 3.56 (s, 3H), 2.93 (t, J = 6.9 Hz, 2H), 2.19 (s, 3H), 2.12 (s, 3H), 2.02 (s, 3H) |
| 174 | *3-aminophenyl* | 413.4 | (500 MHz, acetone-d$_6$) δ 8.43 (br d, J = 5.6 Hz, 2H), 7.04 (d, J = 6.6 Hz, 2H), 6.89-6.84 (m, 1H), 6.50-6.48 (m, 1H), 6.47-6.42 (m, 1H), 6.35 (br s, 1H), 5.60 (s, 1H), 5.22 (s, 2H), 3.60-3.52 (m, 5H), 2.88 (t, J = 6.8 Hz, 2H), 2.08 (s, 3H) |
| 175 | *N-(3-substituted-phenyl)-2-phenylacetamide* | 531.3 | (500 MHz, acetone-d$_6$) δ 9.23 (br s, 1H), 8.42 (br s, 2H), 7.61 (br d, J = 7.9 Hz, 1H), 7.49 (br s, 1H), 7.40-7.26 (m, 4H), 7.25-7.18 (m, 1H), 7.05-6.97 (m, 3H), 6.76 (d, J = 7.5 Hz, 1H), 6.27 (br s, 1H), 5.59 (s, 1H), 5.26-5.19 (m, 1H), 5.22 (s, 1H), 3.60-3.55 (m, 6H), 2.88 (t, J = 6.8 Hz, 2H), 2.80 (br s, 2H), 2.08 (s, 3H) |
| 176 | *N-(3-substituted-phenyl)benzamide* | 517.3 | (500 MHz, acetone-d$_6$) δ 9.49 (s, 1H), 8.43 (br d, J = 5.6 Hz, 2H), 7.98-7.92 (m, 2H), 7.79-7.71 (m, 2H), 7.57-7.50 (m, 1H), 7.49-7.42 (m, 2H), 7.11-7.03 (m, 3H), 6.83 (d, J = 7.7 Hz, 1H), 6.32 (br s, 1H), 5.61 (s, 1H), 5.24 (s, 2H), 3.61-3.54 (m, 5H), 2.90 (t, J = 6.8 Hz, 2H), 2.09 (s, 3H) |
| 177 | *N-(3-substituted-phenyl)cyclopropanecarboxamide* | 481.3 | (500 MHz, acetone-d$_6$) δ 9.33 (br s, 1H), 8.43 (br d, J = 5.4 Hz, 2H), 7.62 (br d, J = 7.9 Hz, 1H), 7.49 (s, 1H), 7.08-6.96 (m, 3H), 6.76 (d, J = 7.7 Hz, 1H), 6.29 (br s, 1H), 5.60 (s, 1H), 5.22 (s, 2H), 3.60-3.54 (m, 5H), 2.89 (t, J = 6.8 Hz, 2H), 2.08 (s, 3H), 1.74-1.66 (m, 1H), 0.86-0.81 (m, 2H), 0.73-0.67 (m, 2H) |
| 178 | *N-(3-substituted-phenyl)formamide* | 441.2 | (500 MHz, acetone-d$_6$) δ 9.18-9.03 (m, 1H), 8.48-8.41 (m, 2H), 8.24 (s, 1H), 7.59 (d, J = 8.1 Hz, 1H), 7.49 (s, 1H), 7.10-7.02 (m, 3H), 6.91-6.84 (m, 1H), 6.30 (br s, 1H), 5.60 (s, 1H), 5.23 (s, 2H), 3.60-3.55 (m, 5H), 2.93-2.87 (m, 2H), 2.08 (s, 3H) |
| 179 | *N-(3-substituted-phenyl)propanamide* | 469.3 | (500 MHz, acetone-d$_6$) δ (br s, 1H), 8.43 (br d, J = 5.8 Hz, 2H), 7.61 (br d, J = 7.7 Hz, 1H), 7.49 (s, 1H), 7.07-6.96 (m, 3H), 6.75 (d, J = 7.7 Hz, 1H), 6.29 (br s, 1H), 5.60 (s, 1H), 5.22 (s, 2H), 3.62-3.53 (m, 5H), 2.91-2.89 (m, 2H), 2.29 (q, J = 7.5 Hz, 2H), 2.08 (s, 3H), 1.09 (t, J = 7.5 Hz, 3H) |

TABLE 10-continued

| Ex. No. | R | M + H | ¹H NMR |
|---|---|---|---|
| 180 | 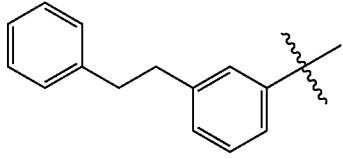 [SMILES: *c1cccc(CCc2ccccc2)c1] | 502.3 | (400 MHz, CD₃OD) δ 8.48 (br s, 2H), 7.28-6.92 (m, 11H), 5.59 (s, 1H), 5.19 (s, 2H), 3.63-3.52 (m, 5H), 2.90 (t, J = 7.0 Hz, 2H), 2.82-2.65 (m, 4H), 2.13 (s, 3H) |
| 181 | 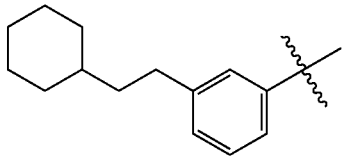 [SMILES: *c1cccc(CCC2CCCCC2)c1] | 508.3 | (400 MHz, CD₃OD) δ 8.38 (br d, J = 5.4 Hz, 2H), 7.14-7.04 (m, 4H), 6.96 (br d, J = 7.1 Hz, 1H), 6.90 (s, 1H), 5.59 (s, 1H), 5.19 (s, 2H), 3.63-3.54 (m, 5H), 2.91 (t, J = 7.0 Hz, 2H), 2.50-2.40 (m, 2H), 2.12 (s, 3H), 1.69 (br d, J = 11.5 Hz, 5H), 1.31-1.15 (m, 6H), 0.94-0.81 (m, 2H) |

The following compounds in Table 11 were made in a similar manner as Example 1:

Example 185 tert-Butyl (3-(2-(2-(cyclopropanecarboxamido)pyridin-4-yl)-1-((1,3-dimethyl-1H-pyrazol-5-yl)methyl)-4-oxo-4,5,6,7-tetrahydro-1H-pyrrolo[3,2-c]pyridin-3-yl)phenyl)carbamate

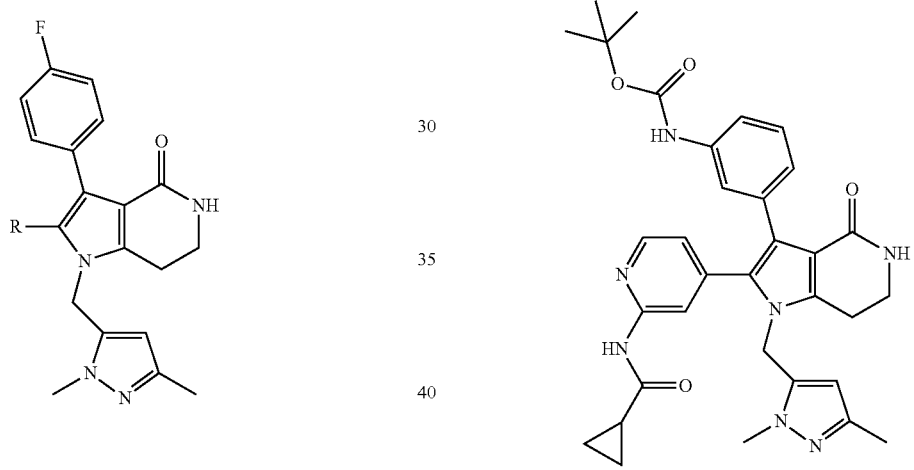

TABLE 11

| Ex. No. | R | M + H | ¹H NMR |
|---|---|---|---|
| 182 | 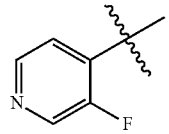 [SMILES: *c1ccncc1F] | 434.3 | (500 MHz, CD₃OD) δ 8.39 (br s, 1H), 8.27 (br d, J = 4.4 Hz, 1H), 7.21-7.12 (m, 3H), 6.93-6.84 (m, 2H), 5.52 (s, 1H), 5.32-5.04 (m, 2H), 3.59 (br t, J = 6.8 Hz, 2H), 3.50 (s, 3H), 2.93 (br s, 2H), 2.06 (s, 3H) |
| 183 | 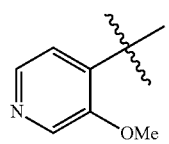 | 446.2 | (400 MHz, CD₃OD) δ 8.26 (s, 1H), 8.01 (d, J = 4.9 Hz, 1H), 7.14 (dd, J = 8.8, 5.6 Hz, 2H), 6.93 (d, J = 4.6 Hz, 1H), 6.85 (t, J = 8.9 Hz, 2H), 5.53 (s, 1H), 5.18-5.07 (m, 1H), 5.04-4.95 (m, 1H), 3.76 (s, 3H), 3.58 (t, J = 6.8 Hz, 2H), 3.46 (s, 3H), 3.01-2.81 (m, 2H), 2.07 (s, 3H) |
| 184 | 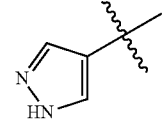 | 405.4 | (400 MHz, CD₃OD) δ 7.41-7.28 (m, 1H), 7.23 (dd, J = 8.8, 5.6 Hz, 3H), 6.94-6.84 (m, 2H), 5.60 (s, 1H), 5.08 (s, 2H), 3.61-3.54 (m, 5H), 2.87 (t, J = 7.0 Hz, 2H), 2.14 (s, 3H) |

185A: 3-Bromo-2-(2-chloropyridin-4-yl)-1-((1,3-dimethyl-1H-pyrazol-5-yl)methyl)-6,7-dihydro-1H-pyrrolo[3,2-c]pyridin-4(5H)-one: A mixture of 3C (1 g, 3.06 mmol), 5-(chloromethyl)-1,3-dimethyl-1H-pyrazole (0.531 g, 3.67 mmol) and cesium carbonate (2.99 g, 9.19 mmol) in DMA (12 mL) was stirred at rt for 3 d. The reaction mixture was absorbed onto CELITE® and chromatographed on an 80 gm ISCO silica gel cartridge, eluting with a 0-9% MeOH/$CH_2Cl_2$ gradient. The purest fractions were concentrated to afford 610 mg of product. The mixed fractions were concentrated to afford ~350 mg of material that was triturated with ethyl acetate to afford 155 mg of a white solid. This was combined with the purest fractions to afford 185A (766 mg, 1.762 mmol, 58% yield) as a yellow solid. $^1$H NMR (400 MHz, DMSO-$d_6$) δ 8.47 (d, J=5.1 Hz, 1H), 7.42 (d, J=0.6 Hz, 1H), 7.35-7.26 (m, 2H), 5.46 (s, 1H), 5.20 (s, 2H), 3.50 (s, 3H), 3.39 (td, J=6.7, 2.5 Hz, 2H), 2.79 (t, J=6.8 Hz, 2H), 2.00 (s, 3H). MS(ESI) m/z 436.3 (M+H).

Example 185: This compound was prepared using 185A following the protocols for Example 14, then Example 3 to provide 185. $^1$H NMR (500 MHz, acetone-$d_6$) δ 9.72 (s, 1H), 8.18 (br s, 1H), 8.10 (s, 1H), 8.05 (d, J=5.1 Hz, 1H), 7.50 (br d, J=7.8 Hz, 1H), 7.36 (s, 1H), 7.03 (t, J=7.8 Hz, 1H), 6.86 (br d, J=8.1 Hz, 1H), 6.65 (dd, J=5.1, 1.5 Hz, 1H), 6.18 (br s, 1H), 5.53 (s, 1H), 5.24 (s, 2H), 3.63-3.50 (m, 5H), 2.89 (t, J=6.8 Hz, 2H), 2.80 (s, 3H), 1.45 (s, 9H). MS(ESI) m/z 596.3 (M+H).

What is claimed is:

1. A compound according to Formula (I):

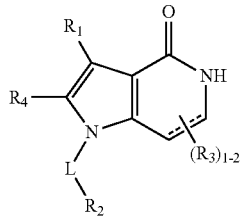

(I)

or a pharmaceutically acceptable salt thereof, wherein:
--- is an optional bond;
$R_1$ is selected from —$(CR_dR_d)_r$—$C_{3-10}$ carbocyclyl substituted with 1-5 $R_5$, —$CR_d$=$CR_d$—$C_{3-10}$ carbocyclyl substituted with 1-5 $R_5$, and 3- to 15-membered heterocyclyl comprising carbon atoms and 1 to 3 heteroatoms selected from N, O, S, and substituted with 1-5 $R_5$;
L is selected from —$(CR_dR_d)_r$— and —$S(O)_p$—;
$R_2$ is selected carbocyclyl substituted with 1-8 $R_7$, 3- to 15-membered heterocyclyl, comprising carbon atoms and 1 to 4 heteroatoms selected from N, O, S, wherein said heterocyclyl is substituted with 1-8 $R_7$;
$R_3$ is selected from H, CN, $C_{1-4}$ alkyl substituted with 0-3 $R_e$, —C(=O)$OR_b$, —C(=O)$NR_aR_a$, —C(=O)$R_b$, —$NR_aC$(=O)$R_b$, —$NR_aC$(=O)$OR_b$, $C_{3-6}$carbocycle substituted with 0-3 $R_e$, and 3- to 15-membered heterocycle substituted with 0-3 $R_e$;
$R_4$ is selected from

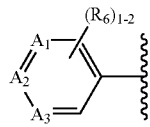

and 5-membered heteroaryl substituted with 1-5 $R_6$;
$A_1$, $A_2$, and $A_3$ are independently selected from N and $CR_6$; provided $A_1$, $A_2$, and $A_3$ are not all nitrogen;
$R_5$ is selected from H, $C_{1-4}$ alkyl substituted with 0-3 $R_e$, F, Cl, Br, =O, CN, $NO_2$, —$(CH_2)_rCN$, —$(CH_2)_rOR_b$, $(CH_2)_pS(O)_pR_c$, —$(CH_2)_rC(=O)R_b$, —$(CH_2)_rNR_aR_a$, —$(CH_2)_rC(=O)NR_aR_a$, —$(CH_2)_rNR_aC(=O)R_b$, —$(CH_2)_rNR_aC(=O)OR_b$, —$(CH_2)_rOC(=O)NR_aR_a$, —$(CH_2)_rNR_aC(=O)NR_aR_a$, —$(CH_2)_rC(=O)OR_b$, —$(CH_2)_rS(O)_2NR_aR_a$, —$(CH_2)_rNR_aS(O)_2NR_aR_a$, —$(CH_2)_rNR_aS(O)_2R_c$, $(CH_2)_r$-carbocyclyl substituted with 0-3 $R_e$, and —$(CH_2)_r$-3- to 15-membered heterocyclyl substituted with 0-3 $R_e$;
$R_6$ is selected from H, F, Cl, Br, $C_{1-4}$ alkyl substituted with 0-3 $R_e$, —$(CH_2)_rCN$, —$(CH_2)_rOR_b$, $(CH_2)_rS(O)_pR_c$, —$(CH_2)_rC(=O)R_b$, —$(CH_2)_rNR_aR_a$, —$(CH_2)_rC(=O)NR_aR_a$, —$(CH_2)_rC(=O)$—$C_{1-4}$ alkyl substituted with 0-3 $R_e$, —$(CH_2)_rNR_aC(=O)R_b$, —$(CH_2)_rNR_aC(=O)OR_b$, —$(CH_2)_rOC(=O)NR_aR_a$, —$(CH_2)_rNR_aC(=O)NR_aR_a$, —$(CH_2)_rC(=O)OR_b$, —$(CH_2)_rS(O)_2NR_aR_a$, —$(CH_2)_rNR_aS(O)_2NR_aR_a$, —$(CH_2)_rNR_aS(O)_2R_c$, $(CH_2)_r$-carbocyclyl substituted with 0-3 $R_e$, and —$(CH_2)_r$-3- to 15-membered heterocyclyl substituted with 0-3 $R_e$; alternatively, two adjacent $R_6$ groups are taken together to form a heterocycle;
$R_7$, at each occurrence, is independently selected from H, F, Cl, Br, =O, CN, $NO_2$, —$OR_b$, —$S(O)_pR_c$, —$C(=O)R_b$, —$(CR_dR_d)_rNR_aR_a$, —$(CR_dR_d)_rC(=O)NR_aR_a$, —$NR_aC(=O)R_b$, —$NR_aC(=O)OR_b$, —$OC(=O)NR_aR_a$, —$NR_aC(=O)NR_aR_a$, —$(CR_dR_d)_rC(=O)OR_b$, —$S(O)_2NR_aR_a$, —$NR_aS(O)_2NR_aR_a$, —$NR_aS(O)_2R_c$, $C_{1-6}$ alkyl substituted with 0-5 $R_e$, —$(CR_dR_d)_r$—$C_{3-6}$carbocyclyl substituted with 0-5 $R_e$, and —$(CR_dR_d)_r$-3- to 15-membered heterocyclyl substituted with 0-5 $R_e$;
$R_a$, at each occurrence, is independently selected from H, CN, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-3- to 15-membered heterocyclyl substituted with 0-5 $R_e$; or $R_a$ and $R_a$ together with the nitrogen atom to which they are both attached form a heterocyclic ring substituted with 0-5 $R_e$;
$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-3- to 15-membered heterocyclyl substituted with 0-5 $R_e$;
$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and 3- to 15-membered heterocyclyl;
$R_d$, at each occurrence, is independently selected from H and $C_{1-4}$alkyl substituted with 0-5 $R_e$; or $R_d$ and $R_d$ together are =O;
$R_e$, at each occurrence, is independently selected from $C_{1-6}$ alkyl substituted with 0-5 $R_f$, $C_{2-6}$ alkenyl, $C_{2-6}$ alkynyl, $C_{6-12}$ aryl, —$(CH_2)_r$—$C_{3-6}$ cycloalkyl, F, Cl, Br, CN, $NO_2$, =O, $CO_2H$, —C(=O)$NR_fR_f$, —$(CH_2)_rOR_f$, $SR_f$, and —$(CH_2)_rNR_fR_f$;
$R_f$, at each occurrence, is independently selected from H, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

p, at each occurrence, is independently selected from zero, 1, and 2; and r, at each occurrence, is independently selected from zero, 1, 2, 3, and 4.

2. The compound according to claim 1, having Formula (II):

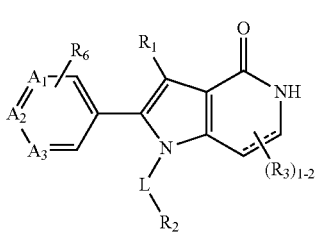

or a pharmaceutically acceptable salt thereof, wherein:
--- is an optional bond;

$A_1$, $A_2$, and $A_3$ are independently selected from N and $CR_6$;

$R_1$ is selected from $C_{6-12}$ aryl substituted with 1-4 $R_5$, and 5- to 12-membered heteroaryl comprising carbon atoms and 1 to 3 heteroatoms selected from N, O, S, and substituted with 1-4 $R_5$;

L is selected from $-(CR_dR_d)_r-$ and $-S(O)_p-$;

$R_2$ is selected from $C_{3-12}$ carbocyclyl substituted with 1-5 $R_7$, and 5- to 12-membered heterocyclyl comprising carbon atoms and 1 to 4 heteroatoms selected from N, O, S, and substituted with 1-5 $R_7$;

$R_3$ is selected from H and $C_{1-4}$ alkyl substituted with 0-3 $R_e$;

$R_5$ is selected from H, $C_{1-4}$ alkyl substituted with 0-3 $R_e$, F, Cl, Br, =O, CN, $NO_2$, $-(CH_2)_rOR_b$, $-(CH_2)_rCN$, $(CH_2)_rS(O)_pR_c$, $-(CH_2)_rC(=O)R_b$, $-(CH_2)_rNR_aR_a$, $-(CH_2)_rC(=O)NR_aR_a$, $-(CH_2)_rNR_aC(=O)R_b$, $-(CH_2)_rNR_aC(=O)OR_b$, $-(CH_2)_rOC(=O)NR_aR_a$, $-(CH_2)_rNR_aC(=O)NR_aR_a$, $-(CH_2)_rC(=O)OR_b$, $-(CH_2)_rS(O)_2NR_aR_a$, $-(CH_2)_rNR_aS(O)_2NR_aR_a$, $-(CH_2)_rNR_aS(O)_2R_c$, $(CH_2)_r$-carbocyclyl substituted with 0-3 $R_e$, and $-(CH_2)_r$-3- to 15-membered heterocyclyl substituted with 0-3 $R_e$;

$R_6$ is selected from H, F, Cl, Br, $C_{1-4}$ alkyl substituted with 0-3 $R_e$, $-(CH_2)_rCN$, $-(CH_2)_rOR_b$, $(CH_2)_rS(O)_pR_c$, $-(CH_2)_rC(=O)R_b$, $-(CH_2)_rNR_aR_a$, $-(CH_2)_rC(=O)NR_aR_a$, $-(CH_2)_rC(=O)-C_{1-4}$ alkyl substituted with 0-3 $R_e$, $-(CH_2)_rNR_aC(=O)R_b$, $-(CH_2)_rNR_aC(=O)OR_b$, $-(CH_2)_rOC(=O)NR_aR_a$, $-(CH_2)_rNR_aC(=O)NR_aR_a$, $-(CH_2)_rC(=O)OR_b$, $-(CH_2)_rS(O)_2NR_aR_a$, $-(CH_2)_rNR_aS(O)_2NR_aR_a$, $-(CH_2)_rNR_aS(O)_2R_c$, $(CH_2)_r$-carbocyclyl substituted with 0-3 $R_e$, and $-(CH_2)_r$-3- to 15-membered heterocyclyl substituted with 0-3 $R_e$;

$R_7$, at each occurrence, is independently selected from H, F, Cl, Br, =O, CN, $NO_2$, $-OR_b$, $-S(O)_pR_c$, $-C(=O)R_b$, $-(CR_dR_d)_rNR_aR_a$, $-(CR_dR_d)_rC(=O)NR_aR_a$, $-NR_aC(=O)R_b$, $-NR_aC(=O)OR_b$, $-OC(=O)NR_aR_a$, $-NR_aC(=O)NR_aR_a$, $-(CR_dR_d)_rC(=O)OR_b$, $-S(O)_2NR_aR_a$, $-NR_aS(O)_2NR_aR_a$, $-NR_aS(O)_2R_c$, $C_{1-6}$ alkyl substituted with 0-5 $R_e$, $-(CR_dR_d)_r-C_{3-6}$ carbocyclyl substituted with 0-5 $R_e$, and $-(CR_dR_d)_r$-3- to 15-membered heterocyclyl substituted with 0-5 $R_e$;

$R_a$, at each occurrence, is independently selected from H, CN, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $-(CH_2)_r-C_{3-10}$ carbocyclyl substituted with 0-5 $R_e$, and $-(CH_2)_r$-3- to 15-membered heterocyclyl substituted with 0-5 $R_e$; or $R_a$ and $R_a$ together with the nitrogen atom to which they are both attached form a 3- to 15-membered heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $-(CH_2)_r-C_{3-10}$ carbocyclyl substituted with 0-5 $R_e$, and $-(CH_2)_r$-3- to 15-membered heterocyclyl substituted with 0-5 $R_e$;

$R_c$, at each occurrence, is independently selected from $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $C_{3-6}$ carbocyclyl, and 3- to 15-membered heterocyclyl;

$R_d$, at each occurrence, is independently selected from H and $C_{1-4}$ alkyl substituted with 0-5 $R_e$; or $R_d$ and $R_d$ together are =O;

$R_e$, at each occurrence, is independently selected from $C_{1-6}$ alkyl substituted with 0-5 $R_f$, $C_{2-6}$ alkenyl, $C_{2-6}$ alkynyl, $C_{6-12}$ aryl, $-(CH_2)_r-C_{3-6}$ cycloalkyl, F, Cl, Br, CN, $NO_2$, =O, $CO_2H$, $-(CH_2)_rOR_f$, $SR_f$, and $-(CH_2)_rNR_fR_f$;

$R_f$, at each occurrence, is independently selected from H, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$ alkyl;

p, at each occurrence, is independently selected from zero, 1, and 2; and r, at each occurrence, is independently selected from zero, 1, 2, 3, and 4.

3. The compound according to claim 2, or a pharmaceutically acceptable salt thereof, wherein:

$R_1$ is selected from phenyl, pyridyl, pyrimidinyl, pyrazinyl, pyridazinyl, triazinyl, furyl, thienyl, imidazolyl, thiazolyl, indolyl, oxazolyl, isoxazolyl, pyrazolyl, triazolyl, tetrazolyl, indazolyl, 1,2,4-thiadiazolyl, isothiazolyl, quinolinyl, and isoquinolinyl, each substituted with substituted with 0-4 $R_5$;

$R_5$ is selected from H, $C_{1-4}$ alkyl substituted with 0-3 $R_e$, F, Cl, Br, =O, CN, $NO_2$, $-(CH_2)_rOR_b$, $-S(O)_pR_c$, $-CN$, $-(CH_2)_rC(=O)R_b$, $-(CH_2)_rNR_aR_a$, $-(CH_2)_rC(=O)NR_aR_a$, $-(CH_2)_rNHC(=O)R_b$, $-(CH_2)_rNHC(=O)OR_b$, $-(CH_2)_rOC(=O)NR_aR_a$, $-(CH_2)_rNHC(=O)NR_aR_a$, $-(CH_2)_rC(=O)OR_b$, $-(CH_2)_rS(O)_2NR_aR_a$, $-(CH_2)_rNHS(O)_2NR_aR_a$, $-(CH_2)_rNHS(O)_2R_c$, $(CH_2)_r$-carbocyclyl substituted with 0-3 $R_e$, and $-(CH_2)_r$-3- to 15-membered heterocyclyl substituted with 0-3 $R_e$;

$R_a$, at each occurrence, is independently selected from H, CN, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $-(CH_2)_r-C_{3-10}$ carbocyclyl substituted with 0-5 $R_e$, and $-(CH_2)_r$-3- to 15-membered heterocyclyl substituted with 0-5 $R_e$; or $R_a$ and $R_a$ together with the nitrogen atom to which they are both attached form a 3- to 15-membered heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $-(CH_2)_r-C_{3-10}$ carbocyclyl substituted with 0-5 $R_e$, and $-(CH_2)_r$-3- to 15-membered heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and 3- to 15-membered heterocyclyl;

$R_e$, at each occurrence, is independently selected from $C_{1-6}$ alkyl substituted with 0-5 $R_f$, $C_{2-6}$ alkenyl, $C_{2-6}$ alkynyl, $C_{6-12}$ aryl, —$(CH_2)_r$—$C_{3-6}$ cycloalkyl, F, Cl, Br, CN, $NO_2$, =O, $CO_2H$, —$(CH_2)_rOR_f$, $SR_f$, and —$(CH_2)_rNR_fR_f$;

$R_f$, at each occurrence, is independently selected from H, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

p, at each occurrence, is independently selected from zero, 1, and 2; and r, at each occurrence, is independently selected from zero, 1, 2, 3, and 4.

4. The compound according to claim 3, or a pharmaceutically acceptable salt thereof, wherein:

$R_1$ is selected from:

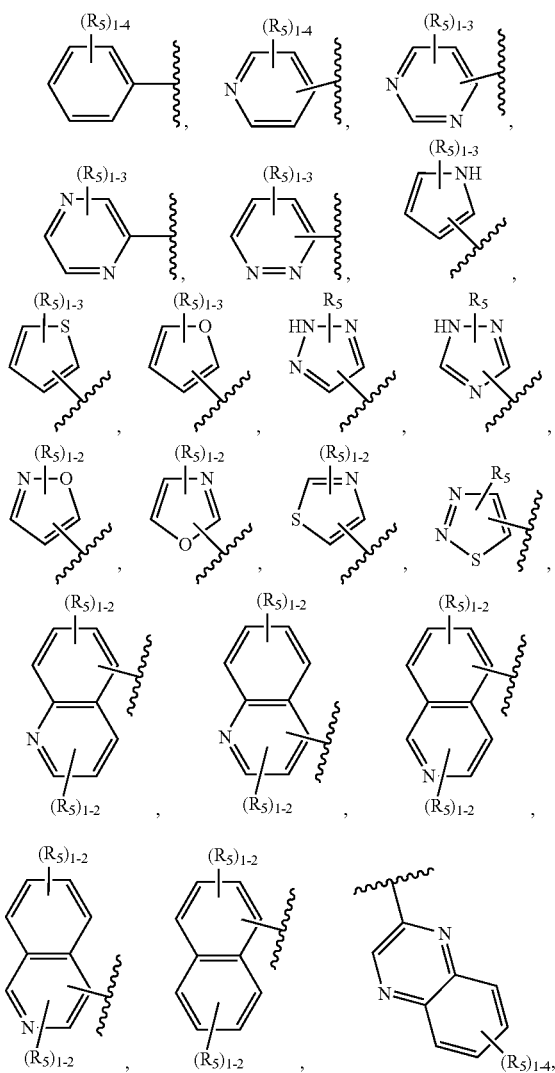

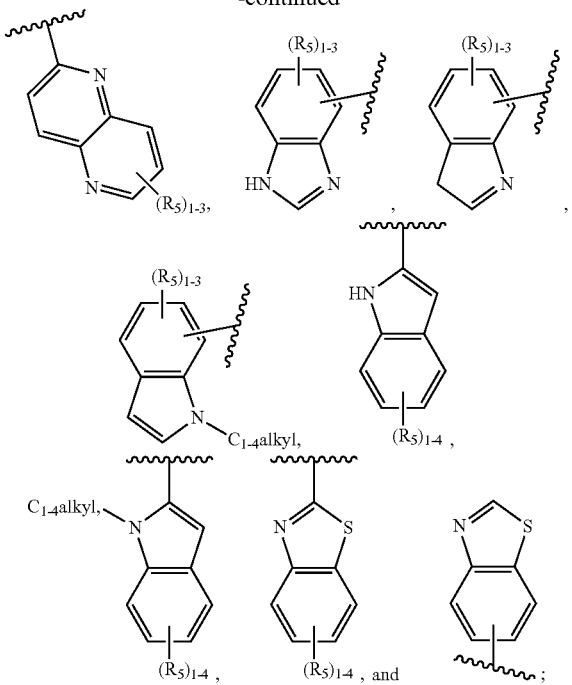

$R_5$ is selected from H, $C_{1-4}$ alkyl substituted with 0-3 $R_e$, F, Cl, Br, =O, CN, $NO_2$, —$(CH_2)_rOR_b$, —$S(O)_pR_c$, —CN, —$(CH_2)_rC(=O)R_b$, —$(CH_2)_rNR_aR_a$, —$(CH_2)_rC(=O)NR_aR_a$, —$(CH_2)_rNHC(=O)R_b$, —$(CH_2)_rNHC(=O)OR_b$, —$(CH_2)_rOC(=O)NR_aR_a$, —$(CH_2)_rNHC(=O)NR_aR_a$, —$(CH_2)_rC(=O)OR_b$, —$(CH_2)_rS(O)_2NR_aR_a$, —$(CH_2)_rNHS(O)_2NR_aR_a$, —$(CH_2)_rNHS(O)_2R_c$, $(CH_2)_r$—$C_{6-12}$ aryl substituted with 0-3 $R_e$, and —$(CH_2)_r$-3- to 15-membered heterocyclyl substituted with 0-3 $R_e$;

$R_a$, at each occurrence, is independently selected from H, CN, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$; or $R_a$ and $R_a$ together with the nitrogen atom to which they are both attached form a 3- to 15-membered heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-3- to 15-membered heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and 3- to 15-membered heterocyclyl;

$R_e$, at each occurrence, is independently selected from $C_{1-6}$ alkyl, $C_{2-6}$ alkenyl, $C_{2-6}$ alkynyl, $C_{6-12}$ aryl, —$(CH_2)_r$—$C_{3-6}$ cycloalkyl, F, Cl, Br, CN, $NO_2$, =O, and $CO_2H$;

p, at each occurrence, is independently selected from zero, 1, and 2; and r, at each occurrence, is independently selected from zero, 1, 2, 3, and 4.

5. The compound according to claim 2, or a pharmaceutically acceptable salt thereof, wherein:

L-R$_2$ is selected from —(CR$_d$R$_d$)$_r$—C$_{6-12}$ aryl substituted with 1-5 R$_7$, —(CR$_d$R$_d$)$_r$—C$_{3-6}$cycloalkyl substituted with 1-5 R$_7$, and —(CR$_d$R$_d$)$_r$-5- to 12-membered heterocyclyl comprising carbon atoms and 1 to 4 heteroatoms selected from N, O, S, and substituted with 1-5 R$_7$;

R$_7$, at each occurrence, is independently selected from H, F, Cl, Br, =O, CN, NO$_2$, —OR$_b$, —S(O)$_p$R$_c$, —C(=O)R$_b$, —(CR$_d$R$_d$)$_r$NR$_a$R$_a$, —(CR$_d$R$_d$)$_r$C(=O)NR$_a$R$_a$, —NR$_a$C(=O)R$_b$, —NR$_a$C(=O)OR$_b$, —OC(=O)NR$_a$R$_a$, —NR$_a$C(=O)NR$_a$R$_a$, —(CR$_d$R$_d$)$_r$C(=O)OR$_b$, —S(O)$_2$NR$_a$R$_a$, —NR$_a$S(O)$_2$NR$_a$R$_a$, —NR$_a$S(O)$_2$R$_c$, C$_{1-6}$ alkyl substituted with 0-5 R$_e$, —(CR$_d$R$_d$)$_r$—C$_{3-6}$carbocyclyl substituted with 0-5 R$_e$, and —(CR$_d$R$_d$)$_r$— 3- to 15-membered heterocyclyl substituted with 0-5 R$_e$;

R$_a$, at each occurrence, is independently selected from H, CN, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$— 3- to 15-membered heterocyclyl substituted with 0-5 R$_e$; or R$_a$ and R$_a$ together with the nitrogen atom to which they are both attached form a 3- to 15-membered heterocyclic ring substituted with 0-5 R$_e$;

R$_b$, at each occurrence, is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$— 3- to 15-membered heterocyclyl substituted with 0-5 R$_e$;

R$_c$, at each occurrence, is independently selected from C$_{1-6}$ alkyl substituted with 0-5 R$_e$, C$_{2-6}$alkenyl substituted with 0-5 R$_e$, C$_{2-6}$alkynyl substituted with 0-5 R$_e$, C$_{3-6}$carbocyclyl, and 3- to 15-membered heterocyclyl;

R$_d$, at each occurrence, is independently selected from H and C$_{1-4}$alkyl substituted with 0-5 R$_e$;

R$_e$, at each occurrence, is independently selected from C$_{1-6}$ alkyl substituted with 0-5 R$_f$, C$_{2-6}$ alkenyl, C$_{2-6}$ alkynyl, C$_{6-12}$ aryl, —(CH$_2$)$_r$—C$_{3-6}$ cycloalkyl, F, Cl, Br, CN, NO$_2$, =O, CO$_2$H, —(CH$_2$)$_r$OR$_f$, SR$_f$, and —(CH$_2$)$_r$NR$_f$R$_f$;

R$_f$, at each occurrence, is independently selected from H, C$_{1-5}$ alkyl, C$_{3-6}$ cycloalkyl, and phenyl, or R$_f$ and R$_f$ together with the nitrogen atom to which they are both attached form a heterocyclic ring optionally substituted with C$_{1-4}$alkyl;

p, at each occurrence, is independently selected from zero, 1, and 2; and r, at each occurrence, is independently selected from zero, 1, 2, 3, and 4.

6. The compound according to claim 5, or a pharmaceutically acceptable salt thereof, wherein:

L-R$_2$ is selected from —(CR$_d$R$_d$)$_r$—C$_{6-12}$ aryl, —(CR$_d$R$_d$)$_r$—C$_{3-6}$cycloalkyl, and —(CR$_d$R$_d$)$_r$-5- to 12-membered heterocyclyl wherein said aryl, cycloalkyl, and heterocycle are selected from:

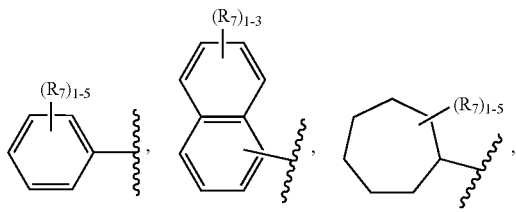

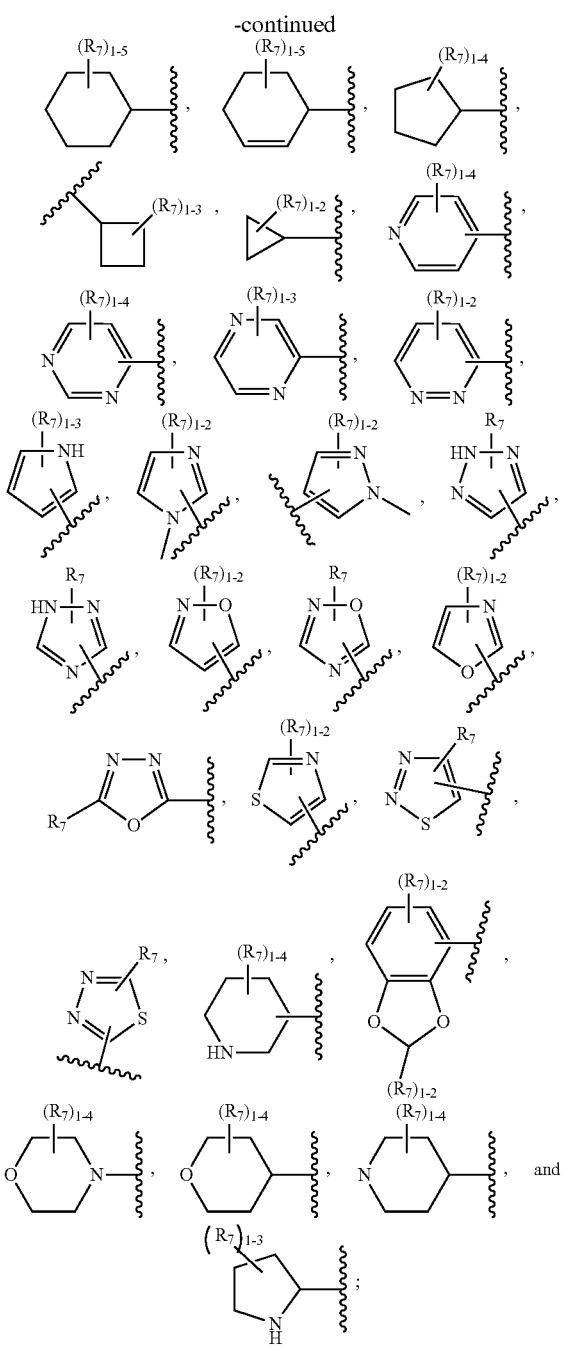

R$_7$, at each occurrence, is independently selected from H, F, Cl, Br, =O, CN, NO$_2$, —OR$_b$, —S(O)$_p$R$_c$, —C(=O)R$_b$, —NR$_a$R$_a$, —C(=O)NR$_a$R$_a$, —NHC(=O)R$_b$, —NHC(=O)OR$_b$, —OC(=O)NR$_a$R$_a$, —NHC(=O)NR$_a$R$_a$, —C(=O)OR$_b$, —S(O)$_2$NR$_a$R$_a$, —NHS(O)$_2$NR$_a$R$_a$, —NHS(O)$_2$R$_c$, C$_{1-6}$ alkyl substituted with 0-5 R$_e$, C$_{3-6}$ cycloalkyl substituted with 0-5 R$_e$, C$_{6-12}$ aryl substituted with 0-5 R$_e$, and 3- to 15-membered heterocyclyl substituted with 0-5 R$_e$;

R$_a$, at each occurrence, is independently selected from H, CN, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$— 3- to 15-membered heterocyclyl substituted with 0-5 R$_e$; or R$_a$ and R$_a$ together with the nitrogen atom to which they are both attached form a 3- to 15-membered heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $C_{6-12}$ aryl substituted with 0-5 $R_e$, and 3- to 15-membered heterocyclyl substituted with 0-5 $R_e$;

$R_c$, at each occurrence, is independently selected from $C_{1-6}$ alkyl substituted with 0-5 $R_e$, $C_{3-6}$carbocyclyl, and 3- to 15-membered heterocyclyl;

$R_d$, at each occurrence, is independently selected from H and $C_{1-4}$alkyl; or $R_d$ and $R_d$ together are $=$O;

$R_e$, at each occurrence, is independently selected from $C_{1-6}$ alkyl, $C_{2-6}$ alkenyl, $C_{2-6}$ alkynyl, $C_{6-12}$ aryl, —$(CH_2)_r$—$C_{3-6}$ cycloalkyl, F, Cl, Br, CN, $NO_2$, $=$O, and $CO_2H$;

p, at each occurrence, is independently selected from zero, 1, and 2; and r, at each occurrence, is independently selected from zero, 1, 2, and 3.

7. The compound according to claim 6, or a pharmaceutically acceptable salt thereof, wherein:

L-$R_2$ is selected from:

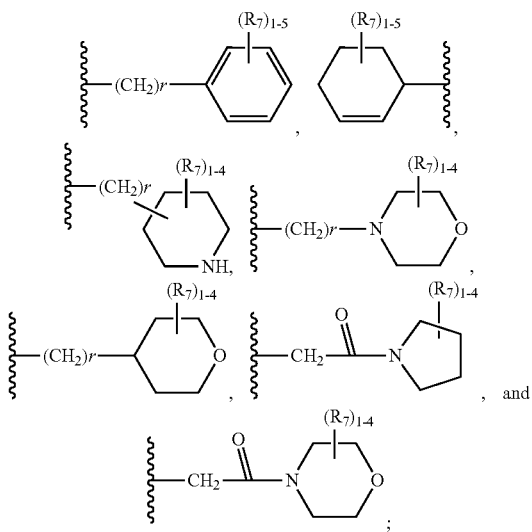

$R_7$, at each occurrence, is independently selected from H, F, Cl, Br, $=$O, CN, $NO_2$, —$OR_b$, —$S(O)_pR_c$, —$C(=O)R_b$, —$NR_aR_a$, —$C(=O)NR_aR_a$, —NHC$(=O)R_b$, —NHC$(=O)OR_b$, —OC$(=O)NR_aR_a$, —NHC$(=O)NR_aR_a$, —C$(=O)OR_b$, —$S(O)_2NR_aR_a$, —$NHS(O)_2NR_aR_a$, —$NHS(O)_2R_c$, $C_{1-6}$ alkyl substituted with 0-5 $R_e$, $C_{6-12}$ aryl substituted with 0-5 $R_e$, and 3- to 15-membered heterocyclyl substituted with 0-5 $R_e$;

$R_a$, at each occurrence, is independently selected from H, CN, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$— 3- to 15-membered heterocyclyl substituted with 0-5 $R_e$; or $R_a$ and $R_a$ together with the nitrogen atom to which they are both attached form a 3- to 15-membered heterocyclic ring substituted with 0-5 $R_e$;

$R_e$, at each occurrence, is independently selected from $C_{1-6}$ alkyl, $C_{2-6}$ alkenyl, $C_{2-6}$ alkynyl, —$(CH_2)_r$—$C_{3-6}$ cycloalkyl, F, Cl, Br, CN, $NO_2$, $=$O, and $CO_2H$; and r, at each occurrence, is independently selected from zero, 1, 2, 3, and 4.

8. The compound according to claim 2, or a pharmaceutically acceptable salt thereof, wherein:

$A_1$ is N, $A_2$ is $CR_6$, and $A_3$ is N;

$R_1$ is selected from $C_{6-12}$ aryl, pyridyl, pyrimidinyl, pyrazinyl, pyridazinyl, triazinyl, furyl, thienyl, imidazolyl, thiazolyl, indolyl, oxazolyl, isoxazolyl, pyrazolyl, triazolyl, tetrazolyl, indazolyl, 1,2,4-thiadiazolyl, isothiazolyl, quinolinyl, and isoquinolinyl, each substituted with substituted with 0-4 $R_5$;

L-$R_2$ is selected from —$(CR_dR_d)_r$—$C_{6-12}$ aryl substituted with 1-5 $R_7$, —$(CR_dR_d)_r$—$C_{3-6}$cycloalkyl substituted with 1-5 $R_7$, and —$(CR_dR_d)_r$-5- to 12-membered heterocyclyl comprising carbon atoms and 1 to 4 heteroatoms selected from N, O, S, and substituted with 1-5 $R_7$;

$R_5$ is selected from H, $C_{1-4}$ alkyl substituted with 0-3 $R_e$, F, Cl, Br, $=$O, CN, $NO_2$, —$OR_b$, —$S(O)_pR_c$, —CN, —$(CH_2)_rC(=O)R_b$, —$(CH_2)_rNR_aR_a$, —$(CH_2)_rC(=O)NR_aR_a$, —$(CH_2)_rNHC(=O)R_b$, —$(CH_2)_rNHC(=O)OR_b$, —$(CH_2)_rOC(=O)NR_aR_a$, —$(CH_2)_rNHC(=O)NR_aR_a$, —$(CH_2)_rC(=O)OR_b$, —$(CH_2)_rS(O)_2NR_aR_a$, —$(CH_2)_rNHS(O)_2NR_aR_a$, —$(CH_2)_rNHS(O)_2R_c$, $(CH_2)_r$-carbocyclyl substituted with 0-3 $R_e$, and —$(CH_2)_r$— 3- to 15-membered heterocyclyl substituted with 0-3 $R_e$;

$R_6$ is selected from H, F, Cl, Br, $C_{1-4}$ alkyl substituted with 0-3 $R_e$, —CN, —$OR_b$, —$S(O)_pR_c$, —$C(=O)R_b$, —$NR_aR_a$, —$C(=O)NR_aR_a$, —$NR_aC(=O)R_b$, —$NR_aC(=O)OR_b$, —$OC(=O)NR_aR_a$, —$NR_aC(=O)NR_aR_a$, —$C(=O)OR_b$, —$(CH_2)_rS(O)_2NR_aR_a$, —$NR_aS(O)_2NR_aR_a$, —$NR_aS(O)_2R_c$, carbocyclyl substituted with 0-3 $R_e$, and 3- to 15-membered heterocyclyl substituted with 0-3 $R_e$;

$R_7$, at each occurrence, is independently selected from H, F, Cl, Br, $=$O, CN, $NO_2$, —$OR_b$, —$S(O)_pR_c$, —$C(=O)R_b$, —$(CR_dR_d)_rNR_aR_a$, —$(CR_dR_d)_rC(=O)NR_aR_a$, —$NR_aC(=O)R_b$, —$NR_aC(=O)OR_b$, —$OC(=O)NR_aR_a$, —$NR_aC(=O)NR_aR_a$, —$(CR_dR_d)_rC(=O)OR_b$, —$S(O)_2NR_aR_a$, —$NR_aS(O)_2NR_aR_a$, —$NR_aS(O)_2R_c$, $C_{1-6}$ alkyl substituted with 0-5 $R_e$, —$(CR_dR_d)_r$—$C_{3-6}$carbocyclyl substituted with 0-5 $R_e$, and —$(CR_dR_d)_r$— 3- to 15-membered heterocyclyl substituted with 0-5 $R_e$;

$R_a$, at each occurrence, is independently selected from H, CN, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$— 3- to 15-membered heterocyclyl substituted with 0-5 $R_e$; or $R_a$ and $R_a$ together with the nitrogen atom to which they are both attached form a 3- to 15-membered heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-3- to 15-membered heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and 3- to 15-membered heterocyclyl;

$R_d$, at each occurrence, is independently selected from H and $C_{1-4}$alkyl substituted with 0-5 $R_e$;

$R_e$, at each occurrence, is independently selected from $C_{1-6}$ alkyl substituted with 0-5 $R_f$, $C_{2-6}$ alkenyl, $C_{2-6}$ alkynyl, $C_{6-12}$ aryl, —(CH$_2$)$_r$—$C_{3-6}$ cycloalkyl, F, Cl, Br, CN, NO$_2$, =O, CO$_2$H, —(CH$_2$)$_r$OR$_f$, SR$_f$, and —(CH$_2$)$_r$NR$_f$R$_f$;

$R_f$, at each occurrence, is independently selected from H, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

p, at each occurrence, is independently selected from zero, 1, and 2; and r, at each occurrence, is independently selected from zero, 1, 2, 3, and 4.

9. The compound according to claim 2, or a pharmaceutically acceptable salt thereof, wherein:

$A_1$ is $CR_6$, $A_2$ is N, and $A_3$ is N;

$R_1$ is selected from $C_{6-12}$ aryl, pyridyl, pyrimidinyl, pyrazinyl, pyridazinyl, triazinyl, furyl, thienyl, imidazolyl, thiazolyl, indolyl, oxazolyl, isoxazolyl, pyrazolyl, triazolyl, tetrazolyl, indazolyl, 1,2,4-thiadiazolyl, isothiazolyl, quinolinyl, and isoquinolinyl, each substituted with substituted with 0-4 $R_5$;

L-$R_2$ is selected from —(CR$_d$R$_d$)$_r$—$C_{6-12}$ aryl substituted with 1-5 $R_7$, —(CR$_d$R$_d$)$_r$—$C_{3-6}$cycloalkyl substituted with 1-5 $R_7$, and —(CR$_d$R$_d$)$_r$-5- to 12-membered heterocyclyl comprising carbon atoms and 1 to 4 heteroatoms selected from N, O, S, and substituted with 1-5 $R_7$;

$R_5$ is selected from H, $C_{1-4}$ alkyl substituted with 0-3 $R_e$, F, Cl, Br, =O, CN, NO$_2$, —OR$_b$, —S(O)$_p$R$_c$, —CN, —(CH$_2$)$_r$C(=O)R$_b$, —(CH$_2$)$_r$NR$_a$R$_a$, —(CH$_2$)$_r$C(=O)NR$_a$R$_a$, —(CH$_2$)$_r$NHC(=O)R$_b$, —(CH$_2$)$_r$NHC(=O)OR$_b$, —(CH$_2$)$_r$OC(=O)NR$_a$R$_a$, —(CH$_2$)$_r$NHC(=O)NR$_a$R$_a$, —(CH$_2$)$_r$C(=O)OR$_b$, —(CH$_2$)$_r$S(O)$_2$NR$_a$R$_a$, —(CH$_2$)$_r$NHS(O)$_2$NR$_a$R$_a$, —(CH$_2$)$_r$NHS(O)$_2$R$_c$, (CH$_2$)$_r$-carbocyclyl substituted with 0-3 $R_e$, and —(CH$_2$)$_r$-heterocyclyl substituted with 0-3 $R_e$;

$R_6$ is selected from H, F, Cl, Br, $C_{1-4}$ alkyl substituted with 0-3 $R_e$, —CN, —OR$_b$, —S(O)$_p$R$_c$, —C(=O)R$_b$, —NR$_a$R$_a$, —C(=O)NR$_a$R$_a$, —NR$_a$C(=O)R$_b$, —NR$_a$C(=O)OR$_b$, —OC(=O)NR$_a$R$_a$, —NR$_a$C(=O)NR$_a$R$_a$, —C(=O)OR$_b$, —(CH$_2$)$_r$S(O)$_2$NR$_a$R$_a$, —NR$_a$S(O)$_2$NR$_a$R$_a$, —NR$_a$S(O)$_2$R$_c$, carbocyclyl substituted with 0-3 $R_e$, and 3- to 15-membered heterocyclyl substituted with 0-3 $R_e$;

$R_7$, at each occurrence, is independently selected from H, F, Cl, Br, =O, CN, NO$_2$, —OR$_b$, —S(O)$_p$R$_c$, —C(=O)R$_b$, —(CR$_d$R$_d$)$_r$NR$_a$R$_a$, —(CR$_d$R$_d$)$_r$C(=O)NR$_a$R$_a$, —NR$_a$C(=O)R$_b$, —NR$_a$C(=O)OR$_b$, —OC(=O)NR$_a$R$_a$, —NR$_a$C(=O)NR$_a$R$_a$, —(CR$_d$R$_d$)$_r$C(=O)OR$_b$, —S(O)$_2$NR$_a$R$_a$, —NR$_a$S(O)$_2$NR$_a$R$_a$, —NR$_a$S(O)$_2$R$_c$, $C_{1-6}$ alkyl substituted with 0-5 $R_e$, —(CR$_d$R$_d$)$_r$—$C_{3-6}$carbocyclyl substituted with 0-5 $R_e$, and —(CR$_d$R$_d$)$_r$— 3- to 15-membered heterocyclyl substituted with 0-5 $R_e$;

$R_a$, at each occurrence, is independently selected from H, CN, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —(CH$_2$)$_r$—$C_{3-10}$carbocyclyl substituted with 0-5 $R_e$, and —(CH$_2$)$_r$— 3- to 15-membered heterocyclyl substituted with 0-5 $R_e$; or $R_a$ and $R_a$ together with the nitrogen atom to which they are both attached form a 3- to 15-membered heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —(CH$_2$)$_r$—$C_{3-10}$carbocyclyl substituted with 0-5 $R_e$, and —(CH$_2$)$_r$— 3- to 15-membered heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and 3- to 15-membered heterocyclyl;

$R_d$, at each occurrence, is independently selected from H and $C_{1-4}$alkyl substituted with 0-5 $R_e$;

$R_e$, at each occurrence, is independently selected from $C_{1-6}$ alkyl substituted with 0-5 $R_f$, $C_{2-6}$ alkenyl, $C_{2-6}$ alkynyl, $C_{6-12}$ aryl, —(CH$_2$)$_r$—$C_{3-6}$ cycloalkyl, F, Cl, Br, CN, NO$_2$, =O, CO$_2$H, —(CH$_2$)$_r$OR$_f$, SR$_f$, and —(CH$_2$)$_r$NR$_f$R$_f$;

$R_f$, at each occurrence, is independently selected from H, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

p, at each occurrence, is independently selected from zero, 1, and 2; and r, at each occurrence, is independently selected from zero, 1, 2, 3, and 4.

10. The compound according to claim 2, having Formula (III), (III)

or a pharmaceutically acceptable salt thereof, wherein:

--- is an optional bond;

$R_1$ is selected from $C_{6-12}$ aryl, pyridyl, pyrimidinyl, pyrazinyl, pyridazinyl, triazinyl, furyl, thienyl, imidazolyl, thiazolyl, indolyl, oxazolyl, isoxazolyl, pyrazolyl, triazolyl, tetrazolyl, indazolyl, 1,2,4-thiadiazolyl, isothiazolyl, quinolinyl, and isoquinolinyl, each substituted with substituted with 0-4 $R_5$;

L-$R_2$ is selected from —(CR$_d$R$_d$)$_r$—$C_{6-12}$ aryl substituted with 1-5 $R_7$, —(CR$_d$R$_d$)$_r$—$C_{3-6}$cycloalkyl substituted with 1-5 $R_7$, and —(CR$_d$R$_d$)$_r$-5- to 12-membered heterocyclyl comprising carbon atoms and 1 to 4 heteroatoms selected from N, O, S, and substituted with 1-5 $R_7$;

$R_3$ is selected from H and $C_{1-4}$ alkyl;

$R_5$ is selected from H, $C_{1-4}$ alkyl substituted with 0-3 $R_e$, F, Cl, Br, =O, CN, NO$_2$, —(CH$_2$)$_r$OR$_b$, —S(O)$_p$R$_c$, —CN, —(CH$_2$)$_r$C(=O)R$_b$, —(CH$_2$)$_r$NR$_a$R$_a$, —(CH$_2$)$_r$C(=O)NR$_a$R$_a$, —(CH$_2$)$_r$NHC(=O)R$_b$, —(CH$_2$)$_r$NHC(=O)OR$_b$, —(CH$_2$)$_r$OC(=O)NR$_a$R$_a$, —(CH$_2$)$_r$NHC(=O)NR$_a$R$_a$, —(CH$_2$)$_r$C(=O)OR$_b$, —(CH$_2$)$_r$S(O)$_2$NR$_a$R$_a$, —(CH$_2$)$_r$NHS(O)$_2$NR$_a$R$_a$, —(CH$_2$)$_r$NHS(O)$_2$R$_c$, (CH$_2$)$_r$-carbocyclyl substituted with 0-3 $R_e$, and —(CH$_2$)$_r$— 3- to 15-membered heterocyclyl substituted with 0-3 $R_e$;

$R_6$ is selected from H, F, Cl, Br, $C_{1-4}$ alkyl substituted with 0-3 $R_e$, —CN, —$OR_b$, —$S(O)_pR_c$, —$C(=O)R_b$, —$NR_aR_a$, —$C(=O)NR_aR_a$, —$NR_aC(=O)R_b$, —$NR_aC(=O)OR_b$, —$OC(=O)NR_aR_a$, —$NR_aC(=O)NR_aR_a$, —$C(=O)OR_b$, —$(CH_2)_rS(O)_2NR_aR_a$, —$NR_aS(O)_2NR_aR_a$, —$NR_aS(O)_2R_c$, carbocyclyl substituted with 0-3 $R_e$, and 3- to 15-membered heterocyclyl substituted with 0-3 $R_e$;

$R_7$, at each occurrence, is independently selected from H, F, Cl, Br, =O, CN, $NO_2$, —$OR_b$, —$S(O)_pR_c$, —$C(=O)R_b$, —$(CR_dR_d)_rNR_aR_a$, —$(CR_dR_d)_rC(=O)NR_aR_a$, —$NR_aC(=O)R_b$, —$NR_aC(=O)OR_b$, —$OC(=O)NR_aR_a$, —$NR_aC(=O)NR_aR_a$, —$(CR_dR_d)_rC(=O)OR_b$, —$S(O)_2NR_aR_a$, —$NR_aS(O)_2NR_aR_a$, —$NR_aS(O)_2R_c$, $C_{1-6}$ alkyl substituted with 0-5 $R_e$, —$(CR_dR_d)_r$—$C_{3-6}$carbocyclyl substituted with 0-5 $R_e$, and —$(CR_dR_d)_r$— 3- to 15-membered heterocyclyl substituted with 0-5 $R_e$;

$R_a$, at each occurrence, is independently selected from H, CN, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$— 3- to 15-membered heterocyclyl substituted with 0-5 $R_e$; or $R_a$ and $R_a$ together with the nitrogen atom to which they are both attached form a 3- to 15-membered heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$— 3- to 15-membered heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and 3- to 15-membered heterocyclyl;

$R_d$, at each occurrence, is independently selected from H and $C_{1-4}$alkyl substituted with 0-5 $R_e$;

$R_e$, at each occurrence, is independently selected from $C_{1-6}$ alkyl substituted with 0-5 $R_f$, $C_{2-6}$ alkenyl, $C_{2-6}$ alkynyl, $C_{6-12}$ aryl, —$(CH_2)_r$—$C_{3-6}$ cycloalkyl, F, Cl, Br, CN, $NO_2$, =O, $CO_2H$, —$(CH_2)_rOR_f$, $SR_f$, and —$(CH_2)_rNR_fR_f$;

$R_f$, at each occurrence, is independently selected from H, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

p, at each occurrence, is independently selected from zero, 1, and 2; and r, at each occurrence, is independently selected from zero, 1, 2, 3, and 4.

11. The compound according to claim 10, or a pharmaceutically acceptable salt thereof, wherein:
--- is an optional bond;
$R_1$ is selected from:

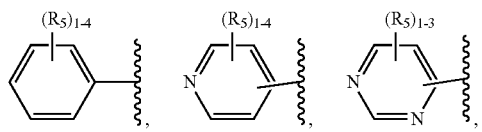

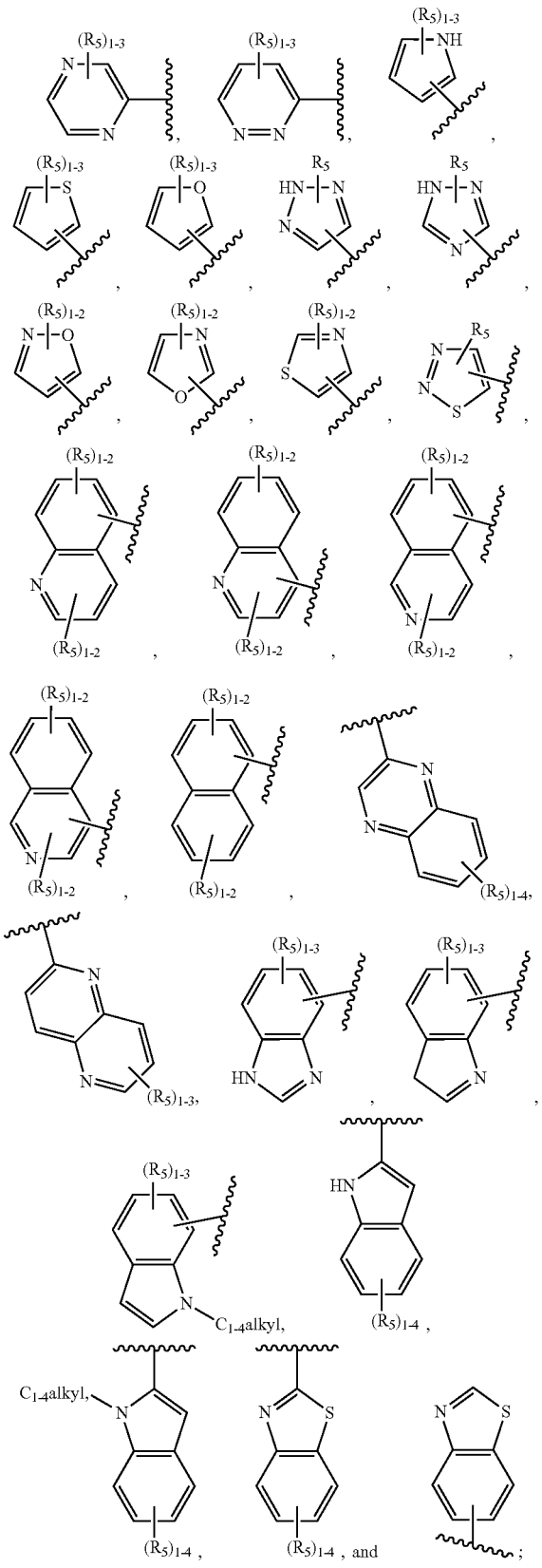

L-$R_2$ is selected from —$(CR_dR_d)_r$-aryl substituted with 1-5 $R_7$, —$(CR_dR_d)_r$—$C_{3-6}$cycloalkyl substituted with 1-5 R$_7$, and —(CR$_d$R$_d$)$_r$-5- to 12-membered heterocyclyl wherein said aryl, cycloalkyl, and heterocycle are selected from:

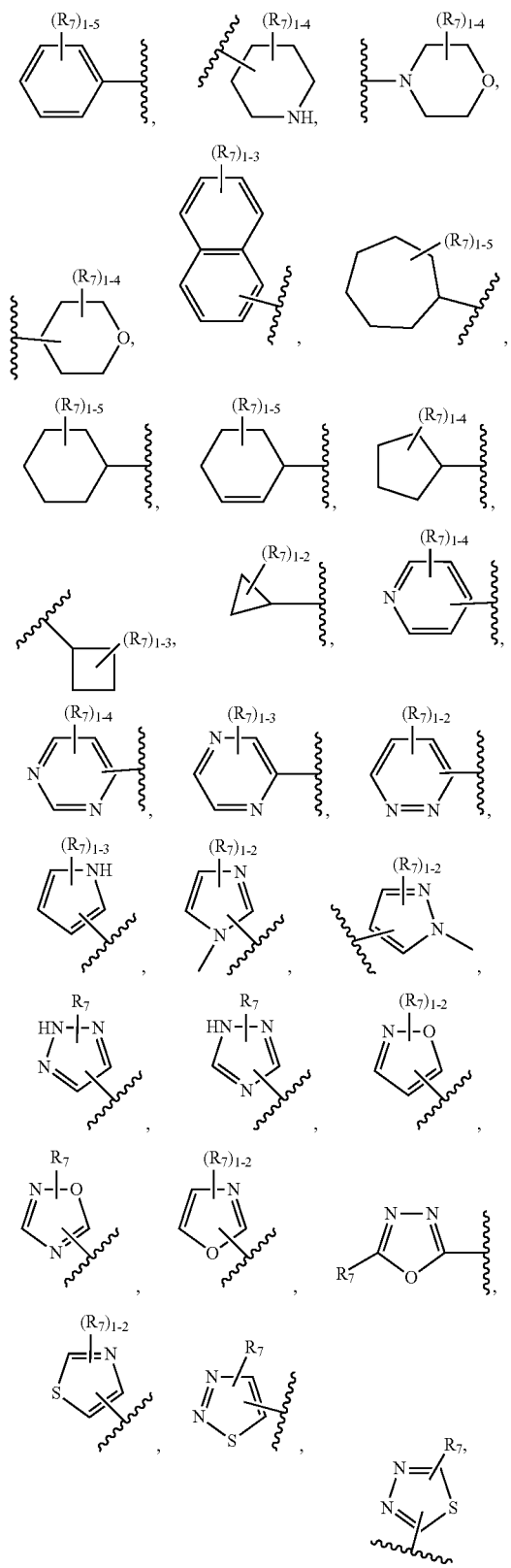

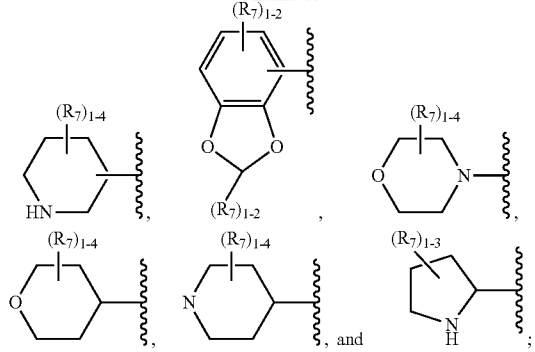

R$_3$ is selected from H and C$_{1-4}$ alkyl;

R$_5$ is selected from H, C$_{1-4}$ alkyl substituted with 0-3 R$_e$, F, Cl, Br, =O, CN, NO$_2$, —(CH$_2$)$_r$OR$_b$, —S(O)$_p$R$_c$, —CN, —OR$_b$, —(CH$_2$)$_r$C(=O)R$_b$, —(CH$_2$)$_r$NR$_a$R$_a$, —(CH$_2$)$_r$C(=O)NR$_a$R$_a$, —(CH$_2$)$_r$NHC(=O)R$_b$, —(CH$_2$)$_r$NHC(=O)OR$_b$, —(CH$_2$)$_r$OC(=O)NR$_a$R$_a$, —(CH$_2$)$_r$NHC(=O)NR$_a$R$_a$, —(CH$_2$)$_r$C(=O)OR$_b$, —(CH$_2$)$_r$S(O)$_2$NR$_a$R$_a$, —(CH$_2$)$_r$NHS(O)$_2$NR$_a$R$_a$, —(CH$_2$)$_r$NHS(O)$_2$R$_c$, (CH$_2$)$_r$—C$_{6-12}$ aryl substituted with 0-3 R$_e$, and —(CH$_2$)$_r$— 3- to 15-membered heterocyclyl substituted with 0-3 R$_e$;

R$_6$ is selected from H, F, Cl, Br, C$_{1-4}$ alkyl substituted with 0-3 R$_e$, —CN, —OR$_b$, —NR$_a$R$_a$, —NR$_a$C(=O)R$_b$, —NR$_a$C(=O)OR$_b$, —NR$_a$C(=O)NR$_a$R$_a$, —NR$_a$S(O)$_2$R$_c$, phenyl substituted with 0-3 R$_e$, C$_{3-6}$ cycloalkyl substituted with 0-3 R$_e$, and 3- to 15-membered heterocyclyl substituted with 0-3 R$_e$;

R$_7$, at each occurrence, is independently selected from H, F, Cl, Br, =O, CN, NO$_2$, —OR$_b$, —S(O)$_p$R$_c$, —C(=O)R$_b$, —NR$_a$R$_a$, —C(=O)NR$_a$R$_a$, —NHC(=O)R$_b$, —NHC(=O)OR$_b$, —OC(=O)NR$_a$R$_a$, —NHC(=O)NR$_a$R$_a$, —C(=O)OR$_b$, —S(O)$_2$NR$_a$R$_a$, —NHS(O)$_2$NR$_a$R$_a$, —NHS(O)$_2$R$_c$, C$_{1-6}$ alkyl substituted with 0-5 R$_e$, C$_{6-12}$ aryl substituted with 0-5 R$_e$, and 3- to 15-membered heterocyclyl substituted with 0-5 R$_e$;

R$_a$, at each occurrence, is independently selected from H, CN, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$— 3- to 15-membered heterocyclyl substituted with 0-5 R$_e$; or R$_a$ and R$_a$ together with the nitrogen atom to which they are both attached form a 3- to 15-membered heterocyclic ring substituted with 0-5 R$_e$;

R$_b$, at each occurrence, is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-6}$ cycloalkyl substituted with 0-5 R$_e$, —(CH$_2$)$_r$-aryl substituted with 0-5 R$_e$, and —(CH$_2$)$_r$— 3- to 15-membered heterocyclyl substituted with 0-5 R$_e$;

R$_c$, at each occurrence, is independently selected from C$_{1-6}$ alkyl substituted with 0-5 R$_e$, C$_{2-6}$alkenyl substituted with 0-5 R$_e$, C$_{2-6}$alkynyl substituted with 0-5 R$_e$, C$_{3-6}$carbocyclyl, and 3- to 15-membered heterocyclyl;

R$_d$, at each occurrence, is independently selected from H and C$_{1-4}$alkyl;

R$_e$, at each occurrence, is independently selected from C$_{1-6}$ alkyl, C$_{2-6}$ alkenyl, C$_{2-6}$ alkynyl, C$_{6-12}$ aryl, —$(CH_2)_r$—$C_{3-6}$ cycloalkyl, F, Cl, Br, CN, $NO_2$, =O, OH, $OC_{1-4}$ alkyl, and $CO_2H$;

p, at each occurrence, is independently selected from zero, 1, and 2; and r, at each occurrence, is independently selected from zero, 1, 2, 3, and 4.

12. The compound according to claim 11, or a pharmaceutically acceptable salt thereof, wherein:

--- is an optional bond;

$R_1$ is selected from:

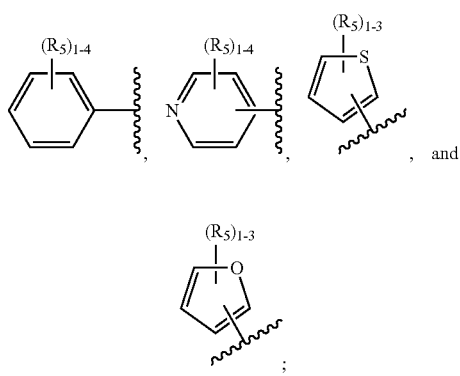

L-$R_2$ is selected from —$(CH_2)_r$-aryl, —$(CH_2)_r$—$C_{3-6}$cycloalkyl, and —$(CH_2)_r$-5- to 12-membered heterocyclyl wherein said aryl, cycloalkyl, and heterocycle are selected from:

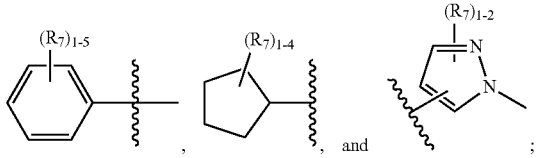

$R_3$ is selected from H and $C_{1-4}$ alkyl;

$R_5$ is selected from H, $C_{1-4}$ alkyl substituted with 0-3 $R_e$, F, Cl, and —$(CH_2)_rOR_b$;

$R_6$ is selected from H, —$NR_aR_a$, and —$NR_aC(=O)R_b$;

$R_7$, at each occurrence, is independently selected from H, F, CN, —$OR_b$, $C_{1-6}$ alkyl substituted with 0-5 $R_e$, and 3- to 15-membered heterocyclyl substituted with 0-5 $R_e$;

$R_a$, at each occurrence, is independently selected from H, and $C_{3-10}$carbocyclyl substituted with 0-5 $R_e$;

$R_b$, at each occurrence, is independently selected from H, $C_{1-6}$ alkyl substituted with 0-5 $R_e$, $C_{3-6}$ cycloalkyl substituted with 0-5 $R_e$;

$R_e$, at each occurrence, is independently selected from $C_{1-6}$ alkyl and F; and r, at each occurrence, is independently selected from zero, 1 and 2.

13. A pharmaceutical composition comprising one or more compounds of claim 1 and a pharmaceutically acceptable carrier.

14. A method of inhibiting casein kinase RIPK3 activity in a patient, comprising administering to the patient in need thereof, a therapeutically effective amount of one or more compounds according to claim 1.

* * * * *